US012581853B2

(12) United States Patent
Park et al.

(10) Patent No.: US 12,581,853 B2
(45) Date of Patent: Mar. 17, 2026

(54) ORGANIC COMPOUND AND SENSOR AND SENSOR EMBEDDED DISPLAY PANEL AND ELECTRONIC DEVICE

(71) Applicant: Samsung Electronics Co., Ltd., Suwon-si (KR)

(72) Inventors: Jeong Il Park, Seongnam-si (KR); Sung Young Yun, Suwon-si (KR); Hyeongju Kim, Changwon-si (KR); Kyung Bae Park, Suwon-si (KR); Jisoo Shin, Suwon-si (KR); Taejin Choi, Suwon-si (KR); Chul Joon Heo, Suwon-si (KR)

(73) Assignee: Samsung Display Co., Ltd., Gyeonggi-do (KR)

( * ) Notice: Subject to any disclaimer, the term of this patent is extended or adjusted under 35 U.S.C. 154(b) by 692 days.

(21) Appl. No.: 17/954,986

(22) Filed: Sep. 28, 2022

(65) Prior Publication Data

US 2023/0134363 A1 May 4, 2023

(30) Foreign Application Priority Data

Sep. 30, 2021 (KR) ........................ 10-2021-0130176

(51) Int. Cl.

| | |
|---|---|
| ***H10K 85/60*** | (2023.01) |
| ***C07D 495/04*** | (2006.01) |
| ***C07D 495/22*** | (2006.01) |
| ***C07D 517/04*** | (2006.01) |
| ***C07D 517/16*** | (2006.01) |
| ***G06V 40/13*** | (2022.01) |
| ***H10K 30/30*** | (2023.01) |
| ***H10K 65/00*** | (2023.01) |

(52) U.S. Cl.

CPC ......... *H10K 85/657* (2023.02); *C07D 495/04* (2013.01); *C07D 517/04* (2013.01); *G06V 40/1318* (2022.01); *H10K 85/654* (2023.02); *H10K 85/6576* (2023.02); *H10K 30/30* (2023.02); *H10K 65/00* (2023.02)

(58) Field of Classification Search

CPC .. C07D 495/04; C07D 517/04; C07D 495/22; C07D 517/16

See application file for complete search history.

(56) References Cited

U.S. PATENT DOCUMENTS

| | | | | |
|---|---|---|---|---|
| 8,153,439 B2 * | 4/2012 | Zamborini | ........... | G01N 27/127 436/127 |
| 9,911,920 B2 * | 3/2018 | Bulliard | ............... | H10K 85/654 |
| 10,439,153 B2 | 10/2019 | Lim et al. | | |
| 2016/0020401 A1 * | 1/2016 | Bulliard | ............... | H10K 85/615 548/183 |

FOREIGN PATENT DOCUMENTS

| | | | | |
|---|---|---|---|---|
| CN | 108546267 A | 9/2018 | | |
| CN | 108864141 A | 11/2018 | | |
| KR | 2016/0128227 A | 11/2016 | | |
| WO | WO-2014026244 A1 * | 2/2014 | ........... | C07D 413/14 |
| WO | WO-2020/165686 A1 | 8/2020 | | |

OTHER PUBLICATIONS

Li et al., Journal of Molecular Graphics & Modelling, 2015, 59, pp. 50-58. (Year: 2015).*

Shu et al., Journal of Materials Chemistry C: Materials for Optical and Electronic Devices (2014), 2(20), 3895-3899. (Year: 2014).*

Kantlehner et al., Journal fuer Praktische Chemie/Chemiker-Zeitung (1996), 338(5), 403-413. (Year: 1996).*

A machine generated English translation of Kantlehner et al., Journal fuer Praktische Chemie/Chemiker-Zeitung (1996), 338(5), 403-413. (Year: 1996).*

Kwanghee Koh Park, et al., 'Facile Synthesis of Regio-Isomeric Naphthofurans and Benzodifurans,' *Tetrahedron,* vol. 61, Issue 3, Jan. 17, 2005, pp. 545-553.

* cited by examiner

*Primary Examiner* — Laura L Stockton

(74) *Attorney, Agent, or Firm* — Harness, Dickey & Pierce, P.L.C.

(57) ABSTRACT

An organic compound is represented by Chemical Formula 1.

[Chemical Formula 1]

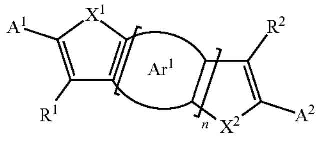

In Chemical Formula 1, $X^1$, $X^2$, $Ar^1$, n, $R^1$, $R^2$, $A^1$, and $A^2$ are each the same as in the specification.

23 Claims, 13 Drawing Sheets

ORGANIC COMPOUND AND SENSOR AND SENSOR EMBEDDED DISPLAY PANEL AND ELECTRONIC DEVICE

CROSS-REFERENCE TO RELATED APPLICATION

This application claims priority to and the benefit of Korean Patent Application No. 10-2021-0130176 filed in the Korean Intellectual Property Office on Sep. 30, 2021, the entire contents of which are incorporated herein by reference.

BACKGROUND

1. Field

Organic compounds, sensors, sensor-embedded display panels, and electronic devices are disclosed.

2. Description of the Related Art

Recently, there is an increasing demand for a display device implementing a biometric recognition technology that authenticates the person by extracting specific biometric information or behavioral characteristic information of a person with an automated device centering on finance, healthcare, and mobile. Accordingly, the display device may include a sensor for biometric recognition.

On the other hand, such a sensor for biometric recognition may be divided into an electrostatic type, an ultrasonic type, or an optical type. Among them, the optical type sensor is a sensor configured to absorb light and convert the absorbed light into an electrical signal. The organic material has a large extinction coefficient and may be configured to selectively absorb light in a specific wavelength spectrum according to a molecular structure, and thus it may be usefully applied to an optical type sensor.

SUMMARY

The sensor provided in the display device may be disposed under the display panel or may be manufactured as a separate module and mounted on the outside of the display panel. However, when the sensor is disposed under the display panel, the object should be recognized through the display panel, various films, and/or parts, and thus performance may be degraded. When the sensor is manufactured and mounted as a separate module, there are limitations in terms of design and usability.

Accordingly, an embedded sensor having a sensor embedded in the display panel may be proposed. However, since the performance and physical properties required for the display panel and the sensor are different from each other, it may be difficult to implement in an integrated form.

Some example embodiments provide an organic compound that may be effectively applied to a sensor.

Some example embodiments provide a sensor including the organic compound.

Some example embodiments provide a sensor-embedded display panel including the organic compound or the sensor.

Some example embodiments provide an electronic device including the organic compound, the sensor, or the sensor-embedded display panel.

According to some example embodiments, an organic compound represented by Chemical Formula 1 is provided.

[Chemical Formula 1]

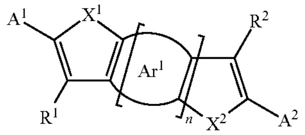

In Chemical Formula 1, $X^1$ and $X^2$ are each independently a chalcogen element, $Ar^1$ is a substituted or unsubstituted C6 to C30 aromatic ring (i.e., aromatic hydrocarbon ring or heteroaromatic ring), n is 0 or 1, $R^1$ and $R^2$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, $A^1$ and $A^2$ are each independently an electron accepting group represented by Chemical Formula 1A, 1B, or 1C,

[Chemical Formula 1A] [Chemical Formula 1B] [Chemical Formula 1C]

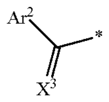

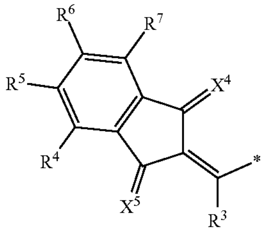

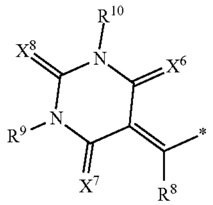

In Chemical Formula 1A, 1B, or 1C, $X^3$ to $X^8$ are each independently a chalcogen element, and when $X^6$ and $X^7$ are each O, $X^8$ is not S, $Ar^2$ is a C6 to C30 aryl group substituted with at least one halogen, at least one C1 to C30 haloalkyl group, at least one cyano group, at least one dicyanovinyl group, or any combination thereof; a C3 to C30 heterocyclic group substituted with at least one halogen, at least one C1 to C30 haloalkyl group, at least one cyano group, at least one dicyanovinyl group, or any combination thereof; or any combination thereof, $R^3$ to $R^{10}$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, $R^4$ to $R^7$ are each independently present or two adjacent ones of $R^4$ to $R^7$ are linked to each other to form a ring, and

* is a linking point with Chemical Formula 1.

$Ar^1$ may be substituted or unsubstituted benzene, substituted or unsubstituted naphthalene, substituted or unsubstituted anthracene, substituted or unsubstituted phenanthrene, substituted or unsubstituted tetracene, substituted or unsubstituted furan, substituted or unsubstituted thiophene, substituted or unsubstituted selenophene, substituted or unsubstituted tellurophene, or a fused ring of two or more therefrom.

$Ar^1$ may be one ring of a plurality of substituted or unsubstituted rings listed in Group 1.

[Group 1]

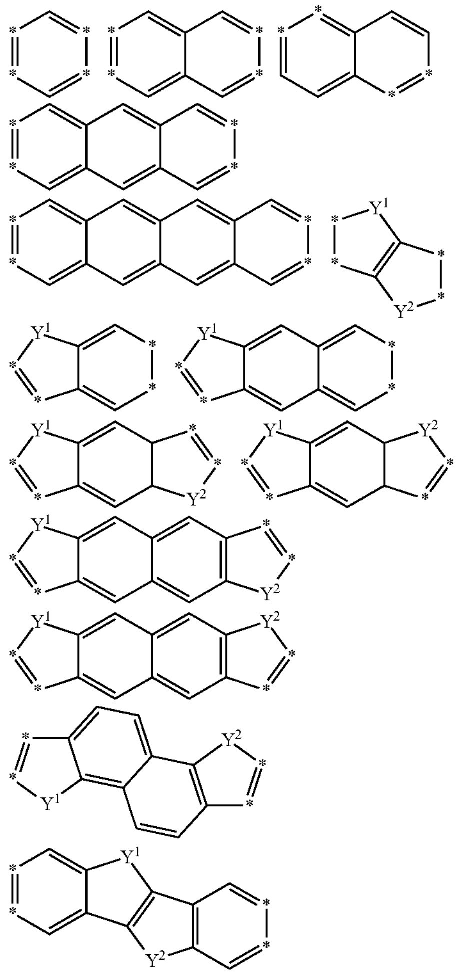

-continued

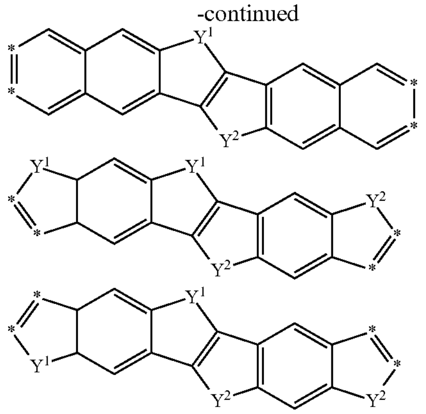

In Group 1, $Y^1$ and $Y^2$ are each independently a chalcogen element,

* is a linking point with Chemical Formula 1.

$A^1$ and $A^2$ may each be the electron accepting group represented by Chemical Formula 1A, wherein $Ar^2$ of Chemical Formula 1A may be a halogen-substituted phenyl group; a halogen-substituted naphthyl group; a halogen-substituted anthracenyl group; a halogen-substituted phenanthrenyl group; a phenyl group substituted with a C1 to C30 haloalkyl group; a naphthyl group substituted with a C1 to C30 haloalkyl group; an anthracenyl group substituted with a C1 to C30 haloalkyl group; a phenanthrenyl group substituted with a C1 to C30 haloalkyl group; a phenyl group substituted with a cyano group; a naphthyl group substituted with a cyano group; an anthracenyl group substituted with a cyano group; a phenanthrenyl group substituted with a cyano group; a phenyl group substituted with a dicyanovinyl group; a naphthyl group substituted with a dicyanovinyl group; an anthracenyl group substituted with a dicyanovinyl group; a phenanthrenyl group substituted with a dicyanovinyl group; or any combination thereof.

$X^3$ may be different from $X^1$ and $X^2$, respectively.

$A^1$ and $A^2$ may each be an electron accepting group represented by Chemical Formula 1B, and $X^4$ and $X^5$ may be different from $X^1$ and $X^2$, respectively.

$A^1$ and $A^2$ may each be an electron accepting group represented by Chemical Formula 1C, and $X^6$, $X^7$, and $X^8$ may be different from $X^1$ and $X^2$, respectively.

At least one of $X^1$ or $X^2$ may be Se or Te.

A LUMO energy level of the organic compound may be about 2.5 eV to about 4.5 eV.

The organic compound may be represented by one of Chemical Formulas 1A-1 to 1C-4.

[Chemical Formula 1A-1]

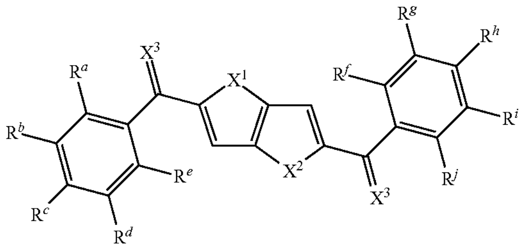

[Chemical Formula 1A-2]

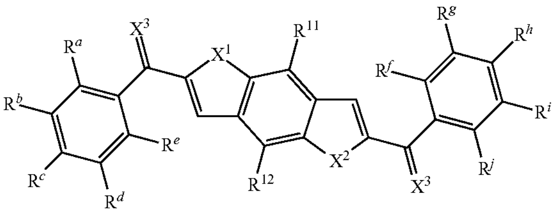

-continued

[Chemical Formula 1A-3]

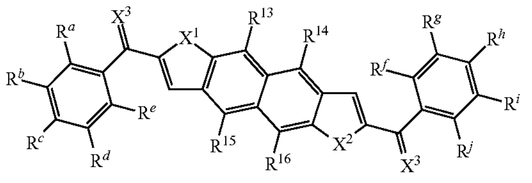

[Chemical Formula 1A-4]

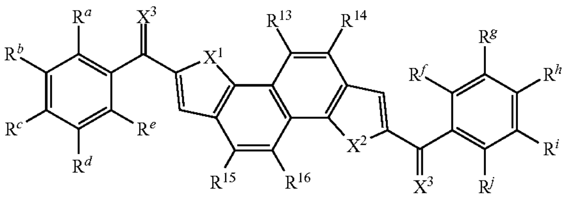

[Chemical Formula 1B-1]

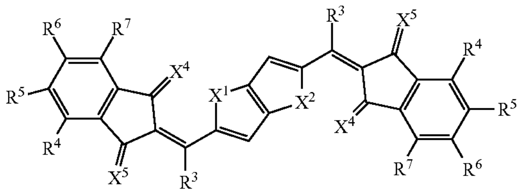

[Chemical Formula 1B-2]

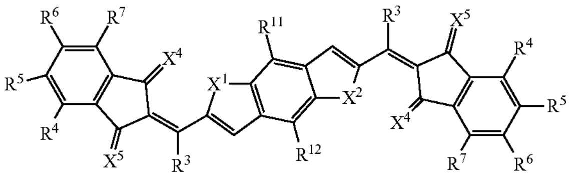

[Chemical Formula 1B-3]

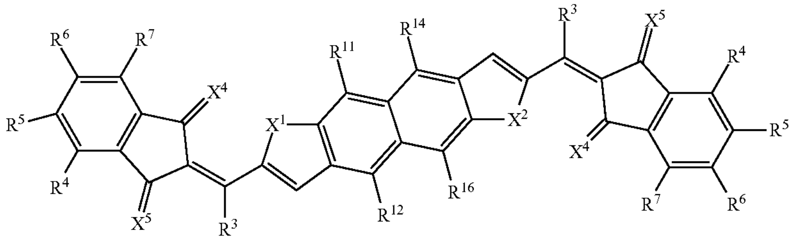

[Chemical Formula 1B-4]

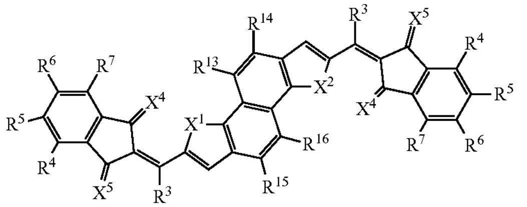

[Chemical Formula 1C-1]

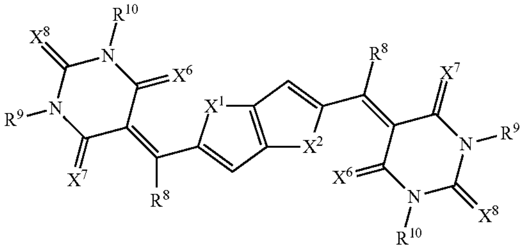

[Chemical Formula 1C-2]

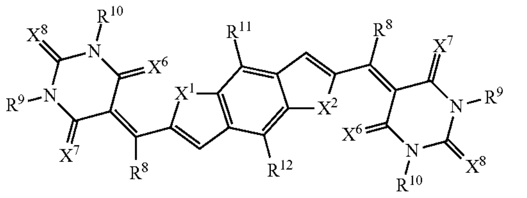

[Chemical Formula 1C-3]

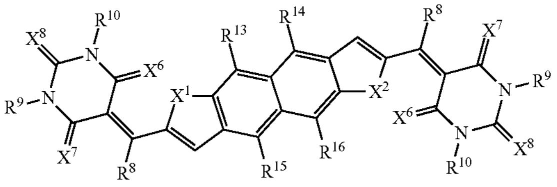

[Chemical Formula 1C-4]

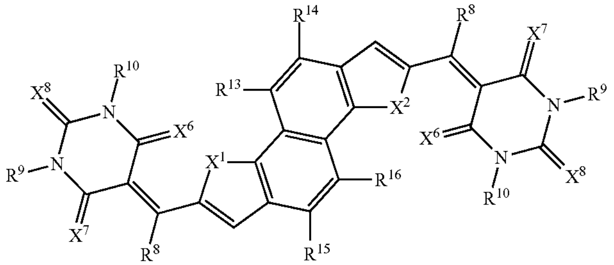

In Chemical Formulas 1A-1 to 1C-4, $X^1$ to $X^8$ may each independently be a chalcogen element, and when $X^6$ and $X^7$ are each O, $X^8$ is not S, $R^3$ to $R^{16}$ may each independently be hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, $R^a$ to $R^j$ may each independently be hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, a dicyanovinyl group, or any combination thereof, at least one of $R^a$ to $R^e$ may be a halogen, a C1 to C30 haloalkyl group, a cyano group, a dicyanovinyl group, or any combination thereof, and at least one of $R^f$ to $R^j$ may be a halogen, a C1 to C30 haloalkyl group, a cyano group, a dicyanovinyl group, or any combination thereof.

According to some example embodiments, a sensor includes a first electrode, a second electrode, and a photoelectric conversion layer between the first electrode and the second electrode and including the organic compound.

The organic compound may be an n-type semiconductor, and may further include a p-type semiconductor forming a pn junction with the organic compound, and the p-type semiconductor may be represented by Chemical Formula 2.

[Chemical Formula 2]

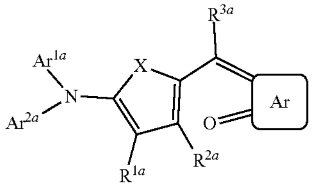

In Chemical Formula 2,

X may be O, S, Se, Te, SO, $SO_2$, $CR^bR^c$, or $SiR^dR^e$,

Ar may be a substituted or unsubstituted C6 to C30 arylene group, a substituted or unsubstituted C3 to C30 heterocyclic group, or a fused ring of two or more therefrom, $Ar^{1a}$ and $Ar^{2a}$ may each independently be a substituted or unsubstituted C6 to C30 aryl(ene) group or a substituted or unsubstituted C3 to C30 heteroaryl(ene) group, $R^{1a}$ to $R^{3a}$ and $R^b$ to $R^e$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, $Ar^{1a}$, $Ar^{2a}$, $R^{1a}$, and $R^{2a}$ may each independently be present or two adjacent ones thereof (e.g., a pair of $Ar^{1a}$ and $Ar^{2a}$, and/or a pair of $Ar^{2a}$ and $R^{1a}$) may be linked to each other to form a ring.

The p-type semiconductor may be represented by Chemical Formula 2A or 2B.

[Chemical Formula 2A]

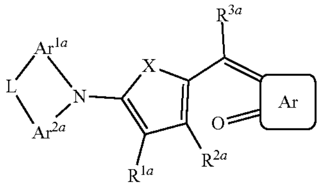

-continued

[Chemical Formula 2B]

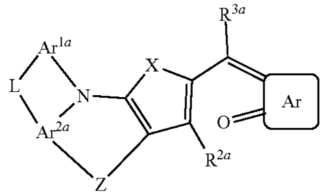

In Chemical Formulas 2A and 2B,

X may be O, S, Se, Te, SO, $SO_2$, $CR^bR^c$, or $SiR^dR^e$,

Ar may be a substituted or unsubstituted C6 to C30 arylene group, a substituted or unsubstituted C3 to C30 heterocyclic group, or a fused ring of two or more therefrom, $Ar^{1a}$ and $Ar^{2a}$ may each independently be a substituted or unsubstituted C6 to C30 arylene group or a substituted or unsubstituted C3 to C30 heteroarylene group, L and Z may each independently be a single bond, O, S, Se, Te, SO, $SO_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and $R^{1a}$, $R^{2a}$, $R^{3a}$, and $R^b$ to $R^l$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof.

According to some example embodiments, a sensor-embedded display panel includes a substrate, a light emitting element on the substrate and including a light emitting layer, and a light absorption sensor on the substrate and including a photoelectric conversion layer, wherein the light emitting element and the light absorption sensor are arranged in parallel along an in-plane direction of the substrate such that the photoelectric conversion layer and the light emitting layer at least partially overlap in the in-plane direction, and the photoelectric conversion layer includes the organic compound.

The organic compound may be an n-type semiconductor, and the photoelectric conversion layer may further include a p-type semiconductor forming a pn junction with the organic compound, and the p-type semiconductor may be represented by Chemical Formula 2.

The p-type semiconductor may be represented by Chemical Formula 2A or 2B.

The light emitting element may include first, second, and third light emitting elements configured to emit light of different wavelength spectra in relation to each other, and the light absorption sensor may be configured to absorb light emitted from at least one of the first, second, or third light emitting elements and then reflected by a recognition target to the light absorption sensor, and convert the absorbed light into an electrical signal.

The light emitting element and the light absorption sensor may each include a separate portion of a common electrode configured to apply a common voltage to the light emitting element and the light absorption sensor, respectively, and the sensor-embedded display panel may further include a first common auxiliary layer that is a single piece of material that extends continuously between the light emitting element and the common electrode and between the photoelectric conversion layer and the common electrode.

A difference between the LUMO energy level of the first common auxiliary layer and the LUMO energy level of the organic compound may be about 0 eV to about 1.2 eV.

The sensor-embedded display panel may further include a second common auxiliary layer that is a single piece of material that extends continuously between the light emitting element and the substrate and between the light absorption sensor and the substrate.

The sensor-embedded display panel may include a display area configured to display a color and a non-display area excluding the display area, and the light absorption sensor may be in the non-display area.

The light emitting element may include a first light emitting element configured to emit light of a red wavelength spectrum, a second light emitting element configured to emit light of a green wavelength spectrum, and a third light emitting element configured to emit light of a blue wavelength spectrum, the display area may include a plurality of first subpixels configured to display light of the red wavelength spectrum and including the first light emitting element, a plurality of second subpixels configured to display light of the green wavelength spectrum and including the second light emitting element, and a plurality of third subpixels configured to display light of the blue wavelength spectrum and including the third light emitting element, and the light absorption sensor may be between at least two subpixels of a first subpixel of the plurality of first subpixels, a second subpixel of the plurality of second subpixels, or a third subpixel of the plurality of third subpixels.

According to some example embodiments, an electronic device including the sensor or the sensor-embedded display panel is provided.

According to some example embodiments, an organic compound may be represented by Chemical Formula 1:

[Chemical Formula 1]

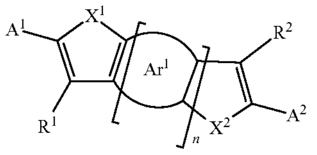

wherein, in Chemical Formula 1, $X^1$ and $X^2$ are each independently a chalcogen element, $Ar^1$ is a substituted or unsubstituted C6 to C30 aromatic ring, n is 0 or 1, $R^1$ and $R^2$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, and $A^1$ and $A^2$ are each independently an electron accepting group.

$A^1$ and $A^2$ may each independently be an electron accepting group represented by Chemical Formula 1A, 1B, or 1C,

[Chemical Formula 1A]

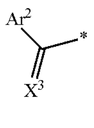

-continued

[Chemical Formula 1B]

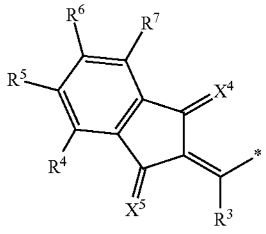

[Chemical Formula 1C]

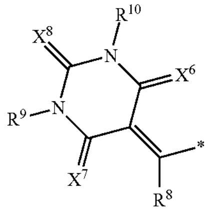

wherein, in Chemical Formula 1A, 1B, and/or 1C, $X^3$ to $X^8$ are each independently a chalcogen element, and when $X^6$ and $X^7$ are each O, $X^8$ is not S, $Ar^2$ is a C6 to C30 aryl group substituted with at least one halogen, at least one C1 to C30 haloalkyl group, at least one cyano group, at least one dicyanovinyl group, or any combination thereof; a C3 to C30 heterocyclic group substituted with at least one halogen, at least one C1 to C30 haloalkyl group, at least one cyano group, at least one dicyanovinyl group, or any combination thereof; or any combination thereof, $R^3$ to $R^{10}$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, $R^4$ to $R^7$ are each independently present or two adjacent ones of $R^4$ to $R^7$ are linked to each other to form a ring, and

* is a linking point with Chemical Formula 1.

$Ar^1$ may be a substituted or unsubstituted benzene, a substituted or unsubstituted naphthalene, a substituted or unsubstituted anthracene, a substituted or unsubstituted phenanthrene, a substituted or unsubstituted tetracene, a substituted or unsubstituted furan, a substituted or unsubstituted thiophene, a substituted or unsubstituted selenophene, a substituted or unsubstituted tellurophene or a fused ring of two or more therefrom.

A sensor may include a first electrode, a second electrode, and a photoelectric conversion layer between the first electrode and the second electrode, the photoelectric conversion layer comprising the organic compound.

An electronic device may include the sensor.

According to some example embodiments, an organic compound may be represented by Chemical Formula 3:

$$D1\text{-}A1\text{-}D2 \quad \text{[Chemical Formula 3]}$$

wherein, in Chemical Formula 3,

A1 is an electron accepting group, and

D1 and D2 are each independently an electron donating group represented by Chemical Formula 3A,

[Chemical Formula 3A]

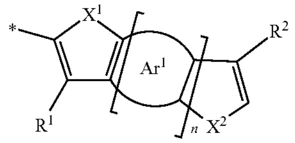

wherein, in Chemical Formula 3A, $X^1$ and $X^2$ are independently a chalcogen element, $Ar^1$ is a substituted or unsubstituted C6 to C30 aromatic ring, n is 0 or 1, $R^1$ and $R^2$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, and

* is a linking point with Chemical Formula 3.

A1 may be represented by Chemical Formula 3B, 3C, or 3D,

[Chemical Formula 3B]

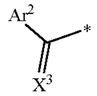

[Chemical Formula 3C]

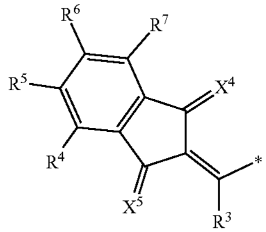

[Chemical Formula 3D]

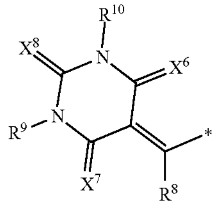

wherein, in Chemical Formula 3B, 3C, and/or 3D,

* is a linking point with D1, $X^3$ to $X^8$ are each independently a chalcogen element, and when $X^6$ and $X^7$ are each O, $X^8$ is not S, $Ar^2$ is a group including a C6 to C30 aryl group substituted with at least one halogen, at least one C1 to C30 haloalkyl group, at least one cyano group, at least one dicyanovinyl group, or any combination thereof; a C3 to C30 heterocyclic group substituted with at least one halogen, at least one C1 to C30 haloalkyl group, at least one cyano group, at least one dicyanovinyl group, or any combination thereof; or any combination thereof, wherein one hydrogen of the group is substituted with a linking point with D2, $R^3$ to $R^{10}$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, a linking point with D2, or any combination thereof, wherein one of $R^3$ to $R^{10}$, includes the linking point with D2, and $R^4$ to $R^7$ are each independently present or two adjacent ones of $R^4$ to $R^7$ are linked to each other to form a ring.

A1 may be one of *—R—(C═O)—R'—*, *—R—(C═O)—*, *—(C═O)—R'—*, or *—(C═O)—*, wherein *'s are linking points with respective ones of D1 or D2, and R and R' are each independently a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, or any combination thereof.

A sensor may include a first electrode, a second electrode, and a photoelectric conversion layer between the first electrode and the second electrode, the photoelectric conversion layer comprising the organic compound.

An electronic device may include the sensor.

Since the compound has good electrical and thermal properties, it may be effectively applied to a sensor and a sensor-embedded display panel.

DETAILED DESCRIPTION

Figure 1:
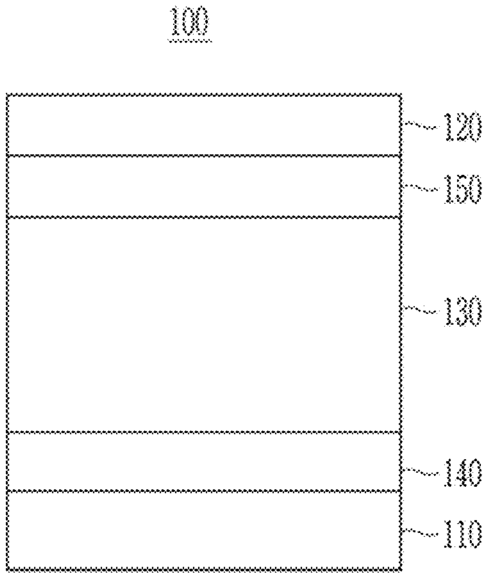
FIG. 1 is a cross-sectional view showing an example of a sensor according to some example embodiments.

Hereinafter, example embodiments will be described in detail so that a person skilled in the art would understand the same. However, a structure that is actually applied may be implemented in various different forms and is not limited to the embodiments described herein.

In the drawings, the thickness of layers, films, panels, regions, etc., are exaggerated for clarity. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Hereinafter, the terms "lower" and "upper" are used for better understanding and ease of description, but do not limit the location relationship.

As used herein, when a definition is not otherwise provided, "substituted" refers to replacement of hydrogen of a compound or a group by a substituent selected from a halogen, a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C30 alkyl group, a C2 to C30 alkenyl group, a C2 to C30 alkynyl group, a C6 to C30 aryl group, a C7 to C30 arylalkyl group, a C1 to C30 alkoxy group, a C1 to C20 heteroalkyl group, a C3 to C20 heterocyclic group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and any combination thereof.

As used herein, when a definition is not otherwise provided, "hetero" refers to one including 1 to 4 heteroatoms selected from N, O, S, Se, Te, Si, and P.

As used herein, when a definition is not otherwise provided, "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, and the like).

As used herein, when a definition is not otherwise provided, "alkenyl group" refers to a linear or branched saturated monovalent hydrocarbon group including at least one carbon-carbon double bond (e.g., an ethenyl group).

As used herein, when a definition is not otherwise provided, "alkoxy group" may refer to an alkyl group that is linked via an oxygen, e.g., a methoxy group, an ethoxy group, and a sec-butyloxy group.

As used herein, when a definition is not otherwise provided, "aryl group" refers to a monovalent functional group formed by the removal of one hydrogen atom from one a ring of an arene, e.g., phenyl or naphthyl. The arene refers to a hydrocarbon having an aromatic ring, and includes monocyclic and polycyclic hydrocarbons wherein the additional ring(s) of the polycyclic hydrocarbon may be aromatic or nonaromatic.

As used herein, when a definition is not otherwise provided, "heterocyclic group" is a higher concept of a heteroaryl group, and may include at least one heteroatom selected from N, O, S, Se, Te, P and Si, and the remaining carbon. When the heterocyclic group is a fused ring, the entire heterocyclic group or each ring may include one or more heteroatoms.

As used herein, when a definition is not otherwise provided, "aromatic ring" refers to a functional group in which all ring-forming atoms in the functional group have a p-orbital, and wherein these p-orbitals are conjugated. For example, the aromatic ring may be a C6 to C20 aryl group or C3 (e.g., C4 or C5) to C20 heteroaryl group.

Hereinafter, when a definition is not otherwise provided, the energy level is the highest occupied molecular orbital (HOMO) energy level or the lowest unoccupied molecular orbital (LUMO) energy level.

It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

While the term "same," "equal" or "identical" may be used in description of some example embodiments, it should be understood that some imprecisions may exist. Thus, when one element is referred to as being the same as another element, it should be understood that an element or a value is the same as another element within a desired manufacturing or operational tolerance range (e.g., ±10%).

When the terms "about" or "substantially" are used in this specification in connection with a numerical value, it is intended that the associated numerical value includes a manufacturing or operational tolerance (e.g., ±10%) around the stated numerical value. Moreover, when the words "about" and "substantially" are used in connection with geometric shapes, it is intended that precision of the geometric shape is not required but that latitude for the shape is within the scope of the inventive concepts. Further, regardless of whether numerical values or shapes are modified as "about" or "substantially," it will be understood that these values and shapes should be construed as including a manufacturing or operational tolerance (e.g., ±10%) around the stated numerical values or shapes. When ranges are specified, the range includes all values therebetween such as increments of 0.1%.

Hereinafter, when a definition is not otherwise provided, a work function or an energy level is expressed as an absolute value from a vacuum level. In addition, when the work function or the energy level is referred to be deep, high, or large, it may have a large absolute value based on "0 eV" of the vacuum level while when the work function or the energy level is referred to be shallow, low, or small, it may have a small absolute value based on "0 eV" of the vacuum level. Further, the differences between the work function and/or the energy level may be values obtained by subtracting a small value of the absolute value from a large value of the absolute value.

Hereinafter, when a definition is not otherwise provided, the HOMO energy level may be evaluated with an amount of photoelectrons emitted by energy when irradiating UV light to a thin film using AC-2 (Hitachi) or AC-3 (Riken Keiki Co., Ltd.).

Hereinafter, when a definition is not otherwise provided, the LUMO energy level may be obtained by obtaining a bandgap energy using a UV-Vis spectrometer (Shimadzu Corporation), and then calculating the LUMO energy level from the bandgap energy and the already measured HOMO energy level.

Hereinafter, an organic compound according to some example embodiments is described.

The organic compound according to some example embodiments may include at least one electron donating group (D) and at least one electron accepting group (A).

For example, the organic compound may have a D-A structure including an electron donating group and an electron accepting group, an A-D-A structure in which electron accepting groups are disposed on both sides (e.g., opposite sides) of an electron donating group, or a D-A-D structure in which electron donating groups are disposed on both sides (e.g., opposite sides) of an electron accepting group, but is not limited thereto.

As an example, the organic compound may have an A-D-A structure in which electron accepting groups (A) are disposed on both sides (e.g., opposite sides) of an electron donating group (D) as a center, and may be represented by Chemical Formula 1.

[Chemical Formula 1]

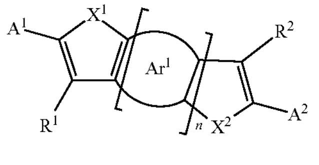

In Chemical Formula 1, $X^1$ and $X^2$ may each independently be a chalcogen element (e.g., one of O, S, Se, or Te), $Ar^1$ may be a substituted or unsubstituted C6 to C30 aromatic ring, and n is 0 or 1, $R^1$ and $R^2$ may each independently be hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, and $A^1$ and $A^2$ may each independently be an electron accepting group.

The organic compound represented by Chemical Formula 1 may be a fused polycyclic aromatic compound including a fused polycyclic aromatic ring in which two or more rings are fused with each other, as a core. The fused polycyclic aromatic ring may have a structure in which pentagonal heterocycles at both (e.g., opposite) ends and an aromatic ring between the pentagonal heterocycles are fused. The pentagonal heterocycle may be a heterocycle including a chalcogen atom, and the aromatic ring may include an aromatic hydrocarbon ring and/or a heteroaromatic ring.

The fused polycyclic aromatic ring may have electron donating characteristics by including a heterocycle having a chalcogen element. The fused polycyclic aromatic ring may be, for example, a fused ring fused with two or more rings, for example, fused with 2 to 8, 2 to 6, or 2 to 4 rings.

For example, $X^1$ and $X^2$ may be the same as or different from each other, and may each independently be O, S, Se, or Te. For example, $X^1$ and $X^2$ may each be independently one of O, S, Se, or Te.

For example, at least one of $X^1$ or $X^2$ may be S.

For example, each of $X^1$ and $X^2$ may be S.

For example, at least one of $X^1$ or $X^2$ may be Se or Te.

For example, each of $X^1$ and $X^2$ may be Se.

For example, one of $X^1$ or $X^2$ may be S or Se, and the other may be Te.

For example, $Ar^1$ may be a substituted or unsubstituted benzene, a substituted or unsubstituted naphthalene, a substituted or unsubstituted anthracene, a substituted or unsubstituted phenanthrene, a substituted or unsubstituted tetracene, a substituted or unsubstituted furan, a substituted or unsubstituted thiophene, a substituted or unsubstituted selenophene, a substituted or unsubstituted tellurophene, or a fused ring of two or more therefrom.

For example, $Ar^1$ may be one of the substituted or unsubstituted rings (e.g., one ring of a plurality of substituted or unsubstituted rings) listed in Group 1, but is not limited thereto.

[Group 1]

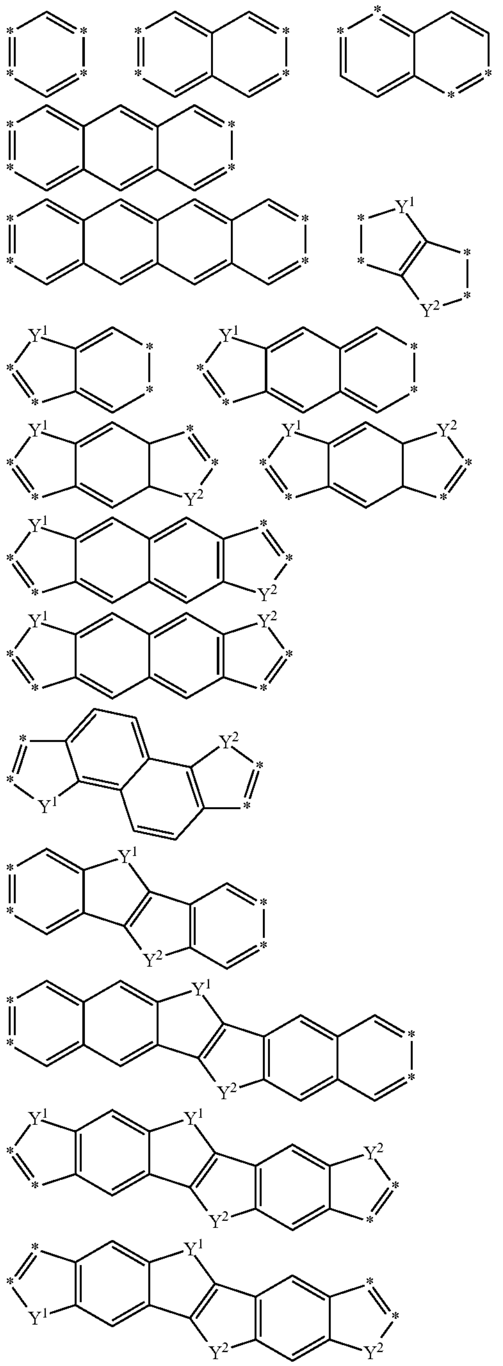

In Group 1, $Y^1$ and $Y^2$ may each independently be a chalcogen element of O, S, Se, or Te, and

* is a linking point with (e.g., within) Chemical Formula 1.

At least one hydrogen of the ring listed in Group 1 may be substituted with, for example a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof.

For example, $A^1$ and $A^2$ may be electron accepting groups having electron accepting characteristics, and the electron accepting groups may be, for example, represented by Chemical Formula 1A, 1B, or 1C, respectively. For example, $A^1$ and $A^2$ of Chemical Formula 1 may each independently be an electron accepting group represented by Chemical Formula 1A, 1B, or 1C.

[Chemical Formula 1A]

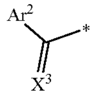

[Chemical Formula 1B]

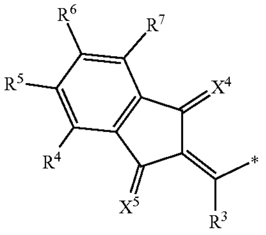

[Chemical Formula 1C]

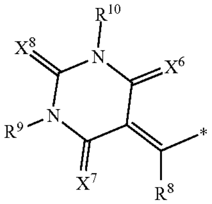

In Chemical Formula 1A, 1B, and/or 1C, $X^3$ to $X^8$ may each independently be a chalcogen element (e.g., $X^3$ to $X^8$ may each be independently one of O, S, Se, or Te), $Ar^2$ may be a C6 to C30 aryl group substituted with at least one halogen, at least one C1 to C30 haloalkyl group, at least one cyano group, at least one dicyanovinyl group, or any combination thereof; a C3 to C30 heterocyclic group substituted with at least one halogen, at least one C1 to C30 haloalkyl group, at least one cyano group, at least one dicyanovinyl group, or any combination thereof; or any combination thereof, $R^3$ to $R^{10}$ may each independently be hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, $R^4$ to $R^7$ may each independently be present or two adjacent ones thereof may be linked to form a ring, and

* may be a linking point with (e.g., within) Chemical Formula 1.

For example, $A^1$ and $A^2$ may be the same. For example, $A^1$ and $A^2$ may each be an electron accepting group represented by Chemical Formula 1A. For example, $A^1$ and $A^2$ may each be an electron accepting group represented by Chemical Formula 1B. For example, $A^1$ and $A^2$ may each be an electron accepting group represented by Chemical Formula 1C.

For example, $A^1$ and $A^2$ may be different from each other, and may each independently be selected from Chemical Formula 1A, 1B, or 1C.

For example, at least one of $A^1$ or $A^2$ may be an electron accepting group represented by Chemical Formula 1A, and for example, $A^1$ and $A^2$ may each be an electron accepting group represented by Chemical Formula 1A.

$Ar^2$ of Chemical Formula 1A may be, for example, a halogen-substituted phenyl group; a halogen-substituted naphthyl group; a halogen-substituted anthracenyl group; a halogen-substituted phenanthrenyl group; a phenyl group substituted with a C1 to C30 haloalkyl group; a naphthyl group substituted with a C1 to C30 haloalkyl group; an anthracenyl group substituted with a C1 to C30 haloalkyl group; a phenanthrenyl group substituted with a C1 to C30 haloalkyl group; a phenyl group substituted with a cyano group; a naphthyl group substituted with a cyano group; an anthracenyl group substituted with a cyano group; a phenanthrenyl group substituted with a cyano group; a phenyl group substituted with a dicyanovinyl group; a naphthyl group substituted with a dicyanovinyl group; an anthracenyl group substituted with a dicyanovinyl group; a phenanthrenyl group substituted with a dicyanovinyl group; or any combination thereof. Herein, the phenyl group, naphthyl group, anthracenyl group, or phenanthrenyl group may be substituted with 1 to 5 halogens, C1 to C30 haloalkyl groups, cyano groups, or dicyanovinyl groups, but is not limited thereto.

$X^3$ in Chemical Formula 1A may be, for example, O, S, Se, or Te. For example, $X^3$ of Chemical Formula 1A may be different from $X^1$ and $X^2$ of Chemical Formula 1. For example, $X^1$ and $X^2$ of Chemical Formula 1 may each independently be S, Se, or Te, and $X^3$ of Chemical Formula 1A may be O.

For example, at least one of $A^1$ or $A^2$ may be an electron accepting group represented by Chemical Formula 1B, and for example, $A^1$ and $A^2$ may each be an electron accepting group represented by Chemical Formula 1B.

$X^4$ and $X^5$ of Chemical Formula 1B may be the same as or different from each other, and may be, for example, O, S, Se or Te. For example, $X^4$ and $X^5$ of Chemical Formula 1B may be different from $X^1$ and $X^2$ of Chemical Formula 1. For example, $X^1$ and $X^2$ of Chemical Formula 1 may each independently be S, Se, or Te, and $X^4$ and $X^5$ of Chemical Formula 1B may each be O.

$R^3$ in Chemical Formula 1B may be, for example, hydrogen or a substituted or unsubstituted C1 to C30 alkyl group, for example hydrogen.

$R^4$ to $R^7$ in Chemical Formula 1B may each independently be present or, for example, adjacent two may be linked to form benzene, naphthalene, anthracene, or phenanthrene.

For example, at least one of $A^1$ or $A^2$ may be an electron accepting group represented by Chemical Formula 1C, and for example, $A^1$ and $A^2$ may each be an electron accepting group represented by Chemical Formula 1C.

$X^6$, $X^7$, and $X^8$ of Chemical Formula 1C may be the same as or different from each other, and may be, for example, O, S, Se, or Te. However, when $X^6$ and $X^7$ are each O, $X^8$ may be O, Se, or Te and $X^8$ may not be S. For example, $X^6$, $X^7$, and $X^8$ of Chemical Formula 1C may be different from $X^1$ and $X^2$ of Chemical Formula 1, and for example, $X^1$ and $X^2$ of Chemical Formula 1 may each independently be S, Se, or Te, and $X^6$, $X^7$, and $X^8$ of Chemical Formula 1A may each be O.

$R^8$ in Chemical Formula 1C may be, for example, hydrogen or a substituted or unsubstituted C1 to C30 alkyl group, for example hydrogen.

$R^9$ and $R^{10}$ in Chemical Formula 1C may be, for example, hydrogen, a, substituted or unsubstituted C1 to C30 alkyl group, a substituted or unsubstituted C2 to C30 alkenyl group, or a substituted or unsubstituted C6 to C30 aryl group.

While $A^1$ and $A^2$ may each independently be an electron accepting group represented by Chemical Formula 1A, 1B, or 1C, example embodiments are not limited thereto.

For example, in some example embodiments, $A^1$ and $A^2$ may each be independently an electron accepting group other than an electron accepting group represented by Chemical Formula 1A, 1B, or 1C. For example, in some example embodiments, $A^1$ and $A^2$ may each be independently an electron accepting group that may include a halogen (e.g., F, Cl, Br, or I), a nitrile group (e.g., *—CN, where * is a linking point with Chemical Formula 1), a carbonyl group (e.g., *—(C═O)R, where * is a linking point with Chemical Formula 1 and R is hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, or any combination thereof), a nitro group (e.g., *—$NO_2$, where * is a linking point with Chemical Formula 1), or the like.

The organic compound may be, for example, represented by one of Chemical Formulas 1A-1 to 1C-4, but is not limited thereto.

[Chemical Formula 1A-1]

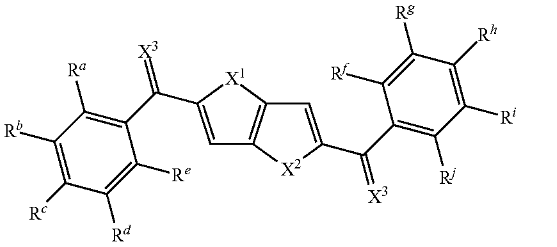

[Chemical Formula 1A-2]

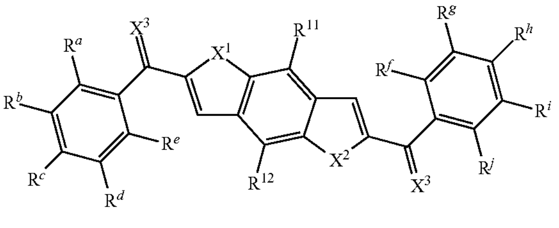

-continued

[Chemical Formula 1A-3]

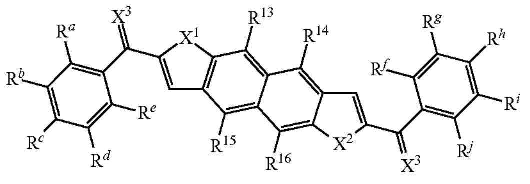

[Chemical Formula 1A-4]

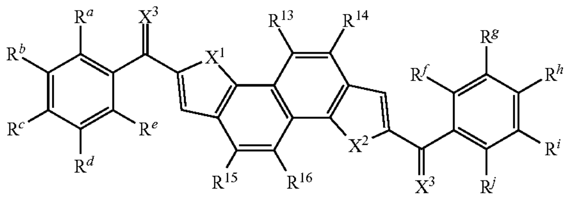

[Chemical Formula 1B-1]

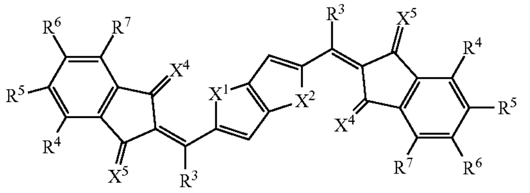

[Chemical Formula 1B-2]

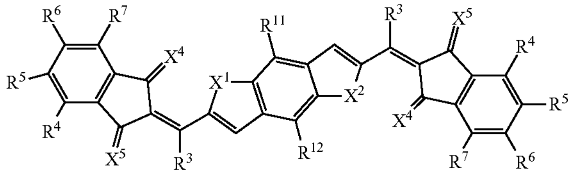

[Chemical Formula 1B-3]

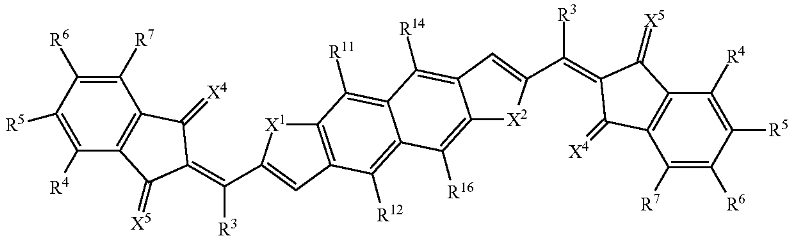

[Chemical Formula 1B-4]

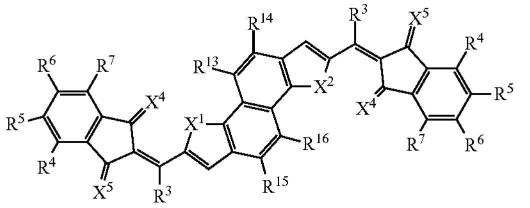

[Chemical Formula 1C-1]

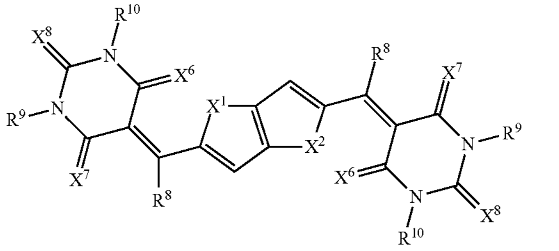

[Chemical Formula 1C-2]

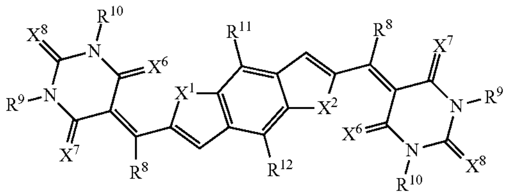

[Chemical Formula 1C-3]

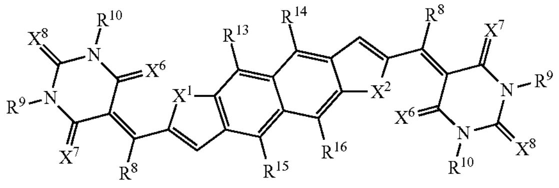

[Chemical Formula 1C-4]

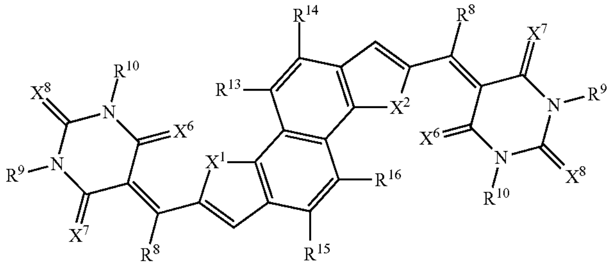

In Chemical Formulas 1A-1 to 1C-4, $X^1$ to $X^8$ and $R^3$ to $R^{16}$ may be the same as described above, for example $X^1$ to $X^8$ may each independently be a chalcogen element, such that when $X^6$ and $X^7$ are each O, $X^8$ is not S (e.g., is one of O, Se, or Te), and $R^3$ to $R^{16}$ may each independently be hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, $R^a$ to $R^j$ may each independently be hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, a dicyanovinyl group, or any combination thereof, at least one of $R^a$ to $R^e$ may be a halogen, a C1 to C30 haloalkyl group, a cyano group, a dicyanovinyl group, or any combination thereof, and at least one of $R^f$ to $R^j$ may be a halogen, a C1 to C30 haloalkyl group, a cyano group, a dicyanovinyl group, or any combination thereof.

For example, one of $R^a$ to $R^e$ may be a halogen, a C1 to C30 haloalkyl group, a cyano group, a dicyanovinyl group, or any combination thereof, and the other four of $R^a$ to $R^e$ may be hydrogen, a substituted or unsubstituted C1 to C30 alkyl group, a substituted or unsubstituted C6 to C30 aryl group, or any combination thereof.

For example, one of $R^f$ to $R^j$ may be a halogen, a C1 to C30 haloalkyl group, a cyano group, a dicyanovinyl group, or any combination thereof, and the other four of $R^f$ to $R^j$ may be hydrogen, a substituted or unsubstituted C1 to C30 alkyl group, a substituted or unsubstituted C6 to C30 aryl group or any combination thereof.

For example, two of $R^a$ to $R^e$ may be halogen, a C1 to C30 haloalkyl group, a cyano group, a dicyanovinyl group, or any combination thereof, and the other three of $R^a$ to $R^e$ may be hydrogen, a substituted or unsubstituted C1 to C30 alkyl group, a substituted or unsubstituted C6 to C30 aryl group, or any combination thereof.

For example, two of $R^f$ to $R^j$ may be halogen, a C1 to C30 haloalkyl group, a cyano group, a dicyanovinyl group, or any combination thereof, and the other three of $R^f$ to $R^j$ may be hydrogen, a substituted or unsubstituted C1 to C30 alkyl group, a substituted or unsubstituted C6 to C30 aryl group, or any combination thereof.

For example, three of $R^a$ to $R^e$ may be halogen, a C1 to C30 haloalkyl group, a cyano group, a dicyanovinyl group, or any combination thereof, and the other two of $R^a$ to $R^e$ may be hydrogen, a substituted or unsubstituted C1 to C30 alkyl group, a substituted or unsubstituted C6 to C30 aryl group, or any combination thereof.

For example, three of $R^f$ to $R^j$ may be halogen, a C1 to C30 haloalkyl group, a cyano group, a dicyanovinyl group, or any combination thereof, and the other two of $R^f$ to $R^j$ may be hydrogen, a substituted or unsubstituted C1 to C30 alkyl group, a substituted or unsubstituted C6 to C30 aryl group, or any combination thereof.

For example, four of $R^a$ to $R^e$ may be halogen, a C1 to C30 haloalkyl group, a cyano group, a dicyanovinyl group, or any combination thereof, and the other one (e.g., another one) of $R^a$ to $R^e$ may be hydrogen, a substituted or unsubstituted C1 to C30 alkyl group, a substituted or unsubstituted C6 to C30 aryl group, or any combination thereof.

For example, four of $R^f$ to $R^j$ may be halogen, a C1 to C30 haloalkyl group, a cyano group, a dicyanovinyl group, or any combination thereof, and the other one (e.g., another one) of $R^f$ to $R^j$ may be hydrogen, a substituted or unsubstituted C1 to C30 alkyl group, a substituted or, unsubstituted C6 to C30 aryl group, or any combination thereof.

For example, each of $R^a$ to $R^e$ may be a halogen, a C1 to C30 haloalkyl group, a cyano group, a dicyanovinyl group, or any combination thereof.

For example, each of $R^f$ to $R^j$ may be a halogen, a C1 to C30 haloalkyl group, a cyano group, a dicyanovinyl group, or any combination thereof.

For example, each of $R^a$ to $R^e$ may be a halogen, a C1 to C30 haloalkyl group, a cyano group, a dicyanovinyl group, or any combination thereof, and each of $R^f$ to $R^j$ may be a halogen, a C1 to C30 haloalkyl group, a cyano group, a dicyanovinyl group, or any combination thereof.

For example, adjacent two of $R^a$ to $R^e$ may be linked to form a ring.

For example, adjacent two of $R^f$ to $R^j$ may be linked to form a ring.

In some example embodiments, the organic compound may have a D-A-D structure in which electron donating groups (D) are disposed on both sides (e.g., opposite sides) of an electron accepting group (A) as a center. The electron accepting group may include, for example, a carbonyl group (e.g., a ketone group, a carboxylate ester group, an amide group, or the like), for example represented by formula R—(C═O)—R', where R and R' each include (e.g., consist or comprise) respective electronic donating groups which may the same or different from each other. The electron donating groups (D) that are disposed on both sides (e.g., opposite sides) of the electron accepting group (A) may be the same or different from each other and may independently include, for example, a fused polycyclic aromatic ring in which two or more rings are fused with each other, as a core. The fused polycyclic aromatic ring may have a structure in which pentagonal heterocycles at both (e.g., opposite) ends and an aromatic ring between the pentagonal heterocycles are fused. The pentagonal heterocycle may be a heterocycle including a chalcogen atom, and the aromatic ring may include an aromatic hydrocarbon ring and/or a heteroaromatic ring. The fused polycyclic aromatic ring may have electron donating characteristics by including a heterocycle having a chalcogen element. The fused polycyclic aromatic ring may be, for example, a fused ring fused with two or more rings, for example, fused with 2 to 8, 2 to 6, or 2 to 4 rings.

For example, the organic compound may have a D-A-D structure in which electron donating groups (D) are disposed on both sides (e.g., opposite sides) of an electron accepting group (A) as a center, and may be represented by Chemical Formula 3.

$$D1\text{-}A1\text{-}D2 \qquad \text{[Chemical Formula 3]}$$

In Chemical Formula 3, D1 and D2 may each independently be an electron donating group represented by Chemical Formula 3A.

[Chemical Formula 3A]

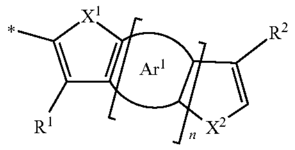

In Chemical Formula 3A, $X^1$ and $X^2$ may each independently be a chalcogen element (e.g., one of O, S, Se, or Te), $Ar^1$ may be a substituted or unsubstituted C6 to C30 aromatic ring, and n is 0 or 1, $R^1$ and $R^2$ may each independently be hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, and

* is a linking point with (e.g., within) Chemical Formula 3.

In Chemical Formula 3, A1 may include an electron accepting group.

In some example embodiments, A1 may be represented by Chemical Formula 3B, 3C, or 3D,

[Chemical Formula 3B]

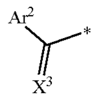

[Chemical Formula 3C]

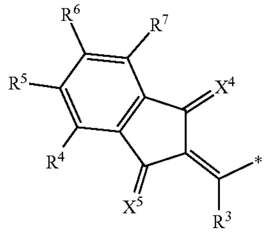

[Chemical Formula 3D]

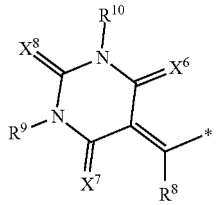

wherein, in Chemical Formula 3B, 3C, and/or 3D,

* is a linking point with D1, $X^3$ to $X^8$ are each independently a chalcogen element, and when $X^6$ and $X^7$ are each O, $X^8$ is not S, $Ar^2$ is a group including a C6 to C30 aryl group substituted with at least one halogen, at least one C1 to C30 haloalkyl group, at least one cyano group, at least one dicyanovinyl group, or any combination thereof; a C3 to C30 heterocyclic group substituted with at least one halogen, at least one C1 to C30 haloalkyl group, at least one cyano group, at least one dicyanovinyl group, or any combination thereof; or any combination thereof, wherein one hydrogen of the group is substituted with a linking point with D2, $R^3$ to $R^{10}$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, a linking point with D2, or any combination thereof, wherein one of $R^3$ to $R^7$ and one of $R^8$ to $R^{10}$ include the linking point with D2, and $R^4$ to $R^7$ are each independently present or two adjacent ones of $R^4$ to $R^7$ are linked to each other to form a ring.

In some example embodiments, A1 may include an electron accepting group that is or includes a carbonyl group (e.g., *—R—(C═O)—R'—*, *—R—(C═O)—*, *—(C═O)—R'—*, or *—(C═O)—*, where *'s are linking points with respective ones of D1 or D2, and R and R' are each independently a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, or any combination thereof).

The organic compound may have semiconductor characteristics by having an electron donating group and an electron accepting group of the aforementioned structures, and may be used, for example, as an n-type semiconductor. For example, the LUMO energy level of the organic compound may be about 2.5 eV to about 4.5 eV (absolute value), and within the above range, about 2.6 eV to about 4.3 eV, about 2.6 eV to about 4.0 eV, or about 2.8 eV to about 3.8 eV. For example, the bandgap energy of the organic compound may be about 2.0 eV to about 3.5 eV, and within the above range, about 2.2 eV to about 3.3 eV.

The organic compound may be a material that may be vacuum-deposited, and may be, for example, a sublimable material that may be vacuum-deposited by sublimation without decomposition or polymerization in a particular (or, alternatively, predetermined) temperature range. The sublimable material may be identified by thermogravimetric analysis (TGA). It may be an organic material that lose a weight with increasing-temperature and for example lose a weight by at least about 50% of an initial weight thereof, without substantial decomposition or polymerization.

For example, the organic compound may have a temperature (hereinafter referred to as a "sublimation temperature") at which a weight reduction of 10% relative to the initial weight thereof occurs during thermogravimetric analysis at a pressure of about 10 Pa or less within a particular (or, alternatively, predetermined) range. For example, the sublimation temperature of the organic compound may be less than or equal to about 380° C., within the above range, less than or equal to about 370° C., less than or equal to about 360° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., less than or equal to about 250° C.; about 100° C. to about 380° C., about 100° C. to about 370° C., about 100° C. to about 360° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 360° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

The organic compound may be applied to various devices due to the aforementioned electrical and thermal properties.

For example, the organic compound may be applied to a sensor. The sensor may be a light absorption sensor configured to absorb light and convert the light into an electrical signal. The sensor may be an organic sensor including an organic material as a photoelectric conversion material. The organic compound, when included in a sensor, such as in a photoelectric conversion layer that includes the photoelectric conversion material, may cause the photoelectric conversion layer, and thus the sensor (e.g., photoelectric conversion device) to exhibit improved photoelectric conversion efficiency in a particular wavelength spectrum (e.g., improved photoelectric conversion efficiency in a green wavelength spectrum and in addition, higher photoelectric conversion efficiency at a green wavelength than at a blue wavelength or a red wavelength and thus high wavelength selectivity). In addition, the organic compound, when included in a sensor, such as in a photoelectric conversion layer that includes the photoelectric conversion material, may cause the photoelectric conversion layer, and thus the sensor (e.g., photoelectric conversion device) to exhibit a reduced dark current when a reverse bias is applied thereto. As a result, a performance of a sensor (e.g., photoelectric conversion device) may be improved based on the sensor including the organic compound (e.g., including the organic compound within the photoelectric conversion layer of a photoelectric conversion device).

FIG. 1 is a cross-sectional view showing an example of a sensor according to some example embodiments.

Referring to FIG. 1, a sensor 100 according to some example embodiments includes a first electrode 110, a second electrode 120, a photoelectric conversion layer 130, and optionally first and second common auxiliary layers 140 and 150.

A substrate (not shown) may be under the first electrode 110 or on the second electrode 120. The substrate may be for example an inorganic substrate such as a glass plate or silicon wafer, or an organic substrate made of an organic material such as polycarbonate, polymethylmethacrylate, polyethyleneterephthalate, polyethylenenaphthalate, polyamide, polyethersulfone, or any combination thereof. The substrate may be omitted.

The substrate may be, for example, a semiconductor substrate, or a silicon substrate. The semiconductor substrate may include a circuit unit (not shown) including for example circuitry, and the circuit unit (e.g., circuitry) may include transmission transistors (not shown) and/or charge storage (not shown) integrated in the semiconductor substrate. The circuit unit may be electrically connected to the first electrode 110 or the second electrode 120.

One of the first electrode 110 or the second electrode 120 may be an anode and the other may be a cathode. For example, the first electrode 110 may be an anode and the second electrode 120 may be a cathode. For example, the first electrode 110 may be a cathode and the second electrode 120 may be an anode.

At least one of the first electrode 110 or the second electrode 120 may be a light-transmitting electrode. The light-transmitting electrode may be a transparent electrode or a semi-transmissive electrode. The transparent electrode may have a light transmittance of greater than or equal to about 85%, greater than or equal to about 90%, or greater than or equal to about 95% and the semi-transmissive electrode may have a light transmittance of greater than or equal to about 30% and less than about 85%, about 40% to about 80%, or about 40% to about 75%. The transparent electrode and the semi-transmissive electrode may include, for example, at least one of an oxide conductor, a carbon conductor, or a metal thin film. The oxide conductors may include, for example, one or more selected from indium tin oxide (ITO), indium zinc oxide (IZO), zinc tin oxide (ZTO), aluminum tin oxide (ATO), and aluminum zinc oxide (AZO), the carbon conductor may include one or more selected from graphene and carbon nanostructures, and the metal thin film may be a very thin film including aluminum (Al), magnesium (Mg), silver (Ag), gold (Au), magnesium-silver (Mg—Ag), magnesium-aluminum (Mg—Al), an alloy thereof, or any combination thereof.

Any one of the first electrode 110 or the second electrode 120 may be a reflective electrode. The reflective electrode may include a reflective layer having a light transmittance of less than or equal to about 5% and/or a reflectance of greater than or equal to about 80%, and the reflective layer may include an optically opaque material. The optically opaque material may include a metal, a metal nitride, or any combination thereof, for example silver (Ag), copper (Cu), aluminum (Al), gold (Au), titanium (Ti), chromium (Cr), nickel (Ni), an alloy thereof, a nitride thereof (e.g., TiN), or any combination thereof, but is not limited thereto. The reflective electrode may comprise (e.g., may be formed of) a reflective layer or may have a stacked structure of a reflective layer/transmissive layer or a transmissive layer/reflective layer/transmissive layer, and the reflective layer may be one layer or two or more layers.

For example, each of the first electrode 110 and the second electrode 120 may be a light-transmitting electrode, and any one of the first electrode 110 or the second electrode 120 may be a light-receiving electrode disposed at the light receiving side.

For example, the first electrode 110 may be a light-transmitting electrode, the second electrode 120 may be a reflective electrode, and the first electrode 110 may be a light-receiving electrode.

For example, the first electrode 110 may be a reflective electrode, the second electrode 120 may be a light-transmitting electrode, and the second electrode 120 may be a light-receiving electrode.

The photoelectric conversion layer 130 may be configured to absorb light of at least some wavelength spectrum and convert the absorbed light into an electrical signal. For example, the photoelectric conversion layer 130 may be configured to convert at least a portion of light in the blue wavelength spectrum (hereinafter referred to as “blue light”), light in the green wavelength spectrum (hereinafter referred to as “green light”), light in the red wavelength spectrum (hereinafter referred to as “red light”), and light in the infrared wavelength spectrum (hereinafter referred to as “infrared light”) into an electrical signal.

For example, the photoelectric conversion layer 130 may be configured to selectively absorb any one of blue light, green light, red light, or infrared light and convert the absorbed light into an electrical signal. Herein, the selective absorption of one of blue light, green light, red light, or infrared light means that a peak absorption wavelength $\lambda_{peak}$ of an absorption spectrum is present in one of wavelength spectra of greater than or equal to about 380 nm and less than about 500 nm, about 500 nm to about 600 nm, greater than about 600 nm and less than about 750 nm, and/or greater than or equal to about 750 nm to less than about 3000 nm, and that the absorption spectrum in the corresponding wavelength spectrum is significantly higher than that of other wavelength spectra. Herein, the “significantly higher” may mean that about 70% to about 100%, about 75% to about 100%, about 80% to about 100%, about 85% to about 100%, about 90% to about 100%, or about 95% to about 100% of the total area of the absorption spectrum may belong to the corresponding wavelength spectrum.

The photoelectric conversion layer 130 may include at least one p-type semiconductor or at least one n-type semiconductor for photoelectric conversion of the absorbed light. The p-type semiconductor and the n-type semiconductor may form a pn junction, generate excitons by receiving light from the outside, and then separate the generated excitons into holes and electrons.

At least one of the p-type semiconductor or the n-type semiconductor may be a light absorbing material, and for example, each of the p-type semiconductor and the n-type semiconductor may be a light absorbing material. For example, at least one of the p-type semiconductor or the n-type semiconductor may be an organic material. For example, at least one of the p-type semiconductor or the n-type semiconductor may be a wavelength-selective light absorbing material configured to selectively absorb light in a particular (or, alternatively, predetermined) wavelength spectrum. For example, the p-type semiconductor and the n-type semiconductor may have the peak absorption wavelength $\lambda_{peak}$ in the same or different wavelength spectrum.

For example, at least one of the p-type semiconductor or the n-type semiconductor may be a light absorbing material having a peak absorption wavelength $\lambda_{peak}$ in a wavelength spectrum of greater than or equal to about 380 nm and less than about 500 nm and may be, for example, an organic light absorbing material having a peak absorption wavelength $\lambda_{peak}$ in a wavelength spectrum of about 410 nm to about 480 nm.

For example, at least one of the p-type semiconductor or the n-type semiconductor may be a light absorbing material having a peak absorption wavelength $\lambda_{peak}$ in a wavelength spectrum of about 500 nm to about 600 nm and may be, for example, an organic light absorbing material having a peak absorption wavelength $\lambda_{peak}$ in a wavelength spectrum of about 520 nm to about 580 nm.

For example, at least one of the p-type semiconductor or the n-type semiconductor may be a light absorbing material having a peak absorption wavelength $\lambda_{peak}$ in a wavelength spectrum of greater than about 600 nm and less than about 750 nm (e.g., greater than about 600 nm and less than about 700 nm) and may be, for example, an organic light absorbing material having a peak absorption wavelength $\lambda_{peak}$ in a wavelength spectrum of about 620 nm to about 680 nm.

For example, the HOMO energy level of the p-type semiconductor may be about 5.0 eV to about 6.0 eV, and within the above range, about 5.1 eV to about 5.9 eV, about 5.2 eV to about 5.8 eV, or about 5.3 eV to about 5.8 eV. For example, the LUMO energy level of the p-type semiconductor may be about 2.7 eV to about 4.3 eV, and within the above range, about 2.8 eV to about 4.1 eV or about 3.0 eV to about 4.0 eV. For example, the bandgap energy of the p-type semiconductor may be about 1.7 eV to about 2.3 eV, and within the above range, about 1.8 eV to about 2.2 eV or about 1.9 eV to about 2.1 eV.

For example, a p-type semiconductor may be an organic material having a core structure including an electron donating moiety (EDM), a π-conjugated linking moiety (LM), and an electron accepting moiety (EAM).

*EDM-LM-EAM** [Chemical Formula A]

In Chemical Formula A,

EDM may be an electron donating moiety,

EAM may be an electron accepting moiety, and

LM may be a pi conjugated linking moiety to link the electron donating moiety and the electron accepting moiety.

For example, the p-type semiconductor may be represented by Chemical Formula 2.

[Chemical Formula 2]

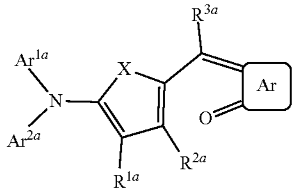

In Chemical Formula 2,

X may be O, S, Se, Te, SO, $SO_2$, $CR^bR^c$, or $SiR^dR^e$,

Ar may be a substituted or unsubstituted C6 to C30 arylene group, a substituted or unsubstituted C3 to C30 heterocyclic group, or a fused ring of two or more selected therefrom, $Ar^{1a}$ and $Ar^{2a}$ may each independently be a substituted or unsubstituted C6 to C30 aryl(ene) group or a substituted or unsubstituted C3 to C30 heteroaryl(ene) group, $R^{1a}$ to $R^{3a}$ and $R^b$ to $R^e$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, and $Ar^{1a}$, $Ar^{2a}$, $R^{1a}$, and $R^{2a}$ may each independently be present, or two adjacent ones thereof may be linked to each other to form a ring.

For example, $Ar^{1a}$ and $Ar^{2a}$ may each independently be a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, or a substituted or unsubstituted pyridopyridazinyl group.

For example, $Ar^{1a}$ and $Ar^{2a}$ may be fused to each other to form a ring.

For example, $Ar^{2a}$ and $R^{1a}$ may be fused to each other to form a ring.

Specifically, the p-type semiconductor may be represented by Chemical Formula 2A or 2B.

[Chemical Formula 2A]

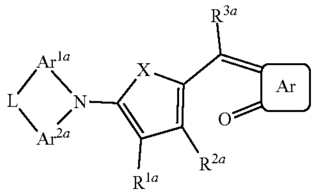

-continued

[Chemical Formula 2B]

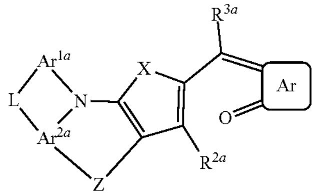

In Chemical Formulas 2A and 2B,

X may be O, S, Se, Te, SO, $SO_2$, $CR^bR^c$, or $SiR^dR^e$,

Ar may be a substituted or unsubstituted C6 to C30 arylene group, a substituted or unsubstituted C3 to C30 heterocyclic group, or a fused ring of two or more selected therefrom, $Ar^{1a}$ and $Ar^{2a}$ may each independently be a substituted or unsubstituted C6 to C30 arylene group or a substituted or unsubstituted C3 to C30 heteroarylene group, L and Z may each independently be a single bond, O, S, Se, Te, SO, $SO_2$, $CR^fR_g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and $R^{1a}$, $R^{2a}$, $R^{3a}$, and $R^b$ to $R^l$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof.

For example, the p-type semiconductor may be selected from compounds listed in Groups 2A, 2B, or 2C, but is not limited thereto.

[Group 2A]

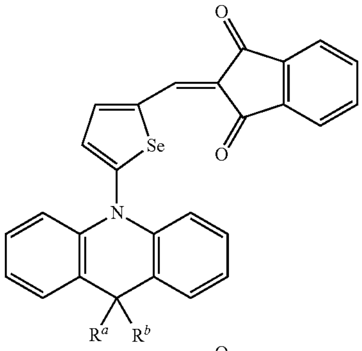

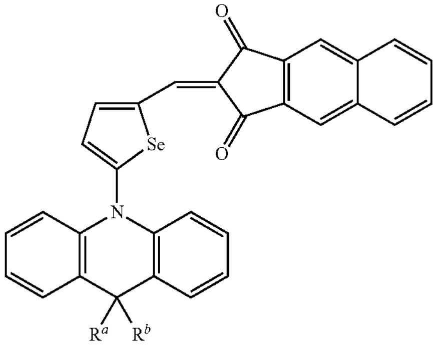

-continued

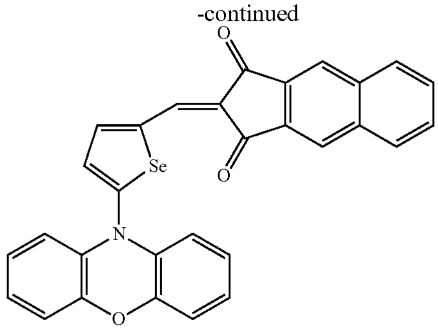

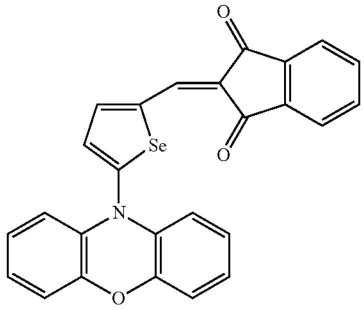

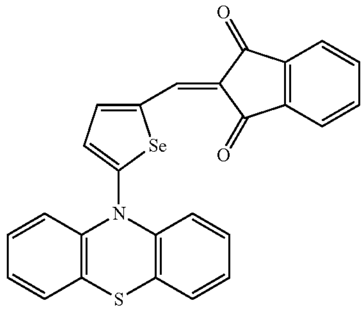

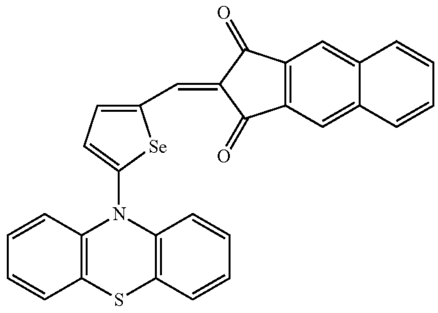

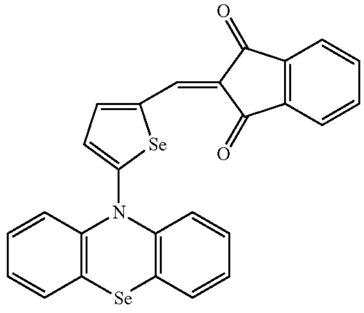

-continued
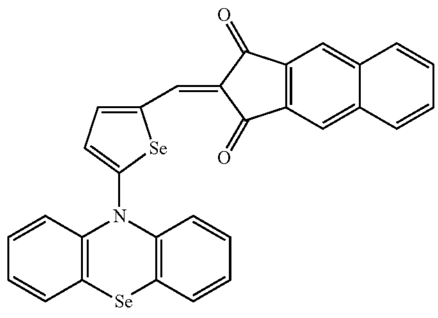
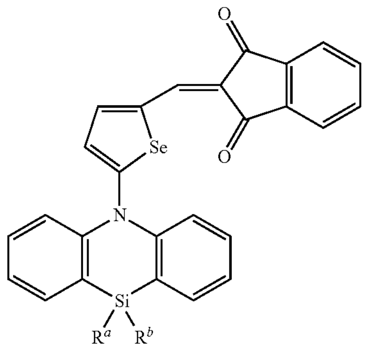
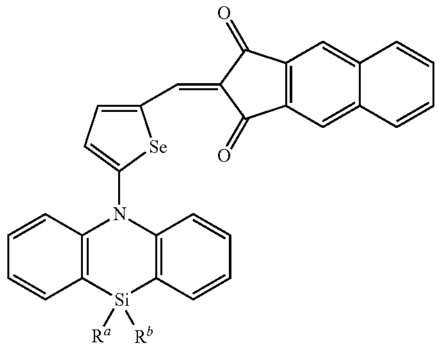
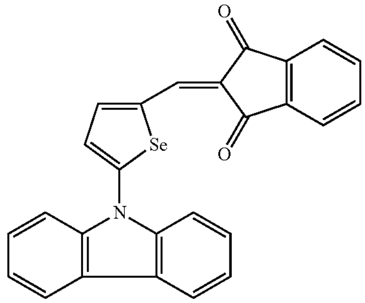
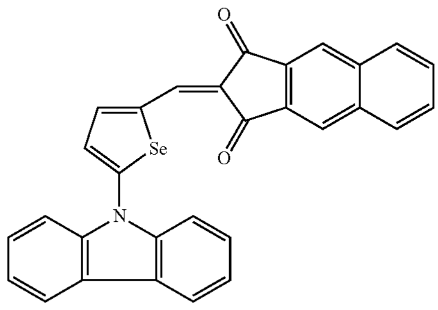
-continued
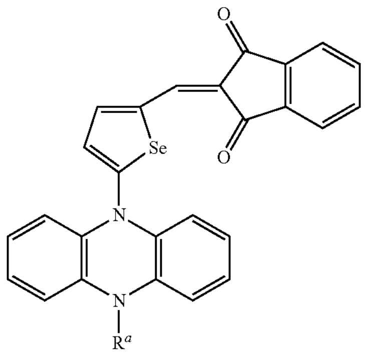
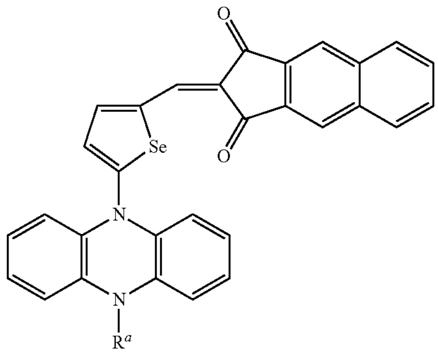
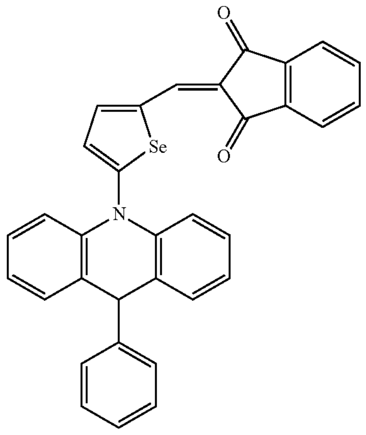
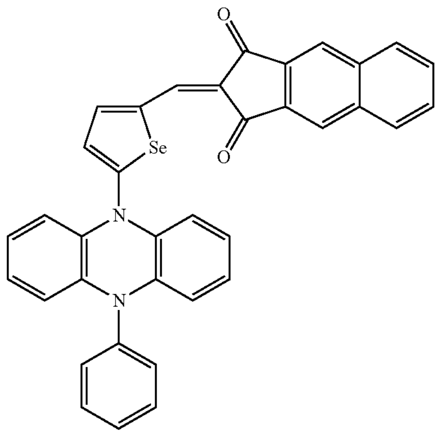

-continued
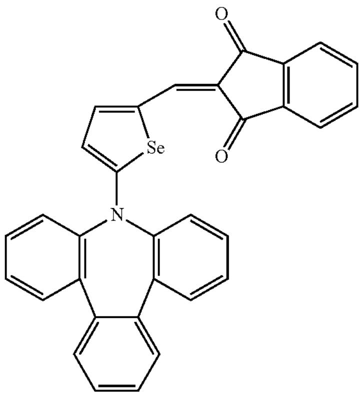
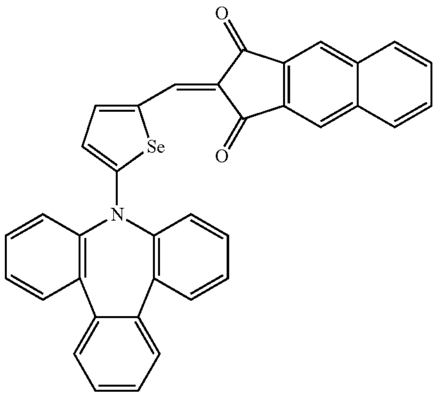
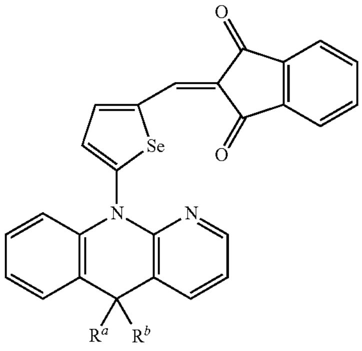
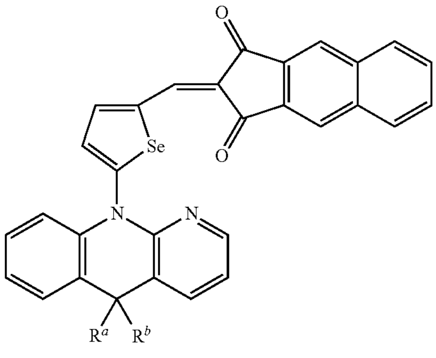
-continued
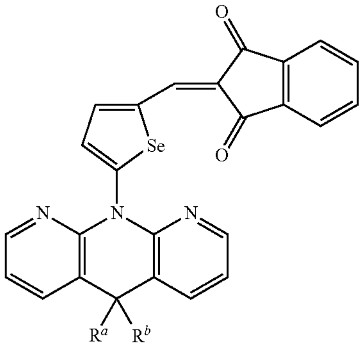
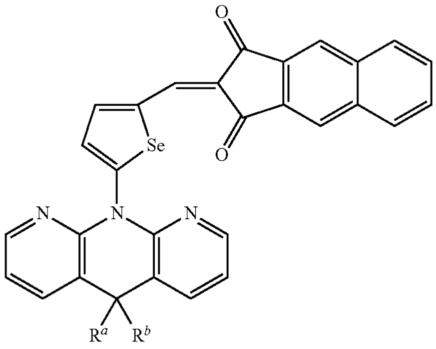
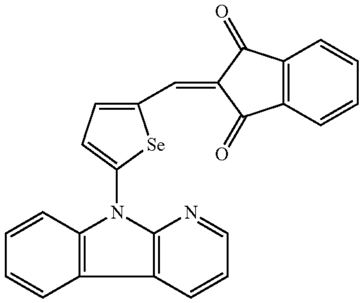
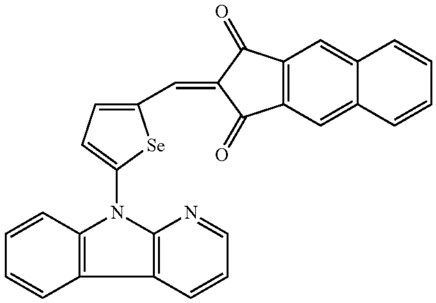
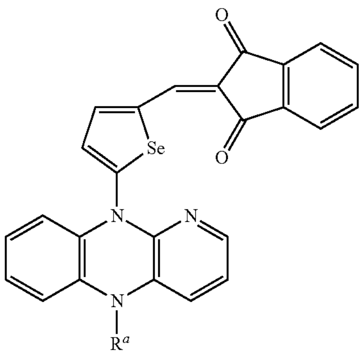

-continued
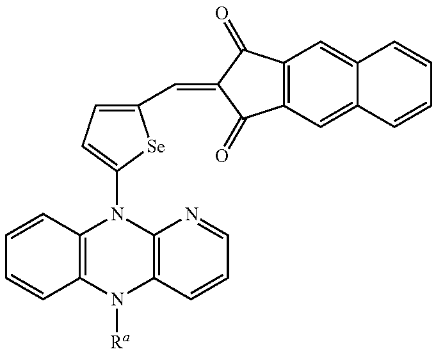
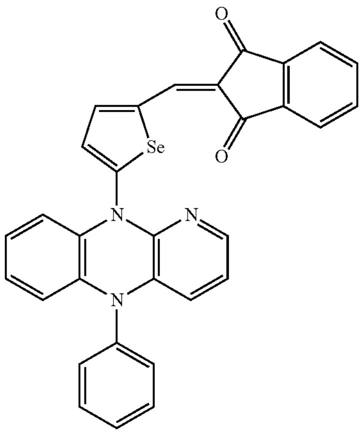
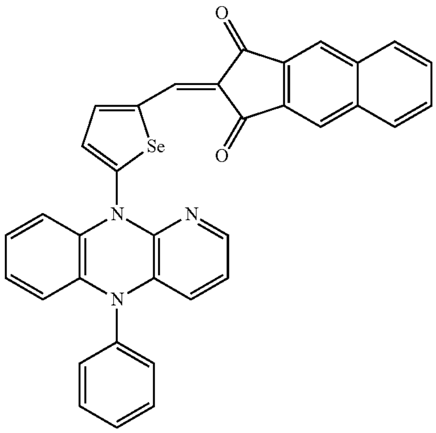
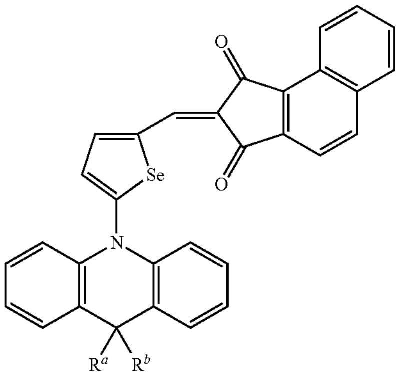
-continued
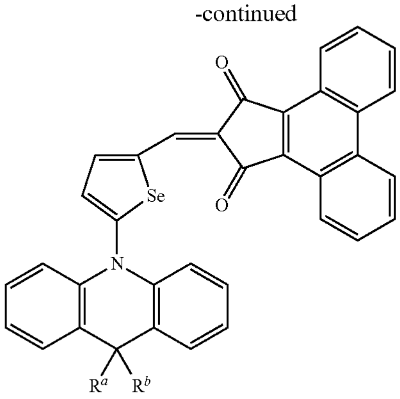
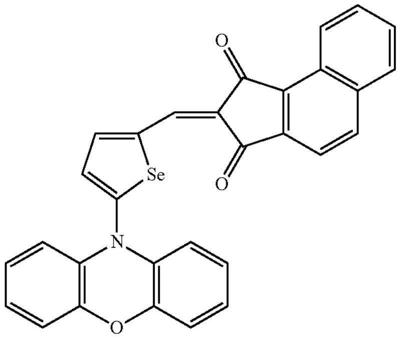
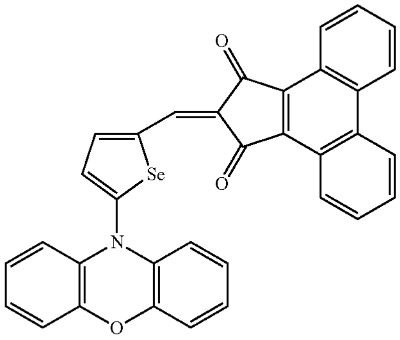
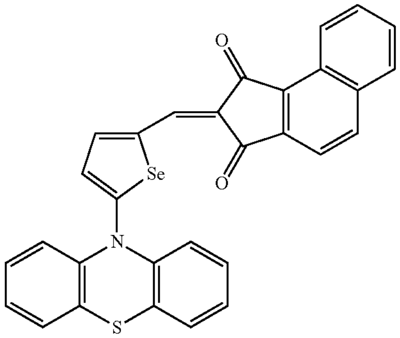
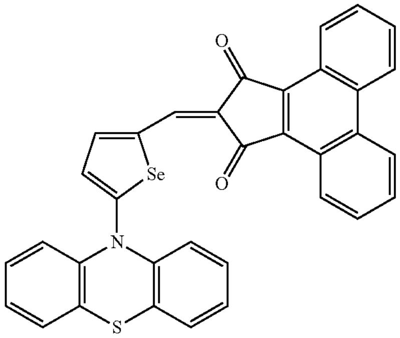

-continued
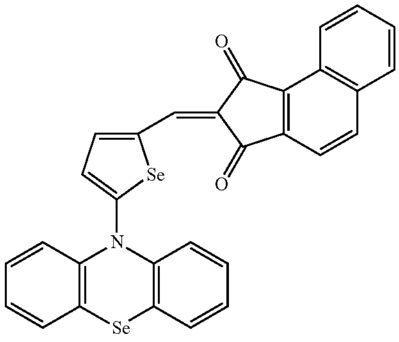
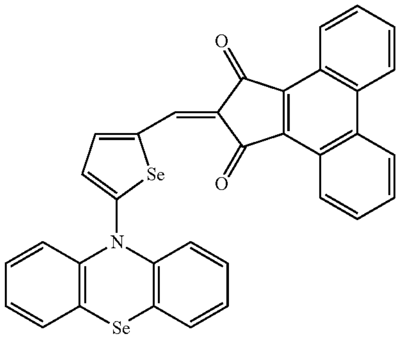
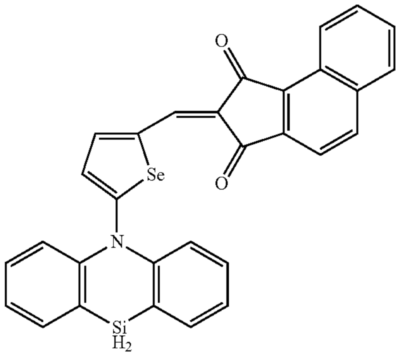
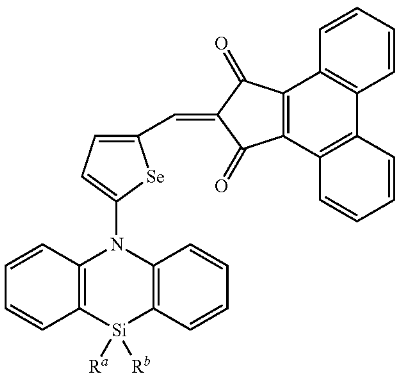
-continued
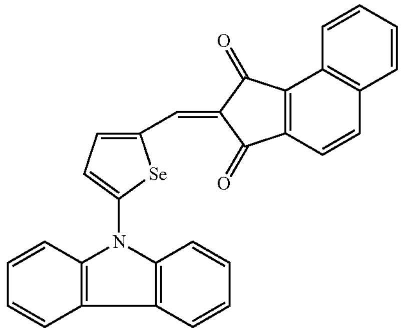
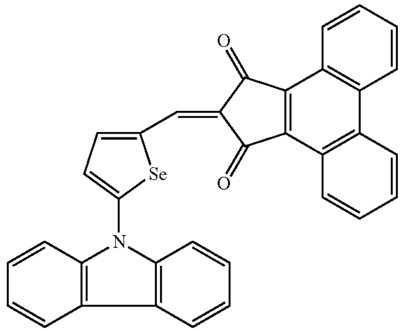
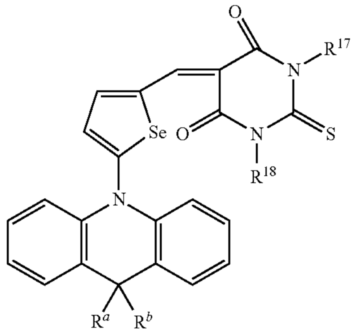
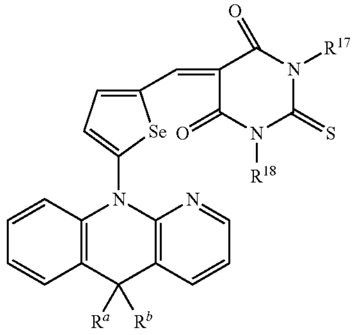
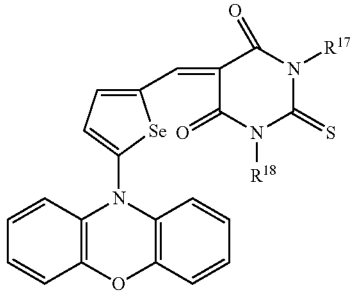

-continued
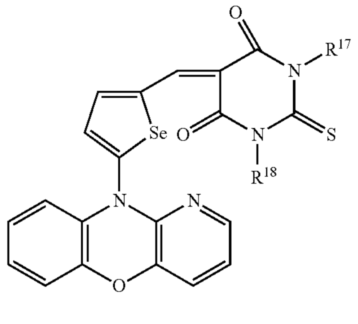
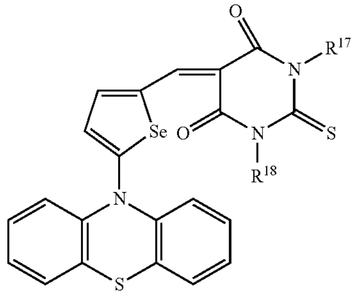
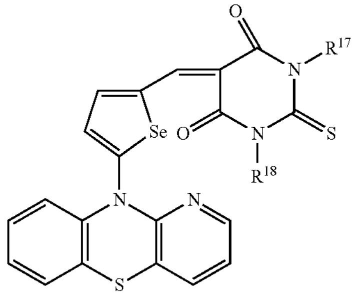
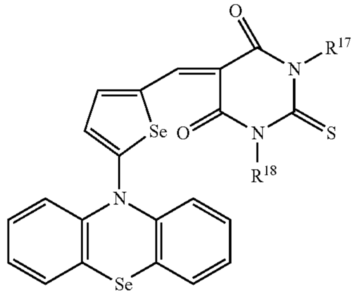
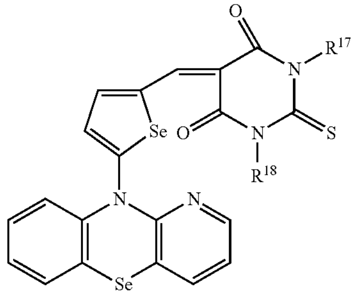
-continued
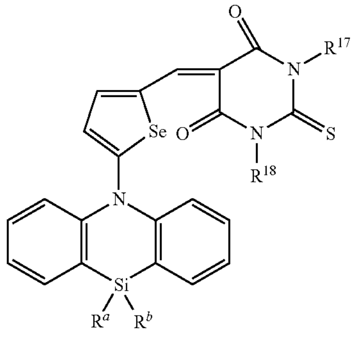
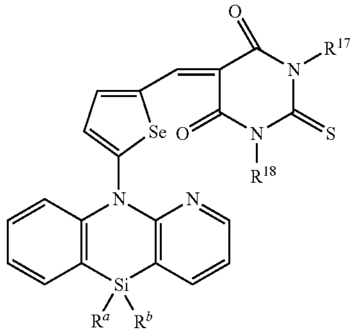
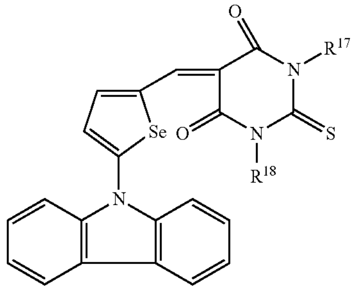
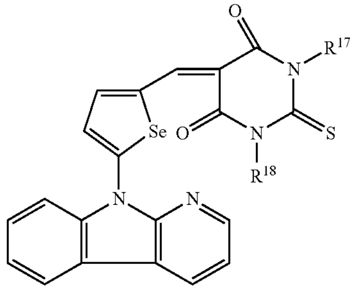
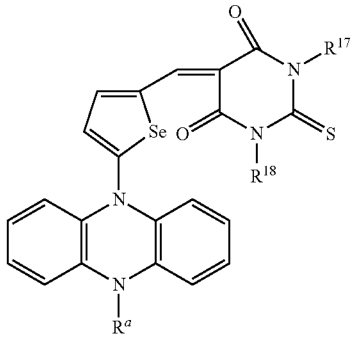

-continued
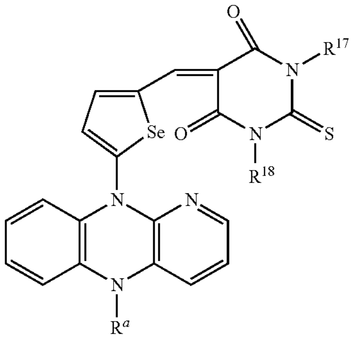
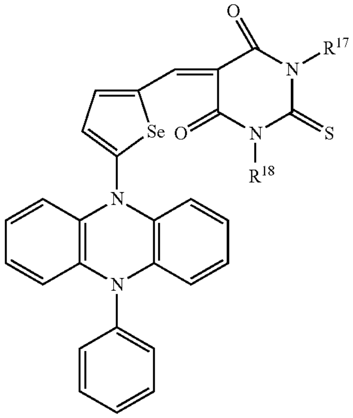
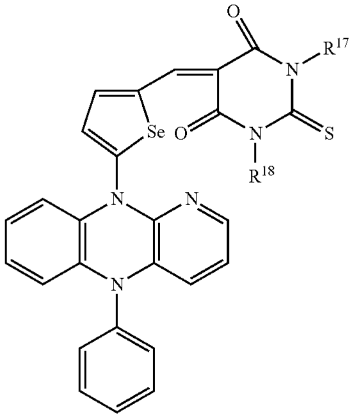
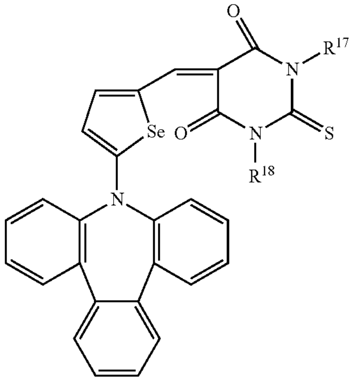
-continued
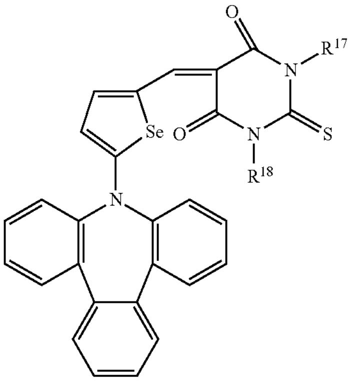
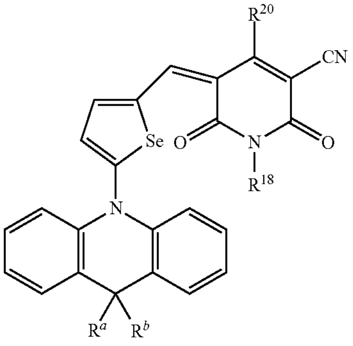
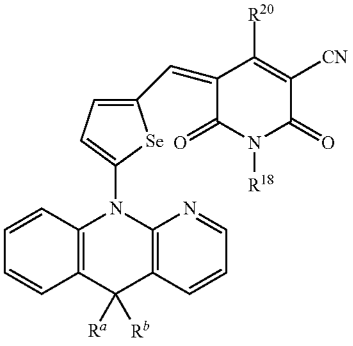
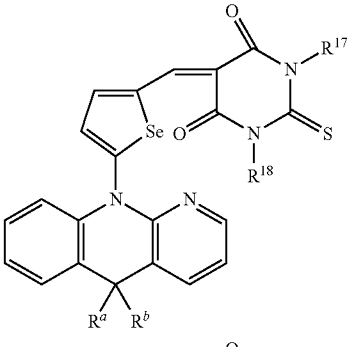
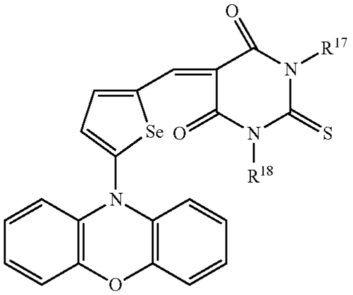

-continued
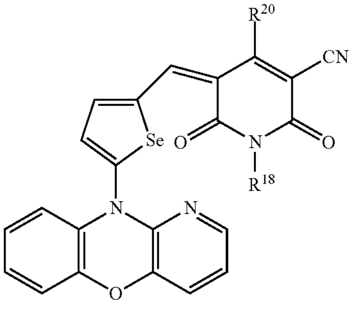
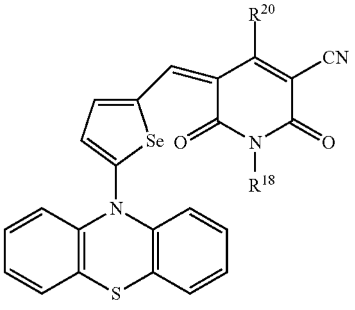
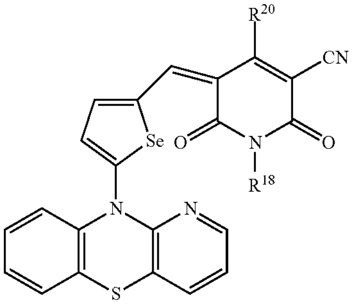
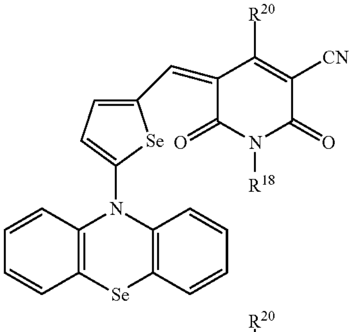
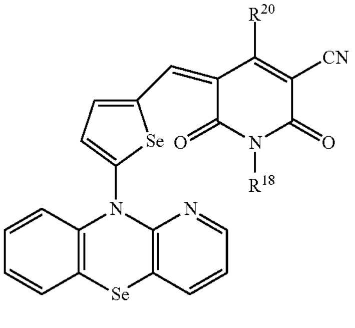
-continued
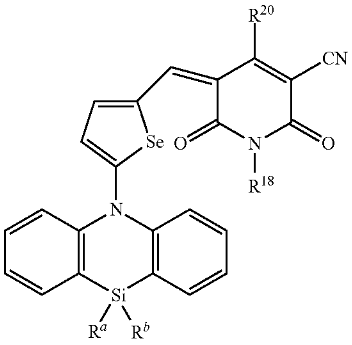
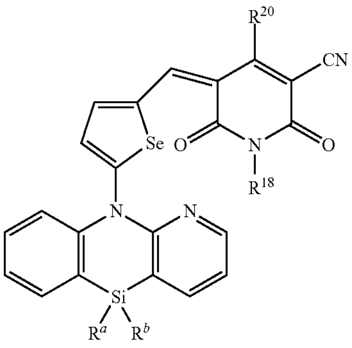
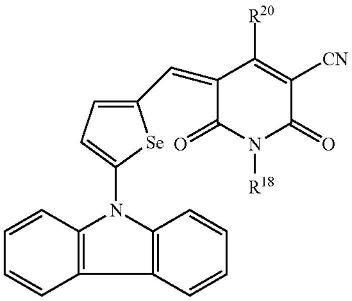
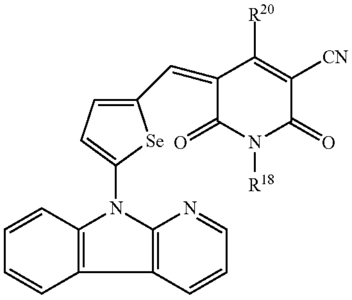
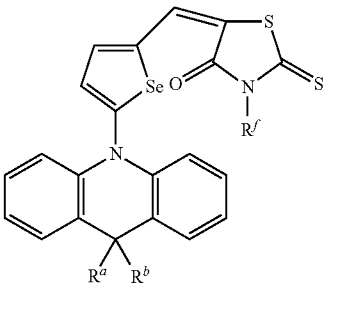

-continued

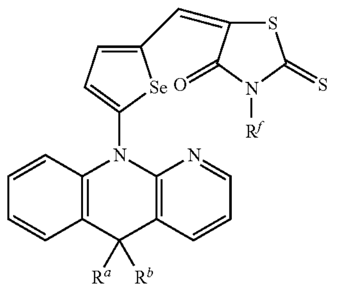

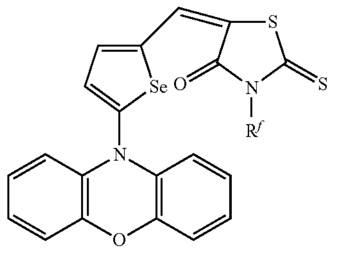

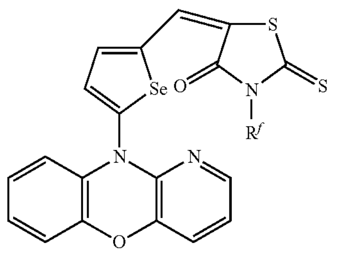

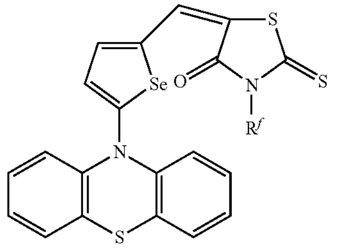

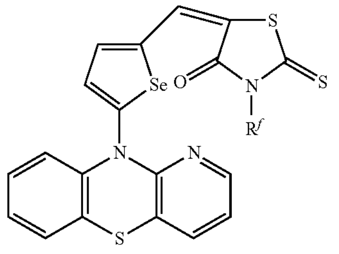

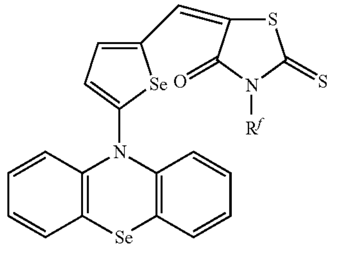

-continued

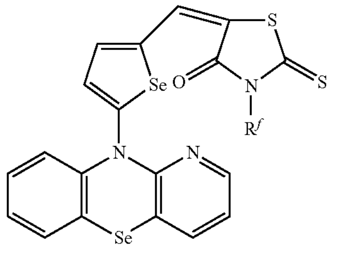

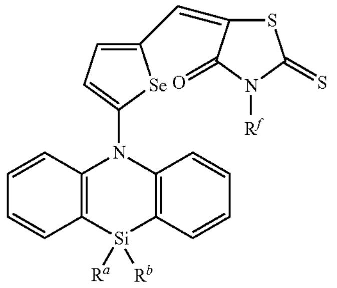

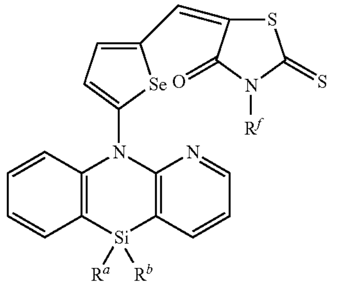

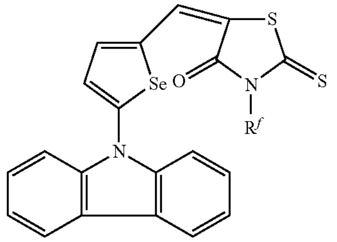

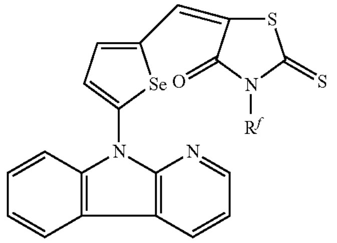

In Group 2A, one or more hydrogens present in each aromatic ring (i.e., aromatic hydrocarbon ring or heteroaromatic ring) may each be independently replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and any combination thereof, and $R^a$, $R^b$, $R^f$, $R^{16}$, $R^{17}$, $R^{18}$, and $R^{20}$ may each independently be hydrogen or a substituted or unsubstituted C1 to C6 alkyl group.

[Group 2B]
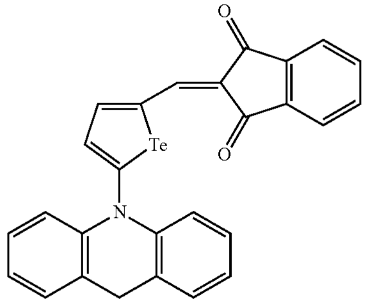
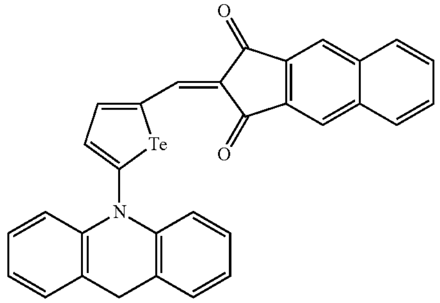
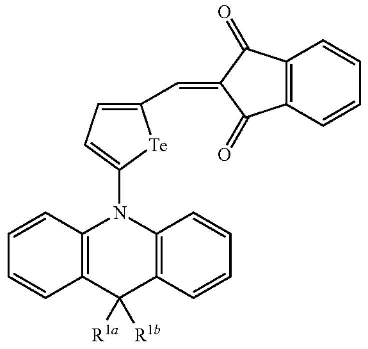
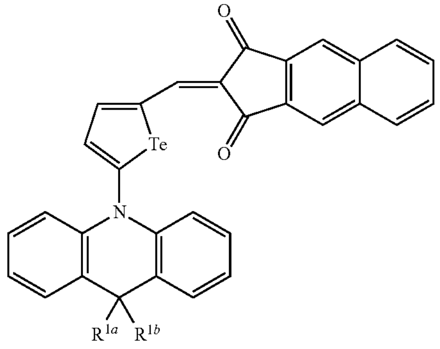
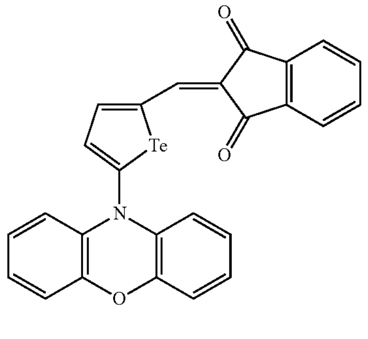
-continued
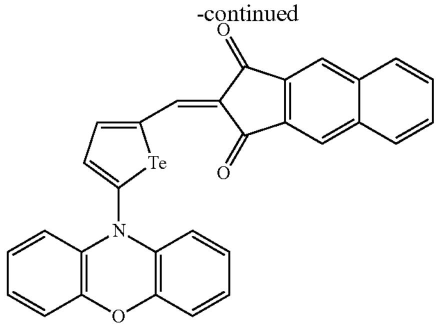
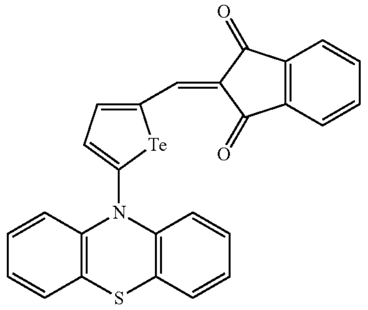
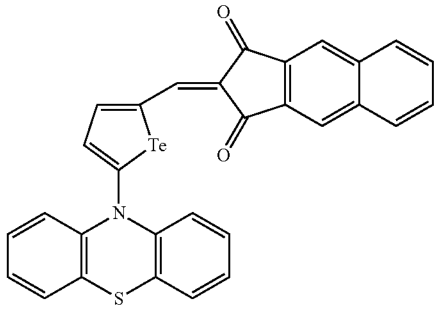
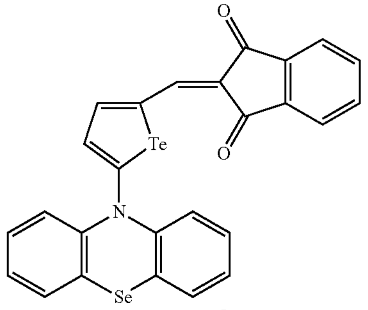
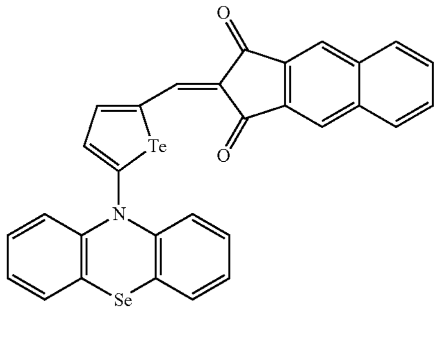

-continued
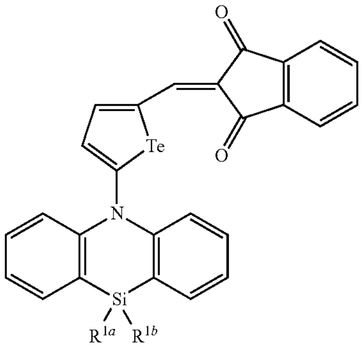
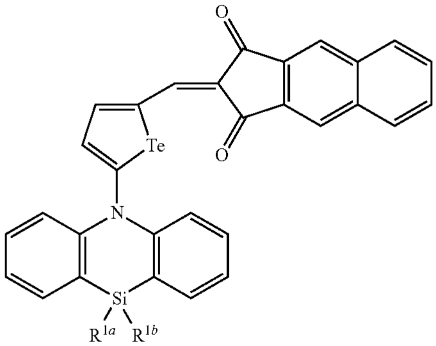
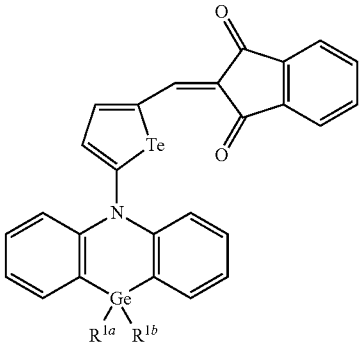
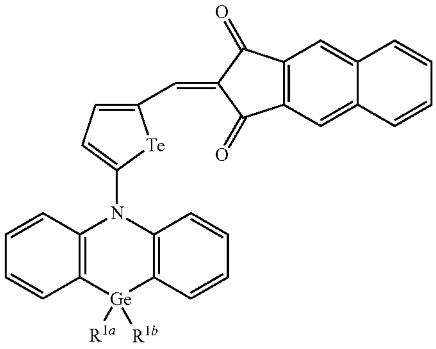
-continued
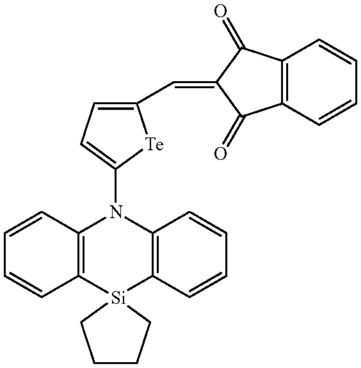
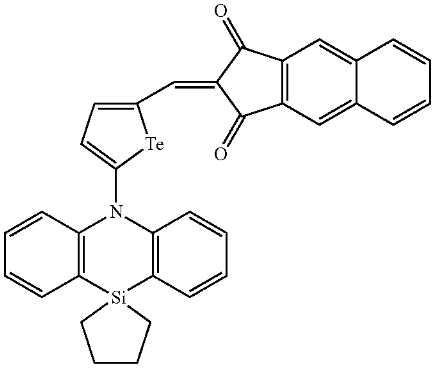
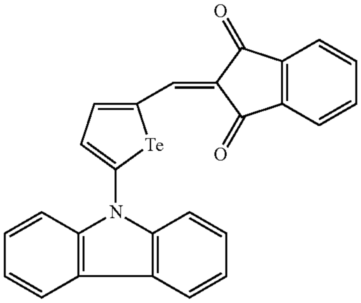
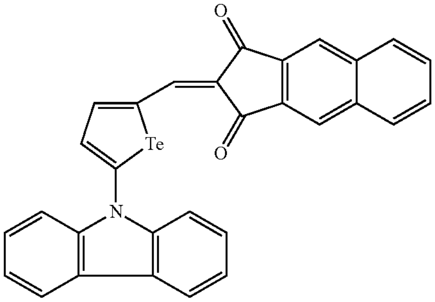
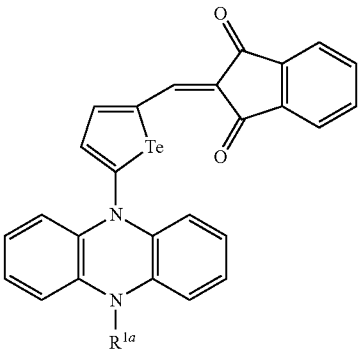

-continued
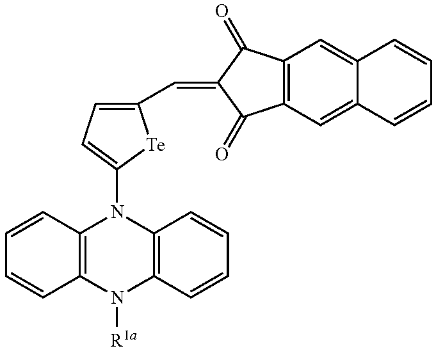
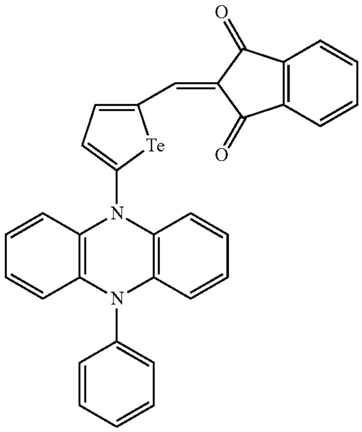
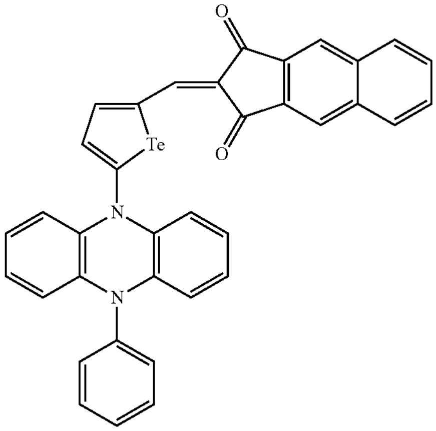
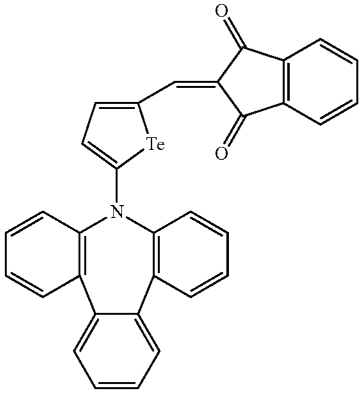
-continued
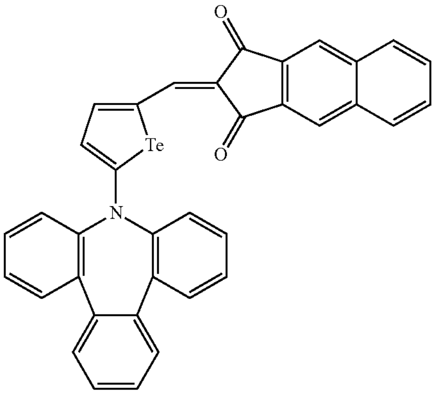
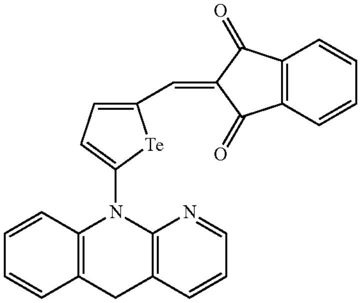
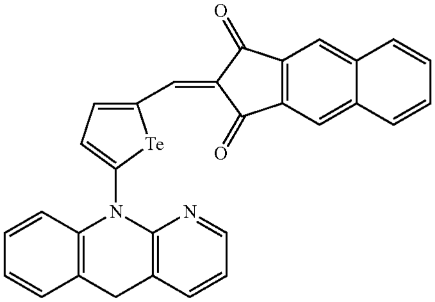
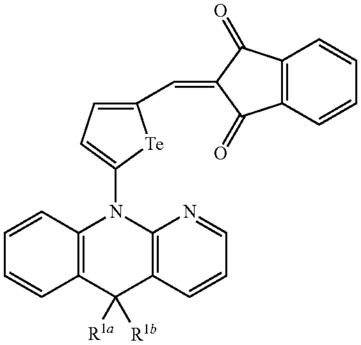
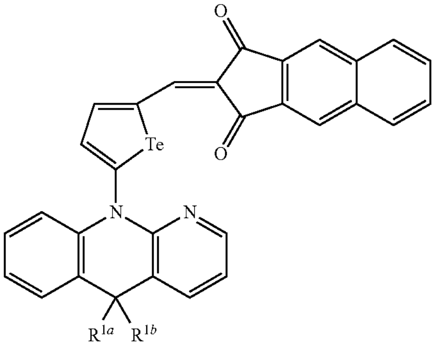

-continued
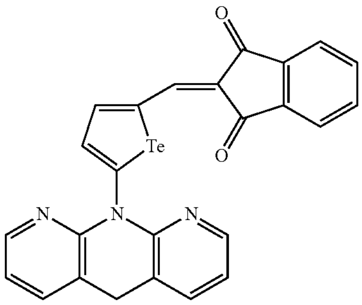
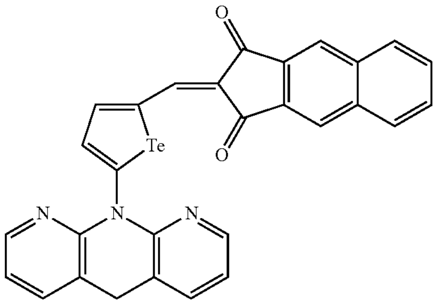
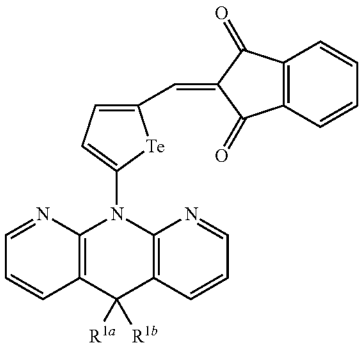
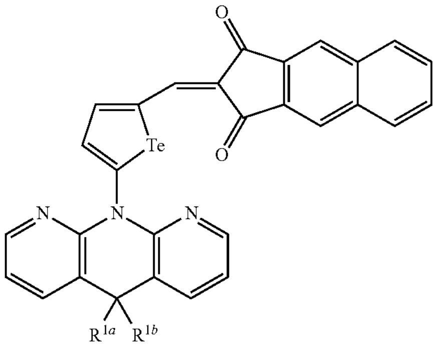
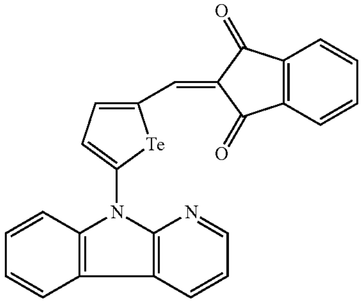
-continued
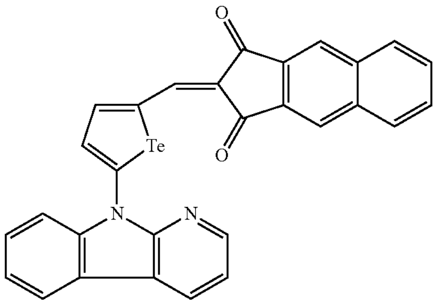
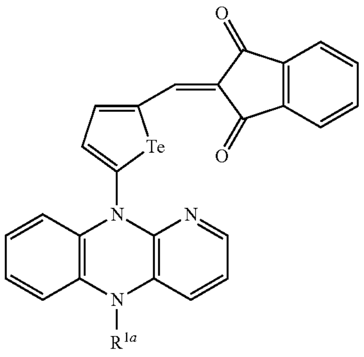
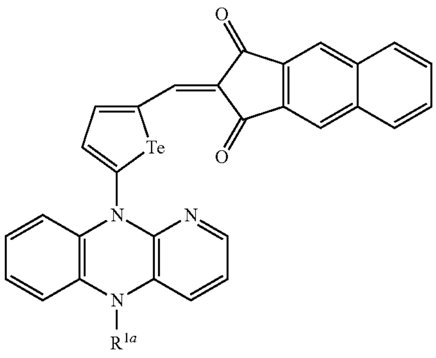
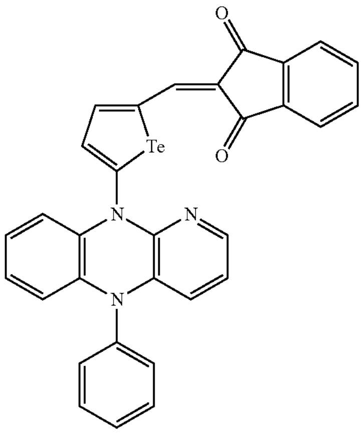

-continued
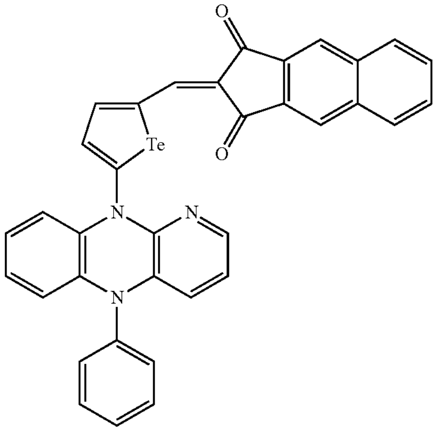
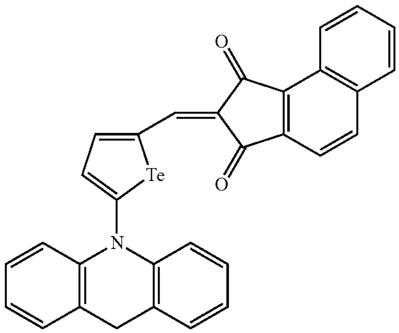
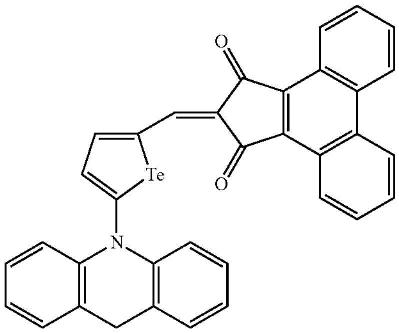
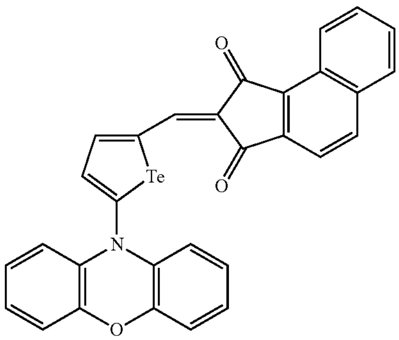
-continued
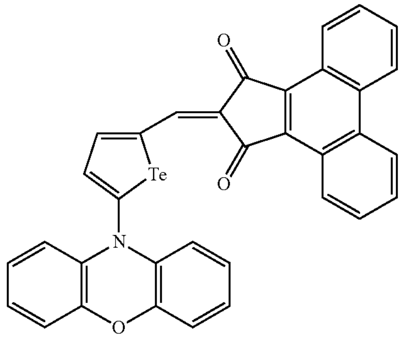
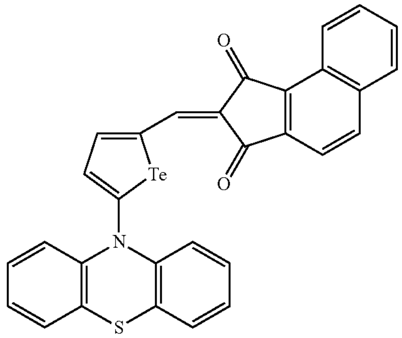
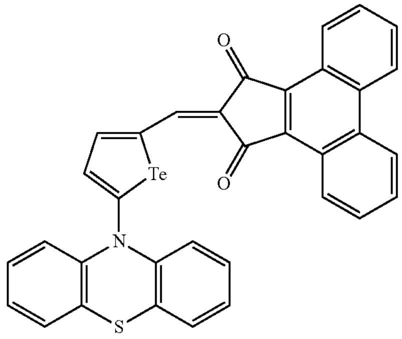
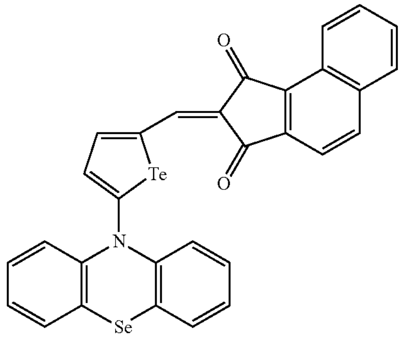
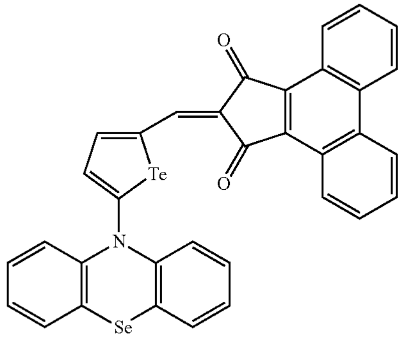

-continued
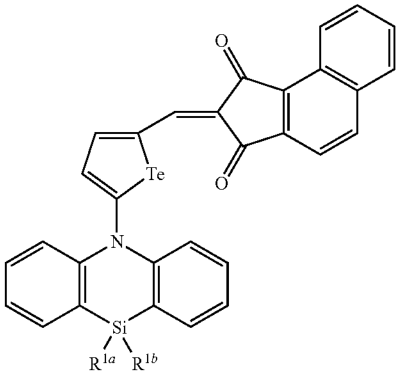
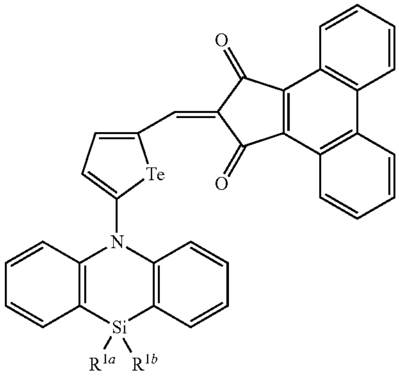
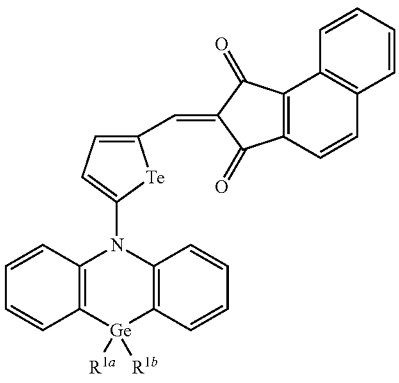
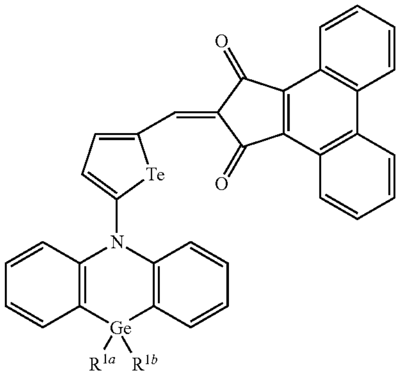
-continued
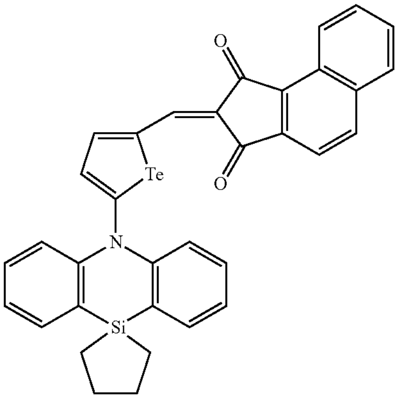
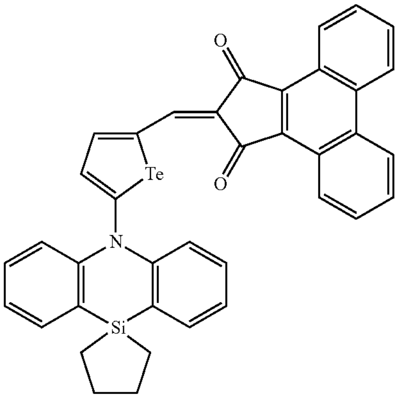
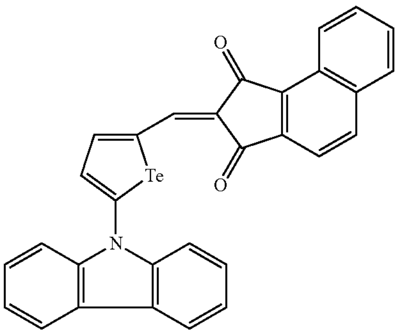
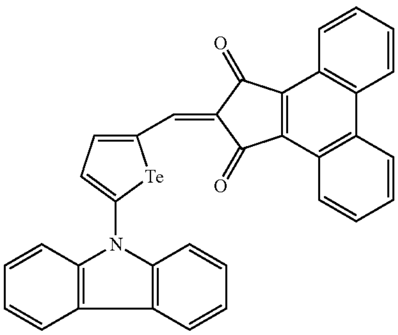

-continued
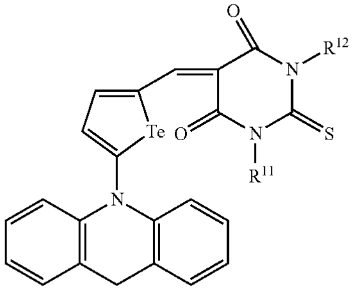
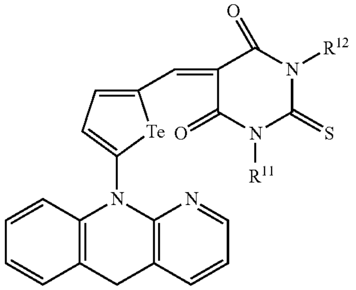
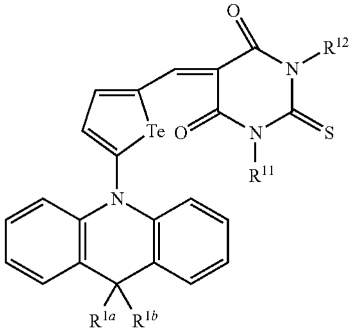
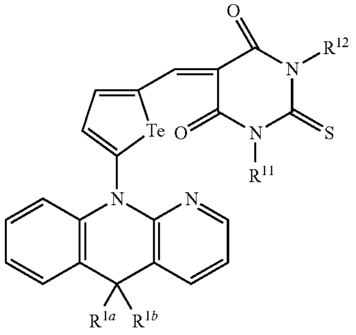
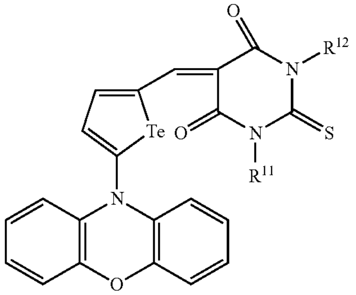
-continued
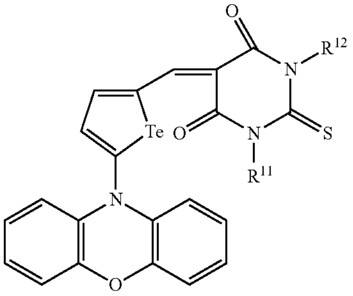
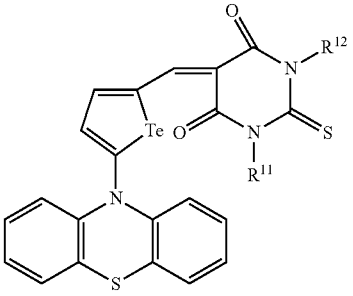
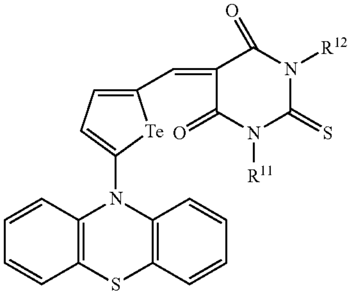
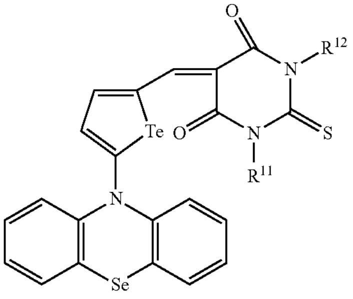
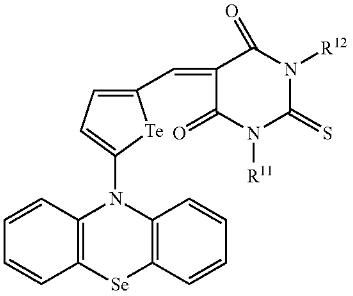

-continued
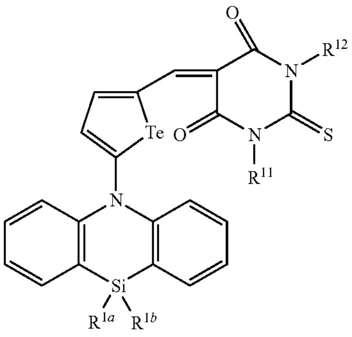
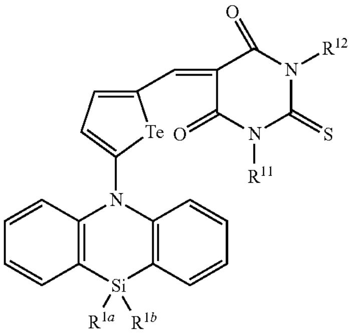
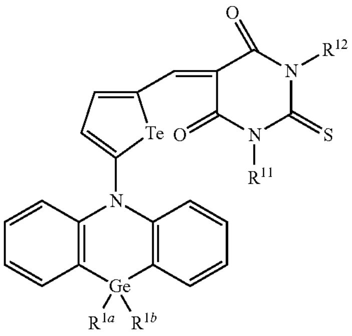
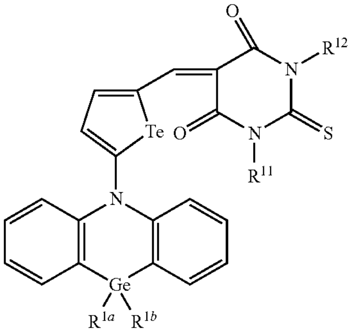
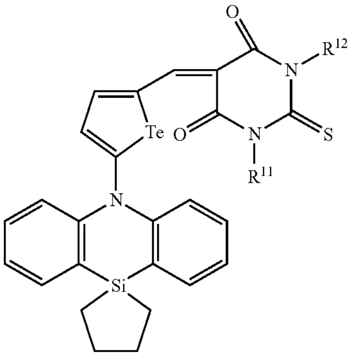
-continued
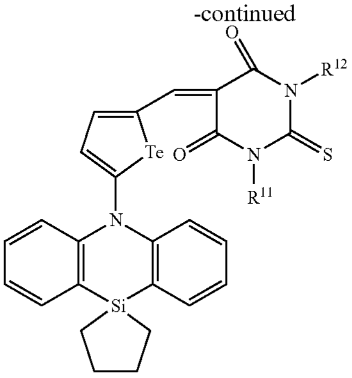
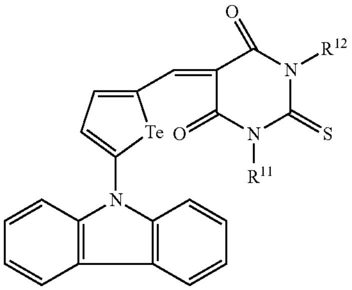
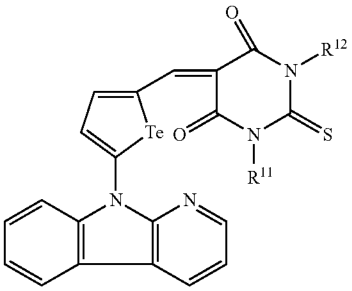
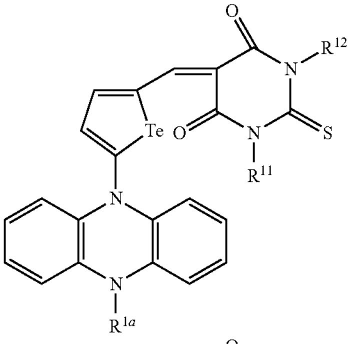
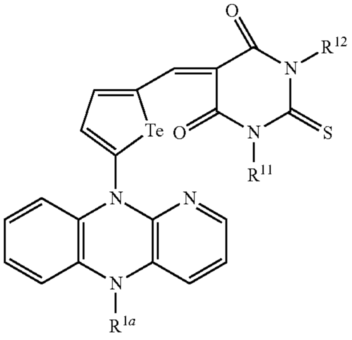

-continued
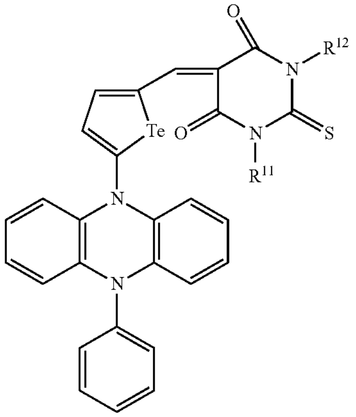
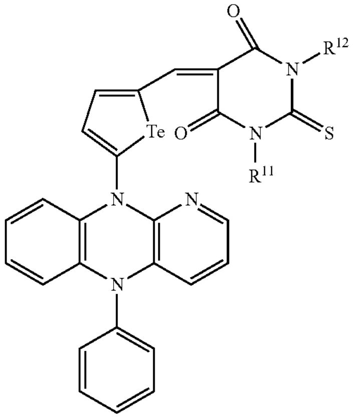
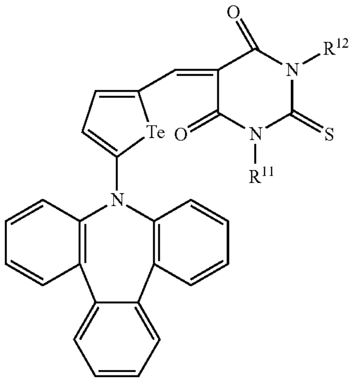
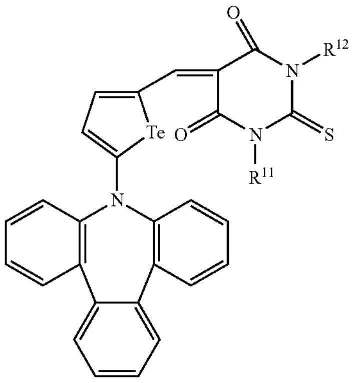
-continued
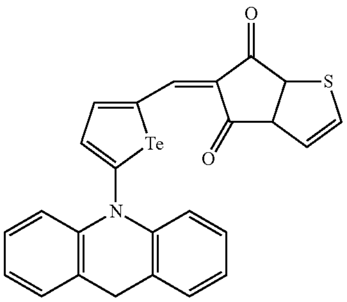
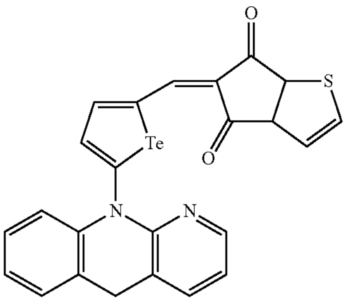
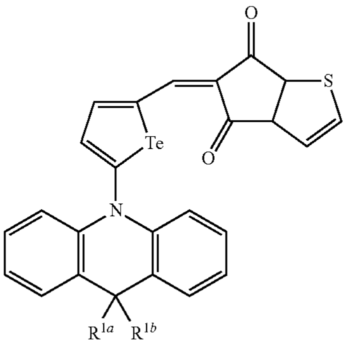
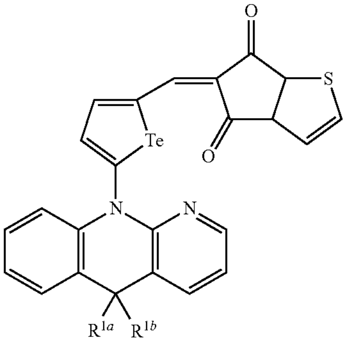
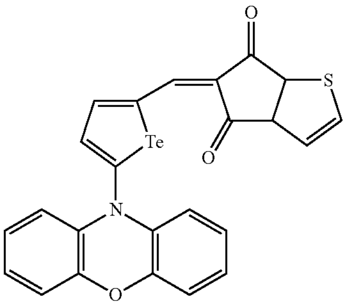

-continued
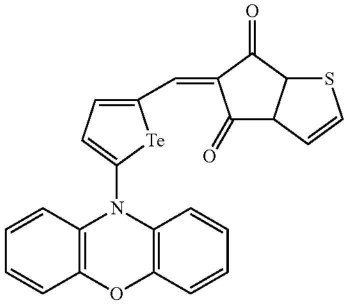
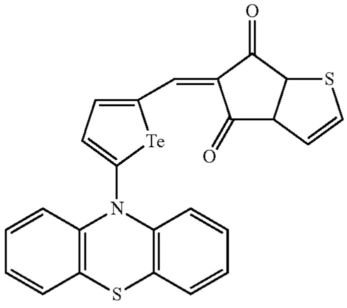
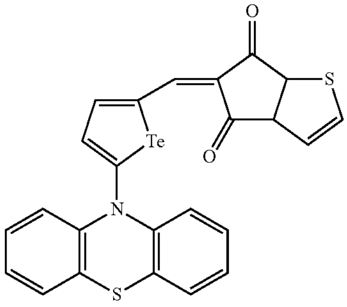
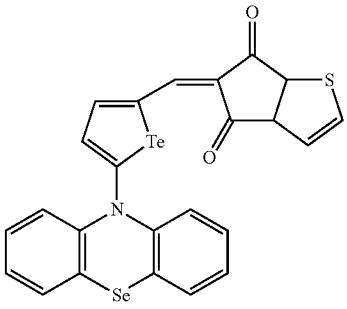
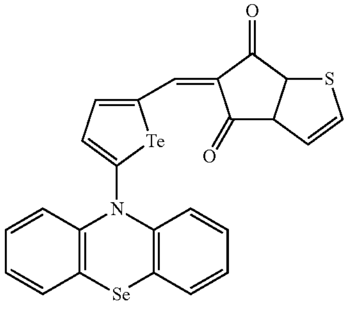
-continued
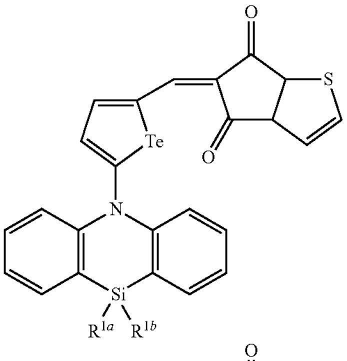
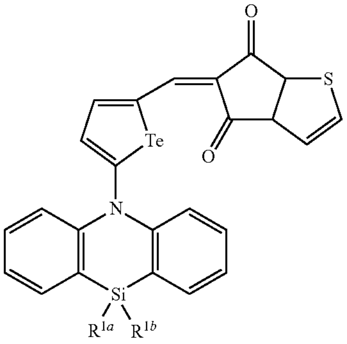
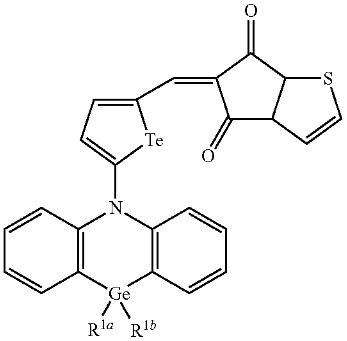
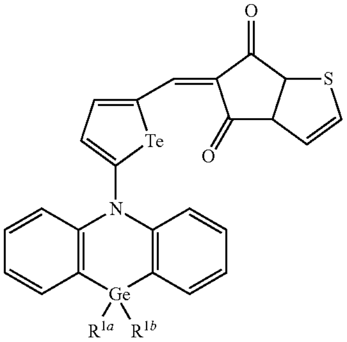
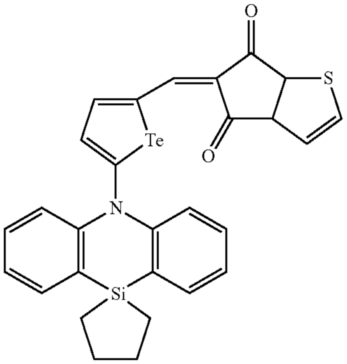

-continued
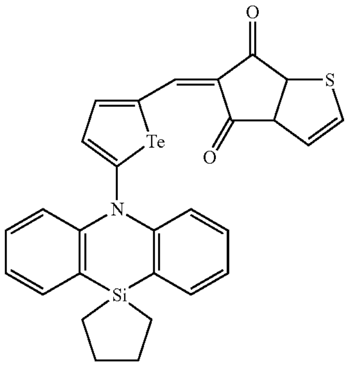
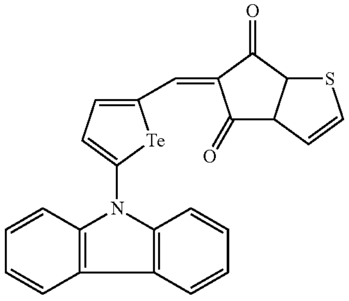
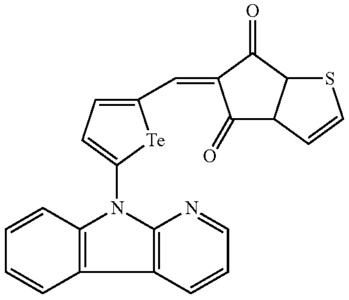
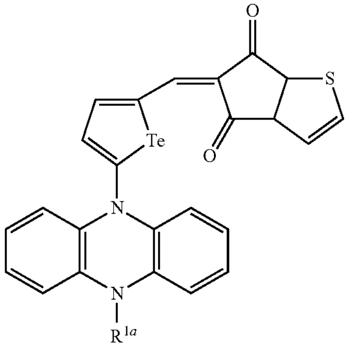
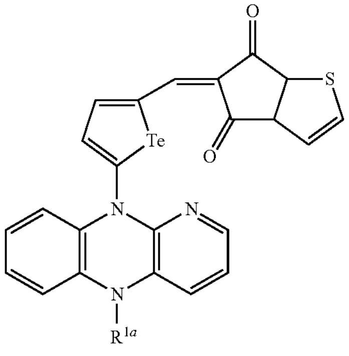
-continued
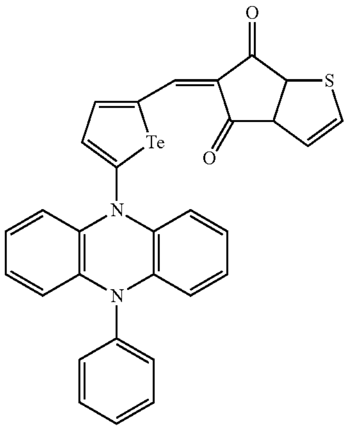
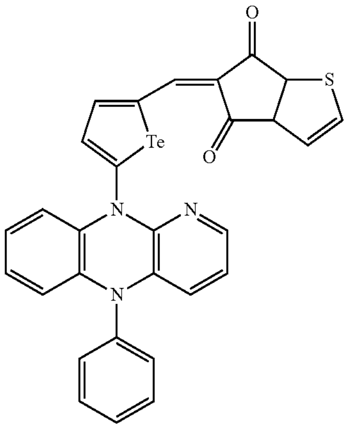
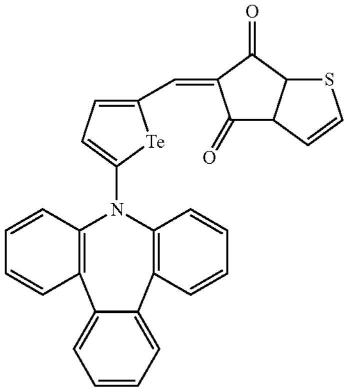
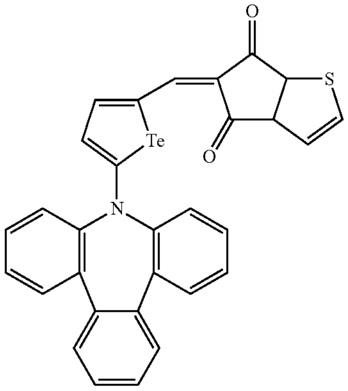

-continued
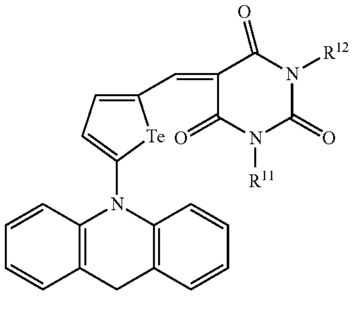
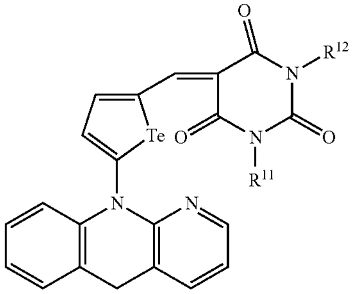
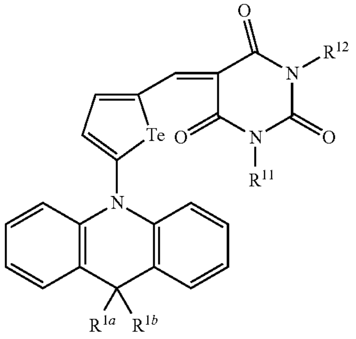
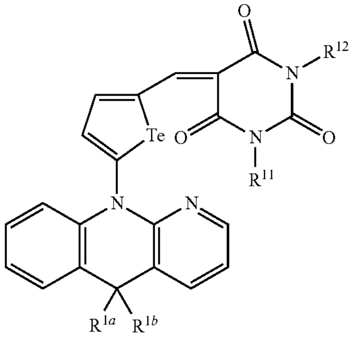
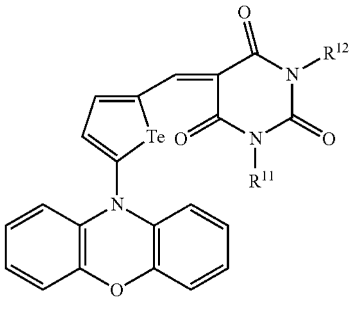
-continued
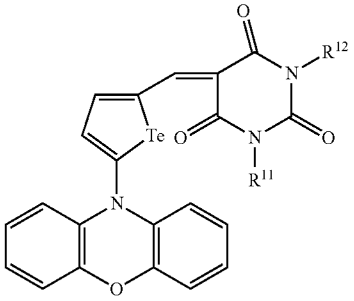
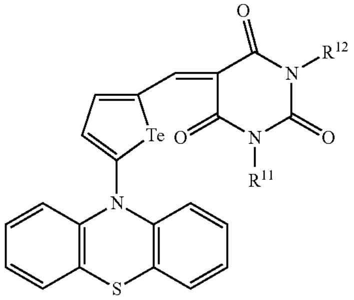
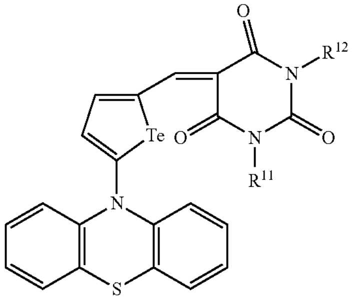
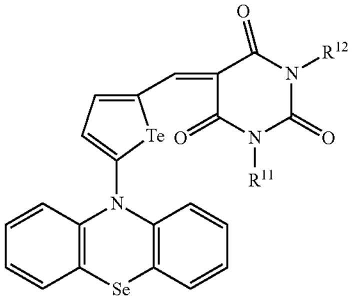
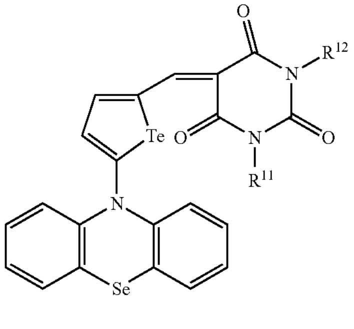

-continued
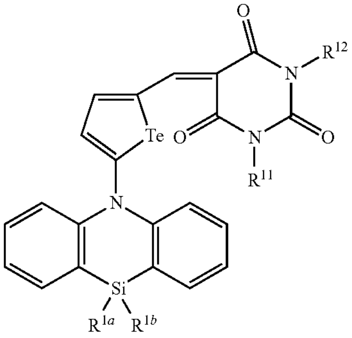
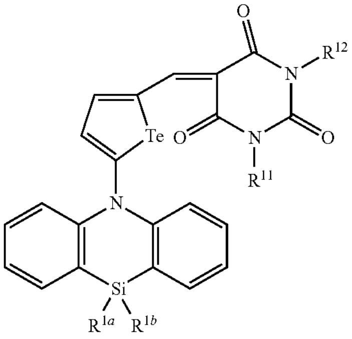
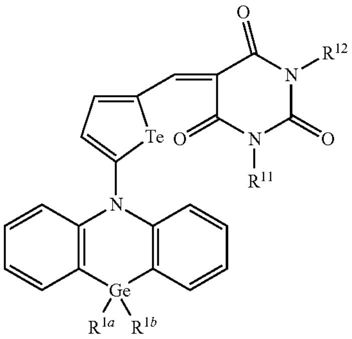
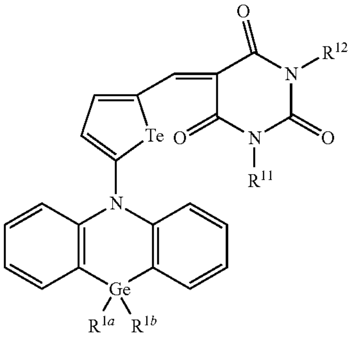
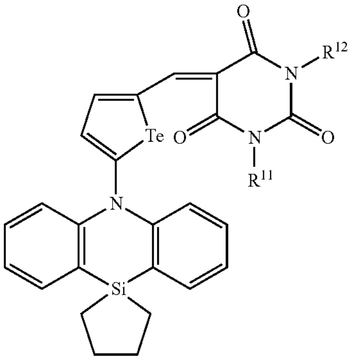
-continued
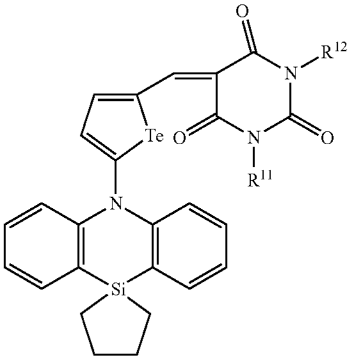
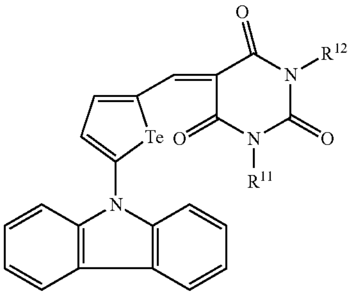
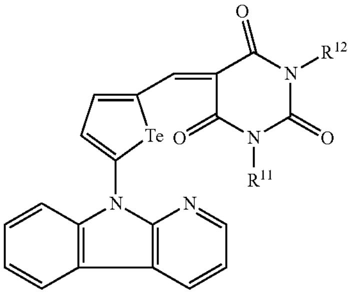
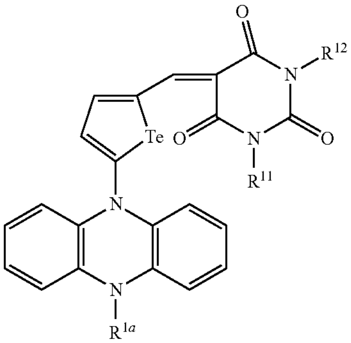
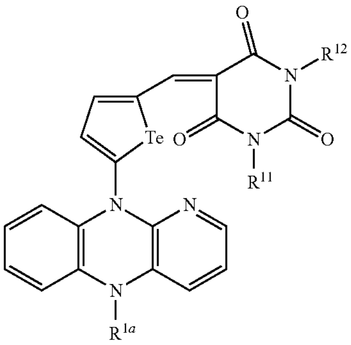

-continued
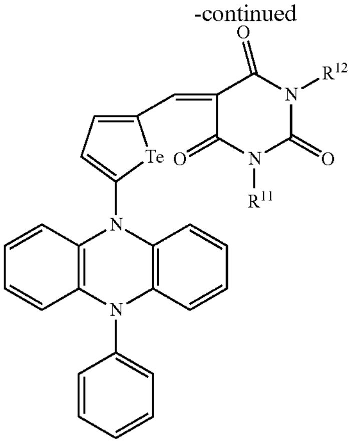
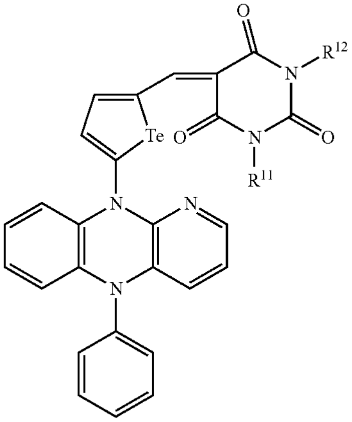
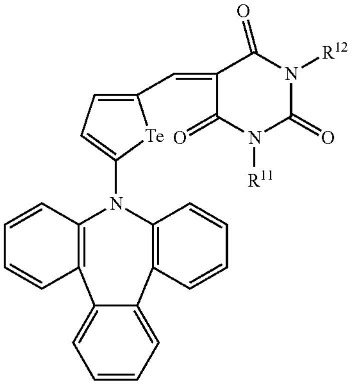
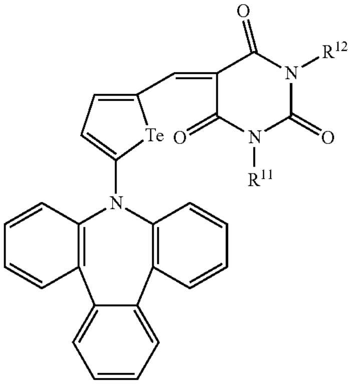
-continued
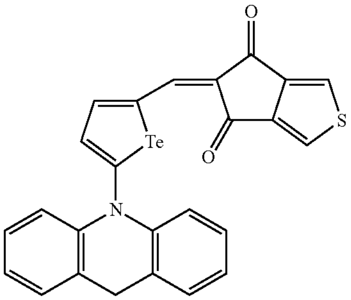
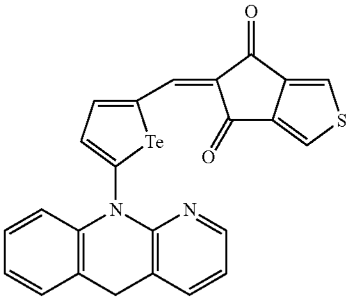
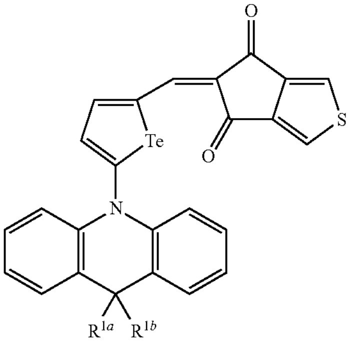
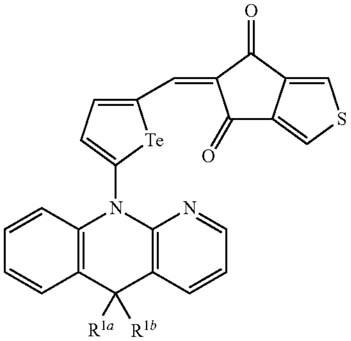
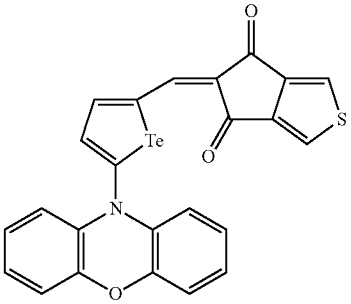

-continued
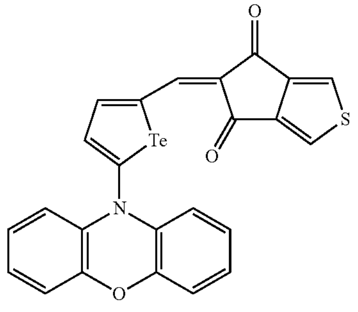
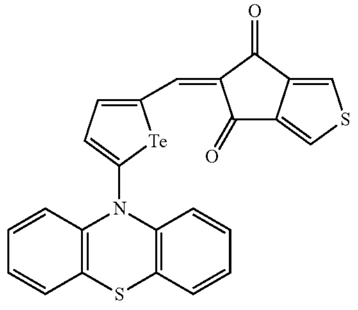
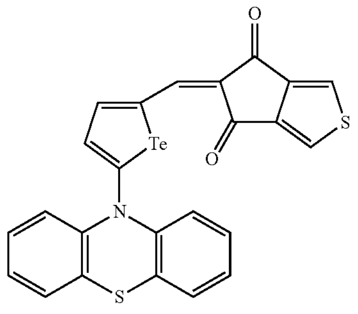
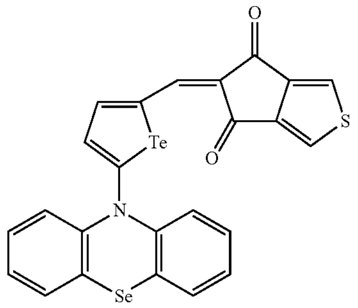
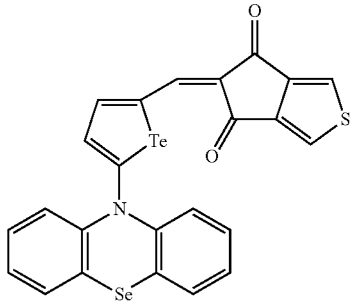
-continued
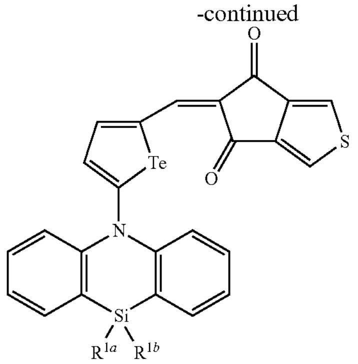
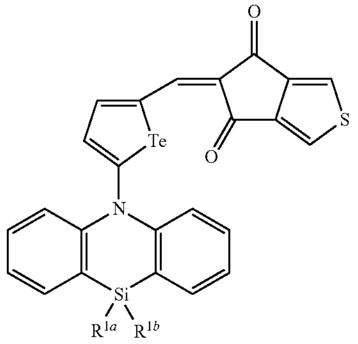
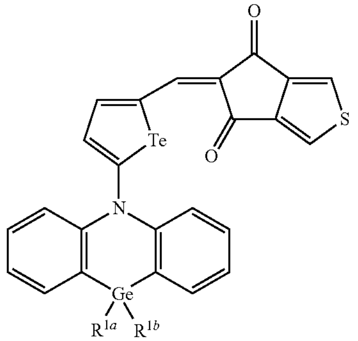
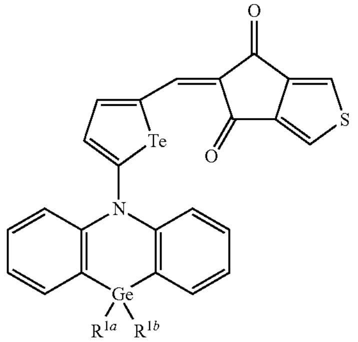
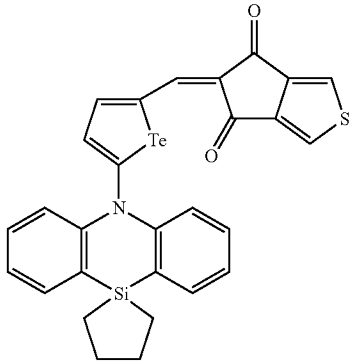

-continued
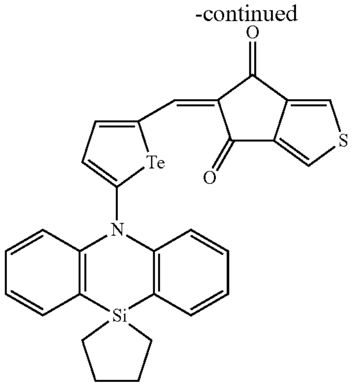
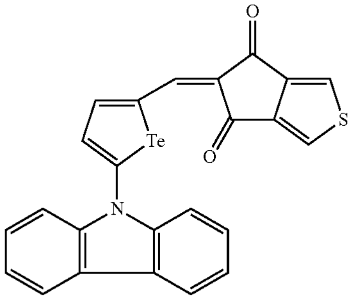
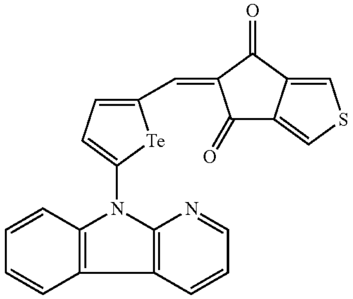
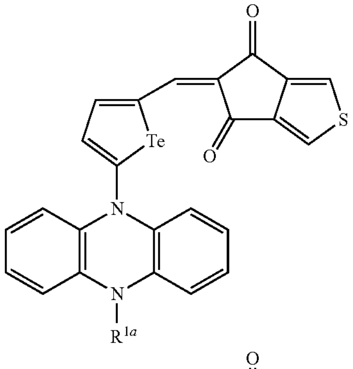
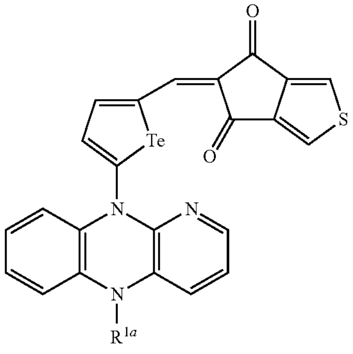
-continued
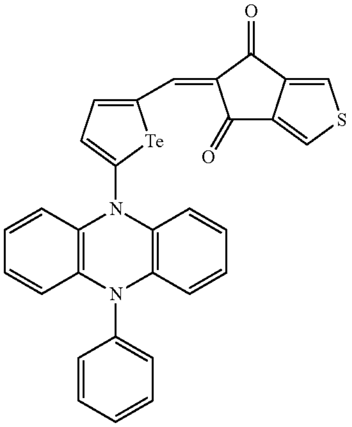
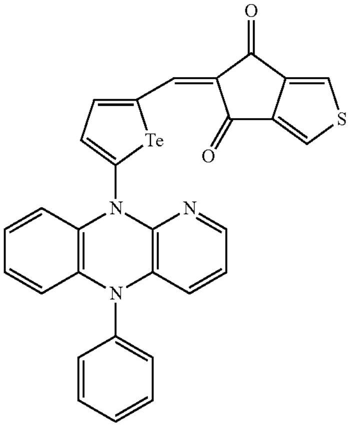
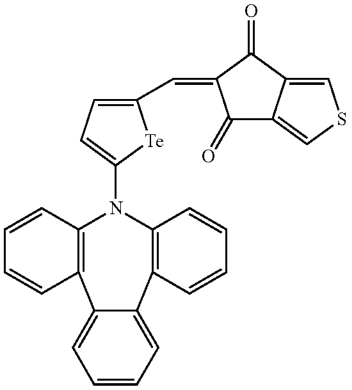
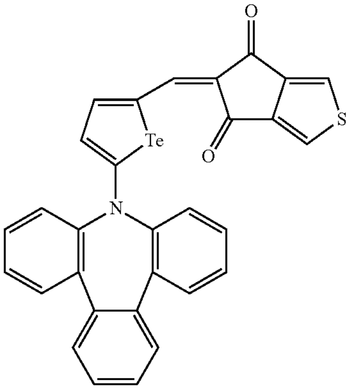
In Group 2B, one or more hydrogens present in each aromatic ring (i.e., aromatic hydrocarbon ring or heteroaromatic ring) may each be independently replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and any combination thereof, and $R^{1a}$, $R^{1b}$, $R^{11}$, and $R^{12}$ may each independently be hydrogen or a substituted or unsubstituted C1 to C6 alkyl group.

[Group 2C]

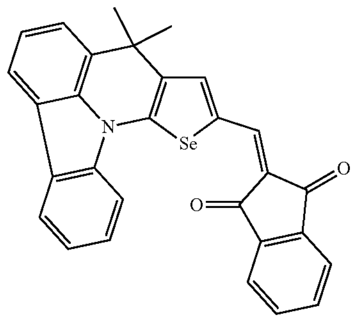

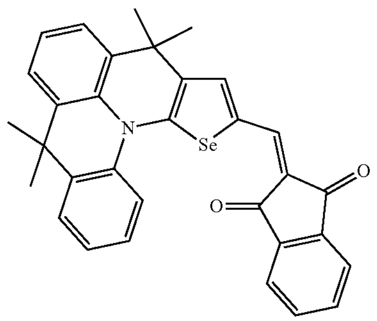

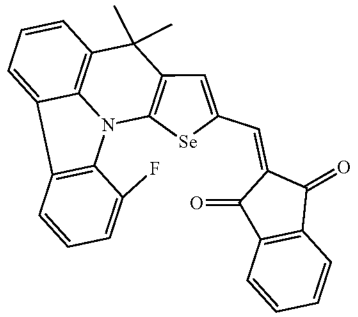

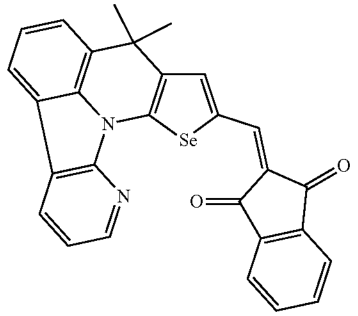

-continued

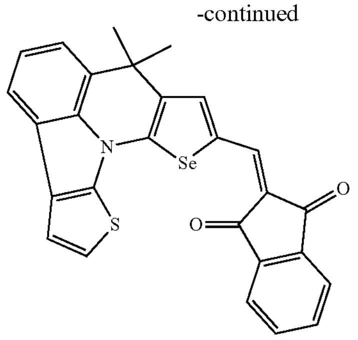

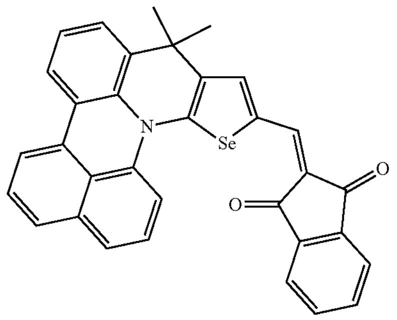

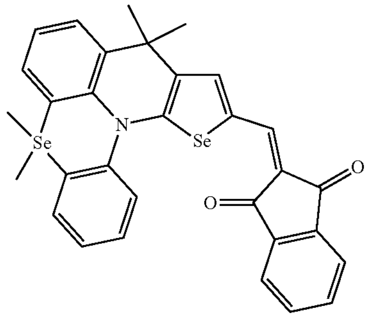

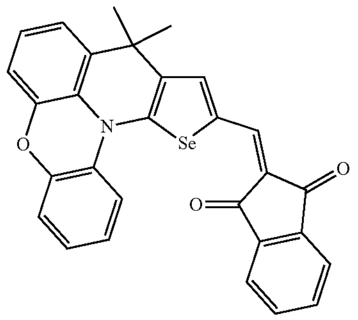

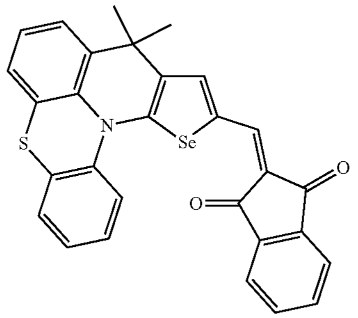

-continued
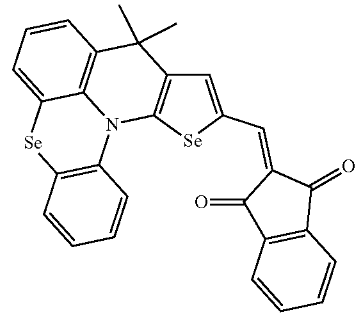
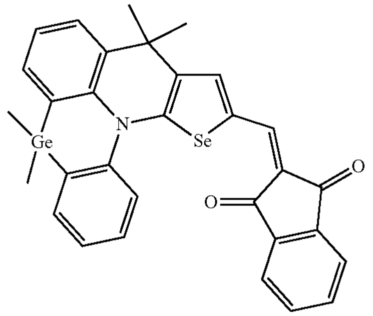
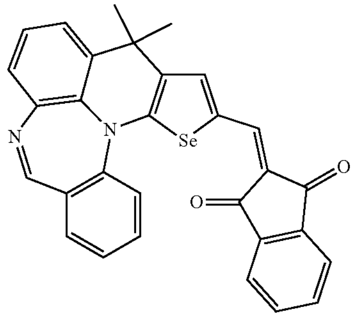
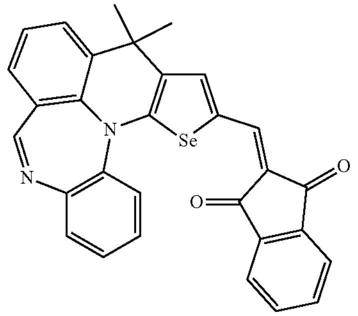
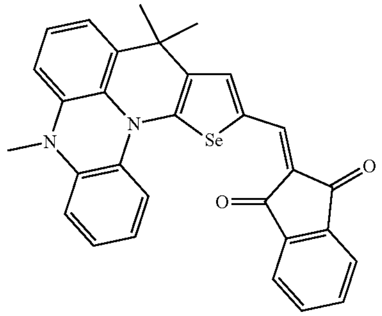
-continued
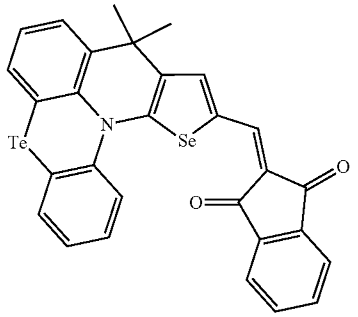
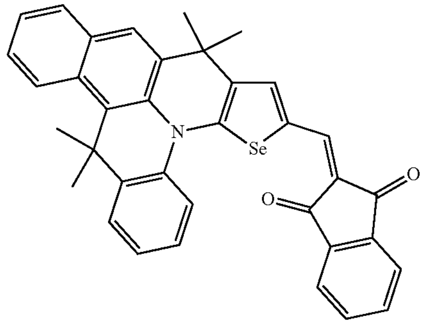
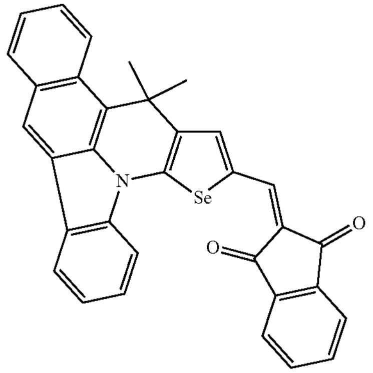
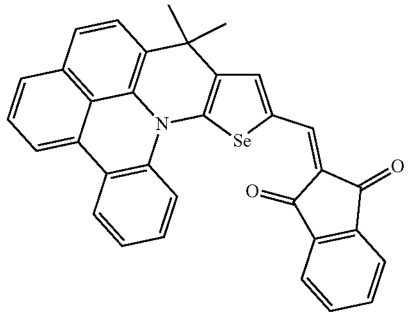
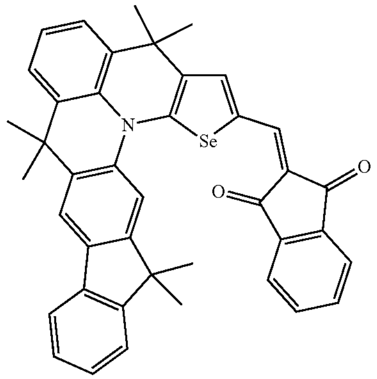

-continued
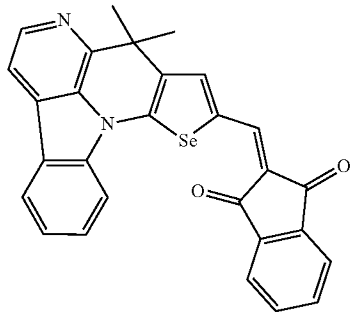
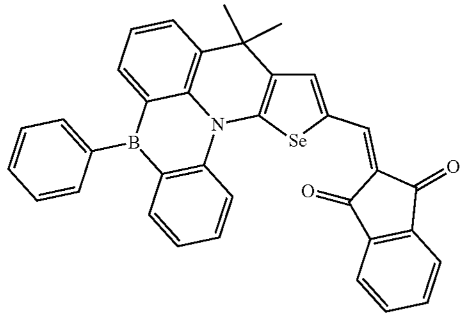
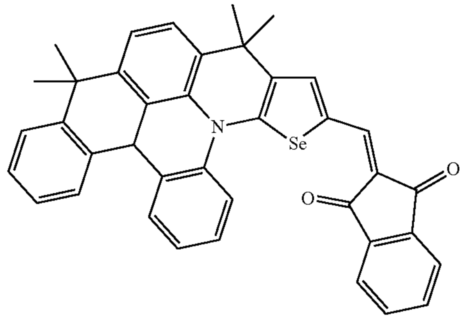
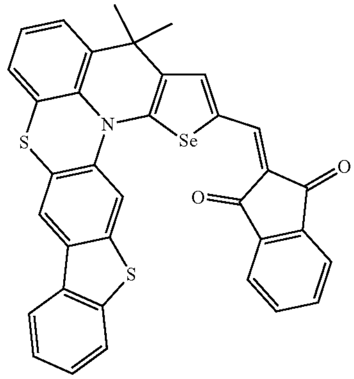
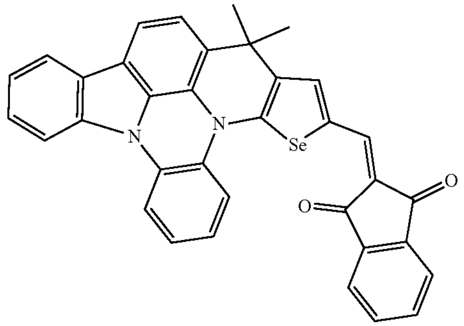
-continued
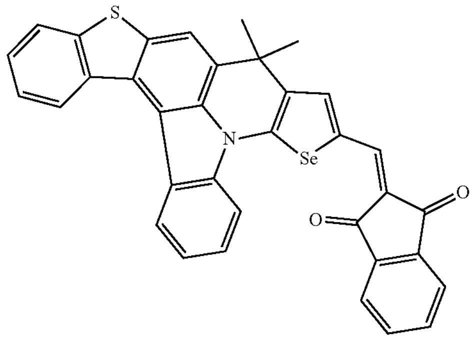
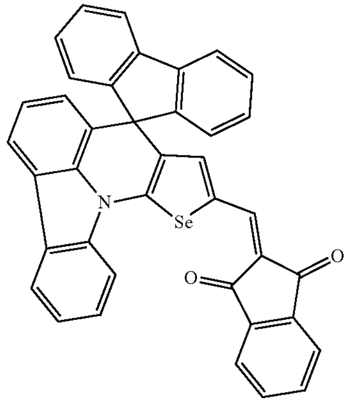
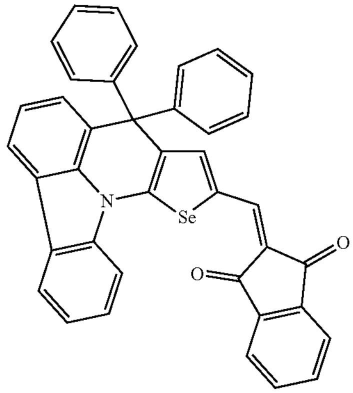
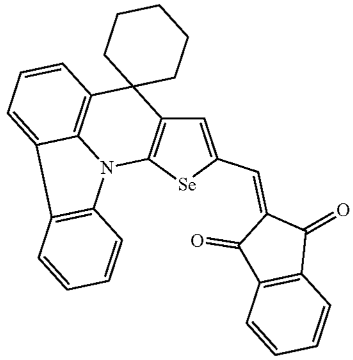

-continued
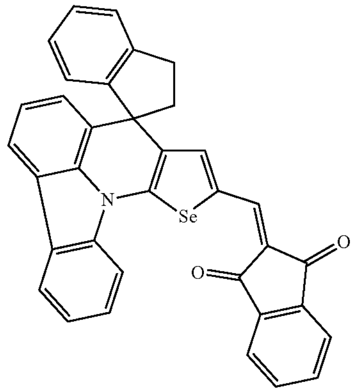
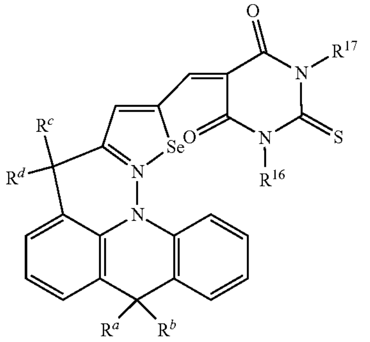
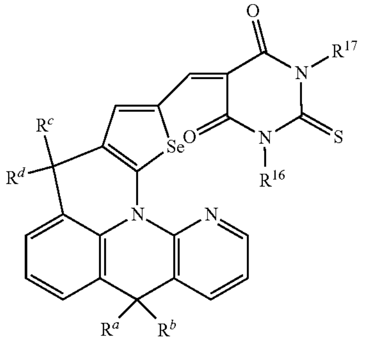
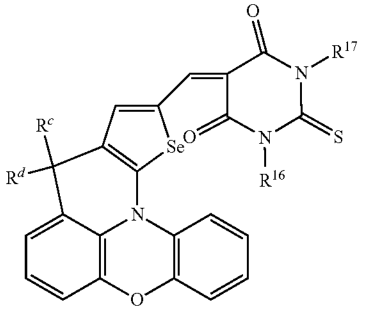
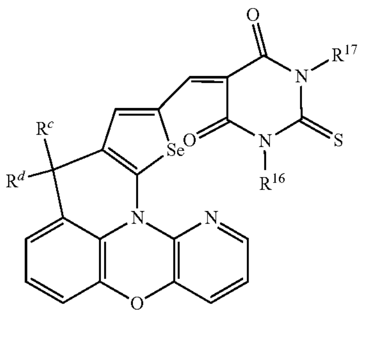
-continued
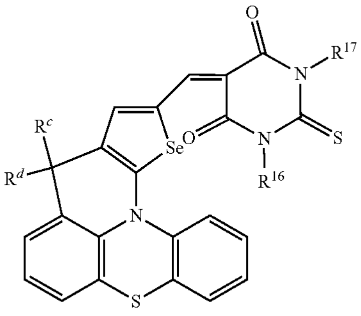
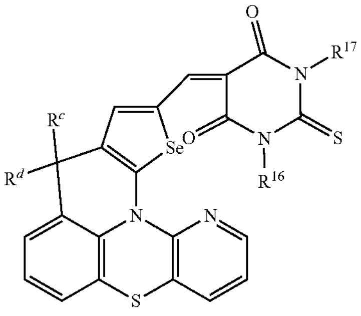
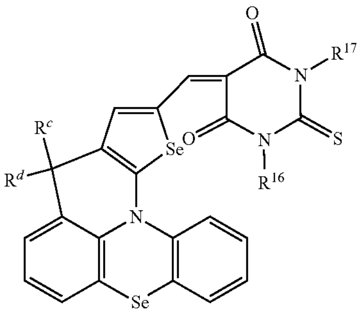
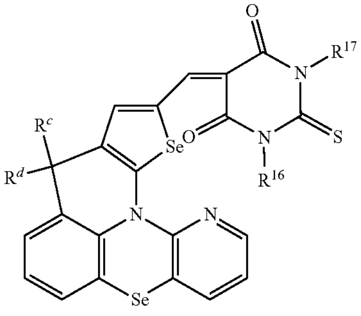
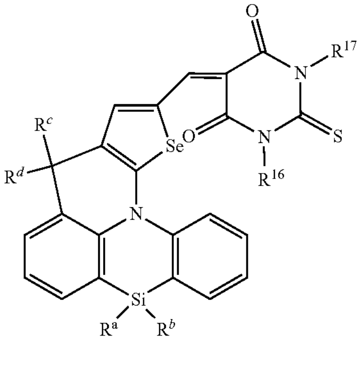

-continued
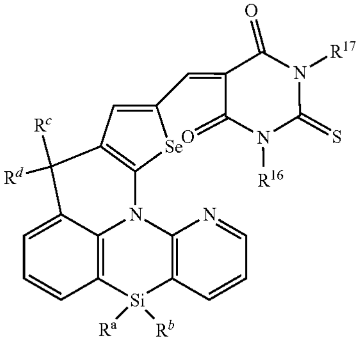
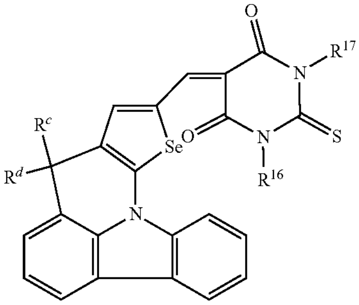
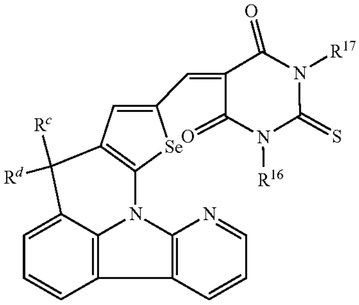
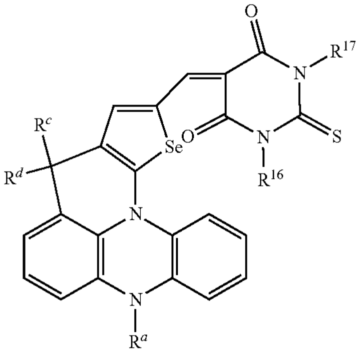
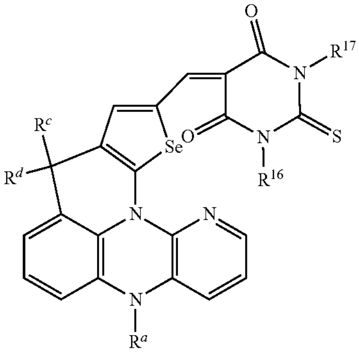
-continued
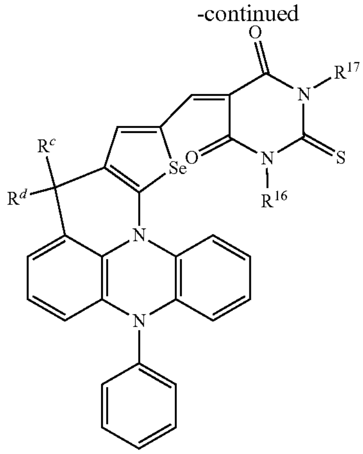
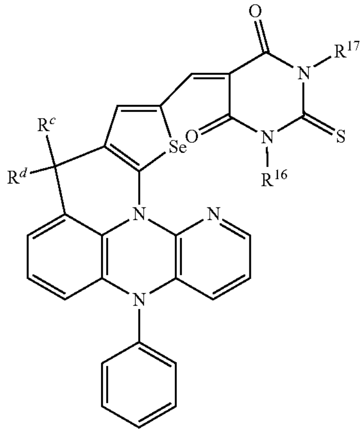
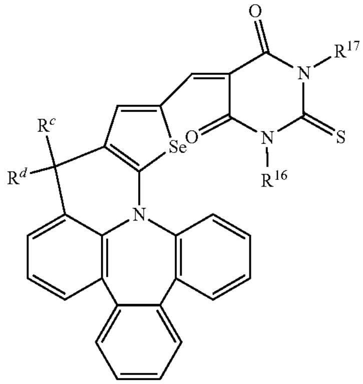
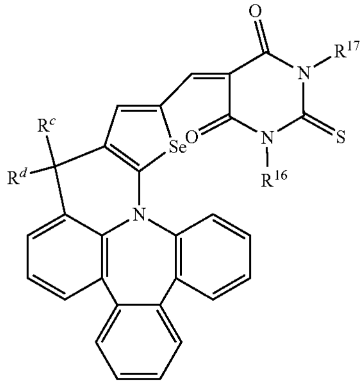

-continued

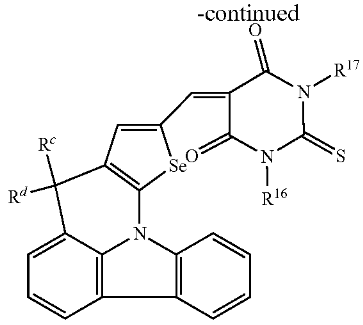

In Group 2C, one or more hydrogens present in each aromatic ring (i.e., aromatic hydrocarbon ring or heteroaromatic ring) may each be independently replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and any combination thereof, and $R^a$, $R^b$, $R^c$, $R^d$, $R^{16}$, and $R^{17}$ may each independently be hydrogen or a substituted or unsubstituted C1 to C6 alkyl group.

As an example, the n-type semiconductor may include the aforementioned organic compound, and a detailed description thereof is the same as described above.

For example, a LUMO energy level of the n-type semiconductor may be about 2.5 eV to about 4.5 eV, and within the above range, about 2.6 eV to about 4.3 eV, about 2.6 eV to about 4.0 eV, or about 2.8 eV to about 3.8 eV. For example, a HOMO energy level of the n-type semiconductor may be about 5.4 eV to about 7.0 eV, and within the above range, about 5.6 eV to about 6.8 eV, or about 5.8 eV to about 6.7 eV. For example, the bandgap energy of the n-type semiconductor may be about 1.8 eV to about 4.0 eV, and within the above range, about 1.9 eV to about 3.5 eV.

The p-type semiconductor and the n-type semiconductor may have similar thermal properties, and for example, a difference between the sublimation temperature of the p-type semiconductor and the n-type semiconductor may be less than or equal to about 150° C., within the above range, for example less than or equal to about 130° C., less than or equal to about 120° C., less than or equal to about 110° C., less than or equal to about 100° C., less than or equal to about 90° C., less than or equal to about 80° C., less than or equal to about 70° C., less than or equal to about 60° C., less than or equal to about 50° C., less than or equal to about 40° C., less than or equal to about 30° C., less than or equal to about 20° C., less than or equal to about 15° C., or less than or equal to about 10° C., and within the above range, about 0° C. to about 150° C., about 0° C. to about 130° C., about 0° C. to about 120° C., about 0° C. to about 110° C., about 0° C. to about 100° C., about 0° C. to about 90° C., about 0° C. to about 80° C., about 0° C. to about 70° C., about 0° C. to about 60° C., about 0° C. to about 50° C., about 0° C. to about 40° C., about 0° C. to about 30° C., about 0° C. to about 20° C., about 0° C. to about 15° C., about 0° C. to about 10° C., about 2° C. to about 150° C., about 2° C. to about 130° C., about 2° C. to about 120° C., about 2° C. to about 110° C., about 2° C. to about 100° C., about 2° C. to about 90° C., about 2° C. to about 80° C., about 2° C. to about 70° C., about 2° C. to about 60° C., about 2° C. to about 50° C., about 2° C. to about 40° C., about 2° C. to about 30° C., about 2° C. to about 20° C., about 2° C. to about 15° C., or about 2° C. to about 10° C.

For example, the sublimation temperature of the p-type semiconductor and the n-type semiconductor may be each less than or equal to about 380° C., within the above range, about 370° C., less than or equal to about 360° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., less than or equal to about 250° C., about 100° C. to about 380° C., about 100° C. to about 370° C., about 100° C. to about 360° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 360° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

The photoelectric conversion layer 130 may be an intrinsic layer (layer I) in which a p-type semiconductor and an n-type semiconductor are blended in a bulk heterojunction form. Herein, the p-type semiconductor and the n-type semiconductor may be blended in a volume ratio (thickness ratio) of about 1:9 to about 9:1, and within the above range, about 2:8 to about 8:2, within the above range, about 3:7 to about 7:3, within the above range, about 4:6 to about 6:4, or within the above range, about 5:5.

The photoelectric conversion layer 130 may further include a p-type layer and/or an n-type layer in addition to the intrinsic layer. The p-type layer may include the aforementioned p-type semiconductor, and the n-type layer may include the aforementioned n-type semiconductor. For example, the photoelectric conversion layer 130 may include various combinations such as p-type layer/I-layer, I-layer/n-type layer, p-type layer/I-layer/n-type layer, and the like.

The photoelectric conversion layer 130 may include a bi-layer including a p-type layer including the aforementioned p-type semiconductor and an n-type layer including the aforementioned n-type semiconductor. Herein, the thickness ratio of the p-type layer and the n-type layer may be about 1:9 to about 9:1, and within the above range, for example, about 2:8 to about 8:2, about 3:7 to about 7:3, about 4:6 to about 6:4, or about 5:5.

The photoelectric conversion layer 130 may have a thickness of about 10 nm to about 500 nm, and within the above range, about 20 nm to about 300 nm. Within the above thickness range, photoelectric conversion efficiency may be effectively improved by effectively absorbing light and effectively separating and transferring holes and electrons.

The first and second common auxiliary layers 140 and 150 may include a first common auxiliary layer 140 between the first electrode 110 and the photoelectric conversion layer 130 and a second common auxiliary layer 150 between the second electrode 120 and the photoelectric conversion layer 130. The first and second common auxiliary layers 140 and 150 may each independently be a charge auxiliary layer for controlling the mobility of holes and/or electrons separated from the photoelectric conversion layer 130 or a light absorption auxiliary layer for improving light absorption characteristics.

The first and second common auxiliary layers 140 and 150 may each include an organic material, an inorganic material, and/or an organic-inorganic material. The first and second common auxiliary layers 140 and 150 may include at least one selected from a hole injecting layer (HIL), a hole transporting layer (HTL), an electron blocking layer (EBL), and an electron injecting layer (EIL), an electron transporting layer (ETL), a hole blocking layer (HBL), and a light absorption auxiliary layer, but are not limited thereto.

The hole injection layer, the hole transport layer, and/or the electron blocking layer may include, for example, a phthalocyanine compound such as copper phthalocyanine; DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino]triphenylamine), TDATA (4,4'4"-tris(N,N-diphenylamino)triphenylamine), 2-TNATA (4,4',4"-tris{N-(2-naphthyl)-N-phenylamino}-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/Camphor sulfonic acid), PANI/PSS (polyaniline/poly(4-styrenesulfonate)), NPB (N,N'-di(naphthalene-1-yl)-N,N'-diphenylbenzidine), polyetherketone including triphenylamine (TPAPEK), 4-isopropyl-4'-methyldiphenyliodonium[tetrakis(pentafluorophenyl)borate], HAT-CN (dipyrazino[2,3-f: 2',3'-h]quinoxaline-2,3,6,7,10,11-hexacarbonitrile), a carbazole-based derivative such as N-phenylcarbazole, polyvinylcarbazole, and the like, a fluorene-based derivative, TPD (N,N'-bis(3-methylphenyl)-N,N'-diphenyl-[1,1-biphenyl]-4,4'-diamine), a triphenylamine-based derivative such as TCTA (4,4',4"-tris(N-carbazolyl)triphenylamine), NPB (N,N'-di(naphthalene-1-yl)-N,N'-diphenyl-benzidine), TAPC (4,4'-cyclohexylidene bis[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), or any combination thereof, but is not limited thereto.

The electron injection layer, the electron transport layer, and/or the hole blocking layer may be, for example, a halogenated metal such as LiF, NaCl, CsF, RbCl, and RbI; a lanthanide metal such as Yb; a metal such as calcium (Ca), potassium (K), aluminum (Al), or an alloy thereof; a metal oxide such as $Li_2O$ or BaO; Liq (lithium quinolate), Alq3 (tris(8-hydroxyquinolinato)aluminum), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-ylphenyl)-9,10-dinaphthylanthracene, TPBi (1,3,5-tri(1-phenyl-1H-benzo[d]imidazol-2-yl)phenyl), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tertbutylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,O8)-(1,1'-biphenyl-4-olato)aluminum), $Bebq_2$ (berylliumbis(benzoquinolin-10-olate), ADN (9,10-di(naphthalen-2-yl)anthracene), BmPyPhB (1,3-bis[3,5-di(pyridin-3-yl)phenyl]benzene), or any combination thereof, but is not limited thereto.

Any one of the first or second common auxiliary layers 140 and 150 may be omitted.

The sensor 100 may further include an anti-reflection layer (not shown) under the first electrode 110 or on the second electrode 120. For example, when the first electrode 110 is a light-receiving electrode, the anti-reflection layer may be disposed under the first electrode 110. For example, when the second electrode 120 is a light-receiving electrode, the anti-reflection layer may be on the second electrode 120. The anti-reflection layer is disposed at a light incidence side and may lower reflectance of light of incident light and thereby light absorbance may be further improved. The anti-reflection layer may include, for example a material having a refractive index of about 1.6 to about 2.5, and may include for example at least one of metal oxide, metal sulfide, or an organic material having a refractive index within the above ranges. The anti-reflection layer may include, for example a metal oxide such as aluminum-containing oxide, molybdenum-containing oxide, tungsten-containing oxide, vanadium-containing oxide, rhenium-containing oxide, niobium-containing oxide, tantalum-containing oxide, titanium-containing oxide, nickel-containing oxide, copper-containing oxide, cobalt-containing oxide, manganese-containing oxide, chromium-containing oxide, tellurium-containing oxide, or any combination thereof; a metal sulfide such as zinc sulfide; or an organic material such as an amine derivative, but is not limited thereto.

The sensor 100 may further include a focusing lens (not shown). The focusing lens may collect the light to a single point by controlling the direction of the incident light at a light incident position. The focusing lens may have a shape of, for example, a cylinder or a hemisphere, but is not limited thereto.

In the sensor 100, light enters through the first electrode 110 or the second electrode 120, and the photoelectric conversion layer 130 may be configured to absorb light in a particular (or, alternatively, predetermined) wavelength spectrum, and thus excitons may be generated thereinside. The excitons are separated into holes and electrons in the photoelectric conversion layer 130, and the separated holes are transported to an anode that is one of the first electrode 110 or the second electrode 120, and the separated electrons are transported to the cathode that is the other of the first electrode 110 or the second electrode 120, so as to flow a current.

The sensor 100 may be included in, for example, an image sensor or a biometric sensor.

The image sensor may be for example a CMOS image sensor.

The biometric sensor may include, for example, a fingerprint sensor, an iris recognition sensor, a distance sensor, a photoplethysmography (PPG) sensor device, an electroencephalogram (EEG) sensor device, an electrocardiogram (ECG) sensor device, a blood pressure (BP) sensor device, an electromyography (EMG) sensor device, a blood glucose (BG) sensor device, an accelerometer device, a RFID antenna device, an inertial sensor device, an activity sensor device, a strain sensor device, a motion sensor device, or any combination thereof, but is not limited thereto.

For example, the aforementioned sensor 100 may be included in an image sensor, and as described above, has improved optical and electrical properties and reduces an image afterimage due to remaining charges, based on including the organic compound, thereby being applied to an image sensor suitable for high-speed photographing.

Hereinafter, an image sensor according to some example embodiments is described.

Figure 2:
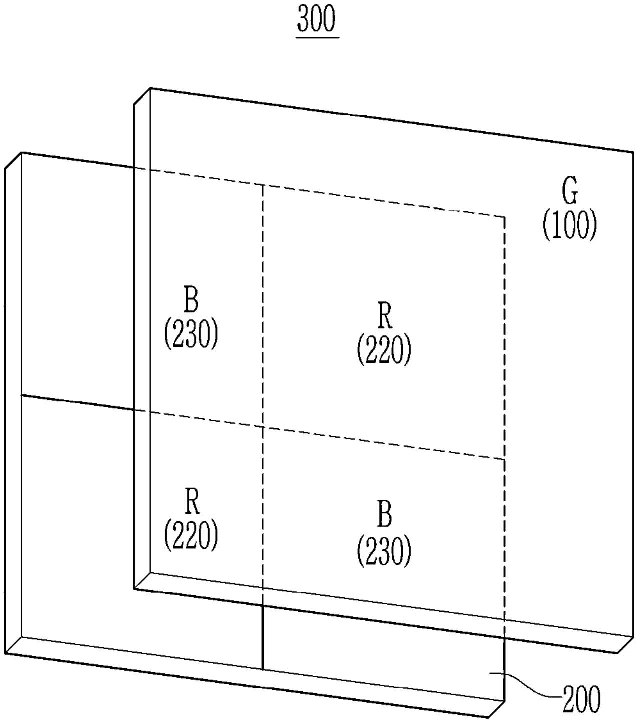
FIG. 2 is a plan view showing an example of an image sensor according to some example embodiments.
Figure 3:
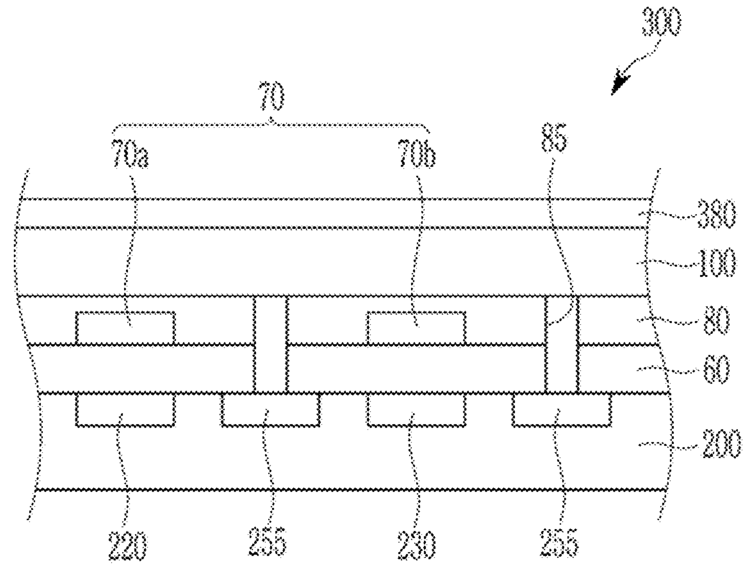
FIG. 3 is a cross-sectional view showing an example of the image sensor of FIG. 2.

FIG. 2 is a plan view showing an example of an image sensor according to some example embodiments and FIG. 3 is a cross-sectional view showing an example of the image sensor of FIG. 2.

Referring to FIG. 2, the image sensor 300 according to some example embodiments may be a stacked sensor in which a semiconductor substrate 200 and the aforementioned sensor 100 are stacked, and the semiconductor substrate 200 includes a first photodiode 220 and a second photodiode 230 which are overlapped with the sensor 100. FIG. 2 illustrates an example of a repeating unit pixel group in the image sensor 300, and the unit pixel group is repeatedly arranged along rows and/or columns. In FIG. 2, the unit pixel group is shown as a 2×2 array in which two red pixels (R) and two blue pixels (B) are arranged in a semiconductor substrate 200 but not limited thereto.

A first photodiode 220 and a second photodiode 230 are each integrated in the semiconductor substrate 200 and thus may be configured to absorb and convert light having each different wavelength spectrum which is filtered by a color filter layer 70, which will be described later. A wavelength spectrum photoelectrically converted in the sensor 100 may be different respectively from the wavelength spectra photoelectrically converted in the first photodiode 220 and the second photodiode 230, for example, the wavelength spectrum photoelectrically converted in the first photodiode 220 and the wavelength spectrum photoelectrically converted in the second photodiode 230 may be respectively different from the wavelength spectrum photoelectrically converted in the sensor 100 and selected from light of a red wavelength spectrum, a green wavelength spectrum, and a blue wavelength spectrum. For example, the first photodiode 220 may photoelectrically convert light of the red wavelength spectrum (R), the second photodiode 230 may photoelectrically convert light of the blue wavelength spectrum (B), and the sensor 100 may photoelectrically convert light of the green wavelength spectrum (G).

Referring to FIG. 3, an image sensor 300 according to some example embodiments includes a substrate 200, a lower insulation layer 60, a color filter layer 70, an upper insulation layer 80, a sensor 100, and an encapsulation layer 380.

The substrate 200 may be a semiconductor substrate, and the first and second photodiodes 220 and 230, a transmission transistor (not shown) and the charge storage 255 are integrated therein. The first or second photodiode 220 or 230, transmission transistor and/or charge storage 255 may be integrated for each pixel. As shown in the drawing, the first photodiode 220 may be included in the red pixel R and the second photodiode 230 may be included in the blue pixel B. The charge storage 255 is electrically connected to the sensor 100.

A metal wire (not shown) and a pad (not shown) are formed on the lower portion or upper portion of the substrate 200. In order to decrease signal delay, the metal wire and pad may be made of a metal having low resistivity, for example, aluminum (Al), copper (Cu), silver (Ag), and alloys thereof, but is not limited thereto.

The lower insulation layer 60 is formed on the substrate 200. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench 85 exposing the charge storage 255. The trench 85 may be filled with fillers.

The color filter layer 70 is formed on the lower insulation layer 60. The color filter layer 70 includes a red filter 70*a* formed in the red pixel R and a blue filter 70*b* formed in the blue pixel B. However, the present inventive concepts are not limited thereto, and a cyan filter, a magenta filter, and/or a yellow filter may be included instead of the red filter 70*a* and/or the blue filter 70*b*, or may be additionally included in addition to the red filter 70*a* and the blue filter 70*b*. Although an example in which the green filter is not provided is described in some example embodiments, including the example embodiments shown in FIG. 3, a green filter may be provided in some example embodiments.

The upper insulation layer 80 is formed on the color filter layer 70. The upper insulation layer 80 may remove the step difference caused by the color filter layer 70 and may be planarized. The upper insulation layer 80 and the lower insulation layer 60 have a contact (not shown) exposing the pad and a trench 85 exposing the charge storage 255.

The aforementioned sensor 100 is formed on the upper insulation layer 80. A detailed description of the sensor 100 is the same as described above. One of the first electrode 110 or the second electrode 120 of the sensor 100 may be electrically connected to the charge storage 255 and the other of the first electrode 110 or the second electrode 120 of the sensor 100 may be a light-receiving electrode. For example, the first electrode 110 of the sensor 100 may be electrically connected to the charge storage 255, and the second electrode 120 of the sensor 100 may be a light-receiving electrode.

The encapsulation layer 380 may protect the image sensor 300, and may include a thin film of one or two or more layers including an organic material, an inorganic material, an organic-inorganic material, or any combination thereof. The encapsulation layer 380 may include, for example, a glass plate, a metal thin film, an organic layer, an inorganic layer, an organic-inorganic layer, or any combination thereof. The organic film may include, for example, an acrylic resin, a (meth)acrylic resin, polyisoprene, a vinyl resin, an epoxy resin, a urethane resin, a cellulose resin, a perylene resin, or any combination thereof, but is not limited thereto. The inorganic film may include, for example, an oxides, a nitride, and/or an oxynitride, for example silicon oxide, silicon nitride, silicon oxynitride, aluminum oxide, aluminum nitride, aluminum oxynitride, zirconium oxide, zirconium nitride, zirconium oxynitride, titanium oxide, titanium nitride, titanium oxynitride, hafnium oxide, hafnium nitride, hafnium oxynitride, tantalum oxide, tantalum nitride, tantalum oxynitride, lithium fluoride, or any combination thereof, but is not limited thereto. The organic-inorganic film may include, for example, polyorganosiloxane, but is not limited thereto. The encapsulation layer 380 may be one layer or two or more layers. The encapsulation layer 380 may be omitted.

A focusing lens (not shown) may be further formed on the sensor 100 (or the encapsulation layer 380). The focusing lens may control the direction of the incident light to collect the light to a single point. The focusing lens may have a shape of, for example, a cylinder or a hemisphere, but is not limited thereto.

Figure 4:
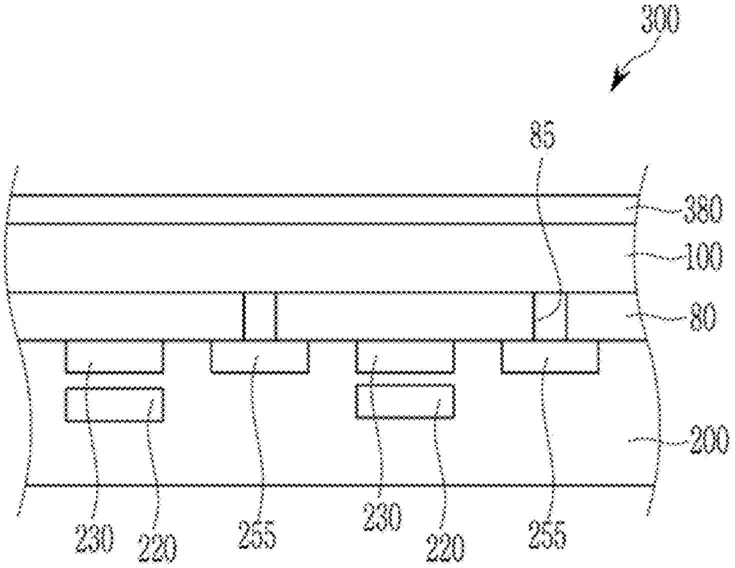
FIG. 4 is a cross-sectional view showing another example of the image sensor of FIG. 2.

FIG. 4 is a cross-sectional view showing the image sensor of FIG. 2 according to some example embodiments.

Referring to FIG. 4, the image sensor 300 according to some example embodiments includes a substrate 200 integrated with the first and second photodiodes 220 and 230, a transmission transistor (not shown), and a charge storage 255; an upper insulation layer 80; a sensor 100; and an encapsulation layer 380, like some example embodiments, including the example embodiments shown in FIG. 3.

However, in the image sensor 300 according to some example embodiments, including the example embodiments shown in FIG. 4, the first and second photodiodes 220 and 230 are stacked in a vertical direction with respect to the surface direction (e.g., a thickness direction of substrate 200) of the substrate 200, and the color filter layer 70 and lower insulation layer 60 are omitted, unlike some example embodiments, including the example embodiments shown in FIG. 3. The first and second photodiodes 220 and 230 are electrically connected to a charge storage (not shown) and their information may be transferred by a transmission transistor. The first and second photodiodes 220 and 230 may be configured to selectively absorb light in each wavelength spectrum according to the stacking depth.

The sensor 100 is the same as described above. One of the first electrode 110 or the second electrode 120 of the sensor 100 may be a light-receiving electrode, and the other of the first electrode 110 or the second electrode 120 of the sensor 100 may be electrically connected to the charge storage 255.

Figure 5:
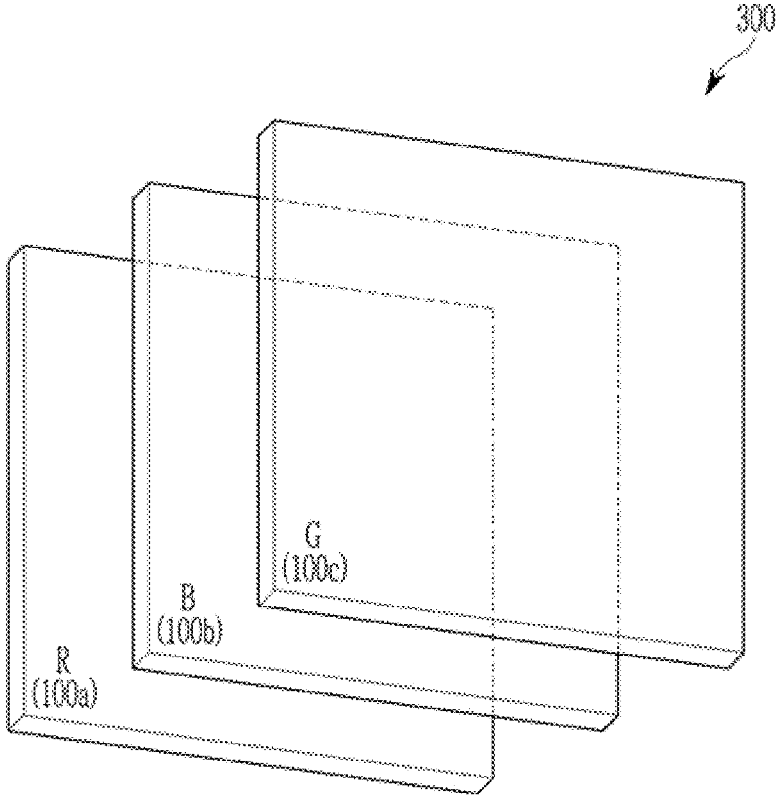
FIG. 5 is a plan view showing another example of an image sensor according to some example embodiments.
Figure 6:
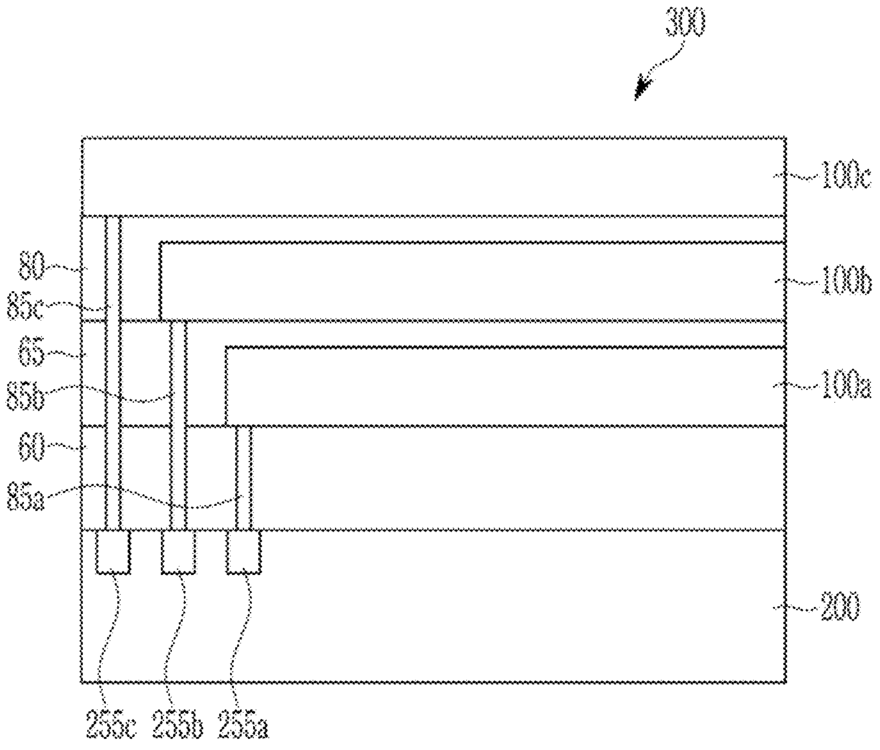
FIG. 6 is a cross-sectional view showing an example of the image sensor of FIG. 5.

FIG. 5 is a plan view showing another example of an image sensor according to some example embodiments, and FIG. 6 is a cross-sectional view showing an example of the image sensor of FIG. 5.

The image sensor 300 according to some example embodiments, including the example embodiments shown in FIGS. 5 and 6, may have a structure in which a green sensor configured to selectively absorb light in a green wavelength spectrum, a blue sensor configured to selectively absorb light in a blue wavelength spectrum, and a red sensor configured to selectively absorb light in a red wavelength spectrum are stacked.

The image sensor 300 according to some example embodiments includes a substrate 200, a lower insulation layer 60, an intermediate insulation layer 65, an upper insulation layer 80, a first sensor 100*a*, a second sensor 100*b*, and a third sensor 100*c*.

The substrate 200 may be a semiconductor substrate such as a silicon substrate, and a transmission transistor (not shown) and charge storages 255*a*, 255*b*, and 255*c* are integrated therein.

A metal wire (not shown) and a pad (not shown) are formed on the substrate 200, and a lower insulation layer 60 is formed on the metal wire and the pad.

The first sensor 100*a*, the second sensor 100*b*, and the third sensor 100*c* are sequentially formed on the lower insulation layer 60.

At least one (e.g., one, two, or three) of the first, second, or third sensors 100*a*, 100*b*, or 100*c* may be the aforementioned sensor 100. For example, the first, second, and third sensors 100*a*, 100*b*, and 100*c* may each be the aforementioned sensor 100. One of the first electrode 110 or the second electrode 120 of the first, second, and third sensors 100*a*, 100*b*, and 100*c* may be a light-receiving electrode, and the other of the first electrode 110 or the second electrode 120 of the first, second, and third sensors 100*a*, 100*b*, and 100*c* may be connected to the charge storages 255*a*, 255*b*, and 255*c*.

The first sensor 100*a* may be configured to selectively absorb light in any one wavelength spectrum of red, blue, and green to photoelectrically convert the absorbed light. For example, the first sensor 100*a* may be a red sensor. The intermediate insulation layer 65 is formed on the first sensor 100*a*.

The second sensor 100*b* is formed on the intermediate insulation layer 65. The second sensor 100*b* may be configured to selectively absorb light of any one wavelength spectrum among red, blue, and green to photoelectrically convert the absorbed light. For example, the second sensor 100*b* may be a blue sensor.

The upper insulation layer 80 is formed on the second sensor 100*b*. The lower insulation layer 60, the intermediate insulation layer 65, and the upper insulation layer 80 have a plurality of trenches 85*a*, 85*b*, and 85*c* exposing charge storages 255*a*, 255*b*, and 255*c*.

The third sensor 100*c* is formed on the upper insulation layer 80. The third sensor 100*c* may be configured to selectively absorb light of any one wavelength spectrum among red, blue, and green to photoelectrically convert the absorbed light. For example, the third sensor 100*c* may be a green sensor.

A focusing lens (not shown) may be further formed on the third sensor 100*c*. The focusing lens may control the direction of the incident light to collect the light to a single point. The focusing lens may have a shape of, for example, a cylinder or a hemisphere, but is not limited thereto.

Although the drawing shows a structure in which the first sensor 100*a*, the second sensor 100*b*, and the third sensor 100*c* are sequentially stacked, the stacking order is not limited thereto and the stacking order may be variously changed.

As described above, the first sensor 100*a*, the second sensor 100*b*, and the third sensor 100*c*, which are configured to absorb light in different wavelength spectra, are stacked, thereby further reducing a size of the image sensor to provide a miniaturized image sensor.

Figure 7:
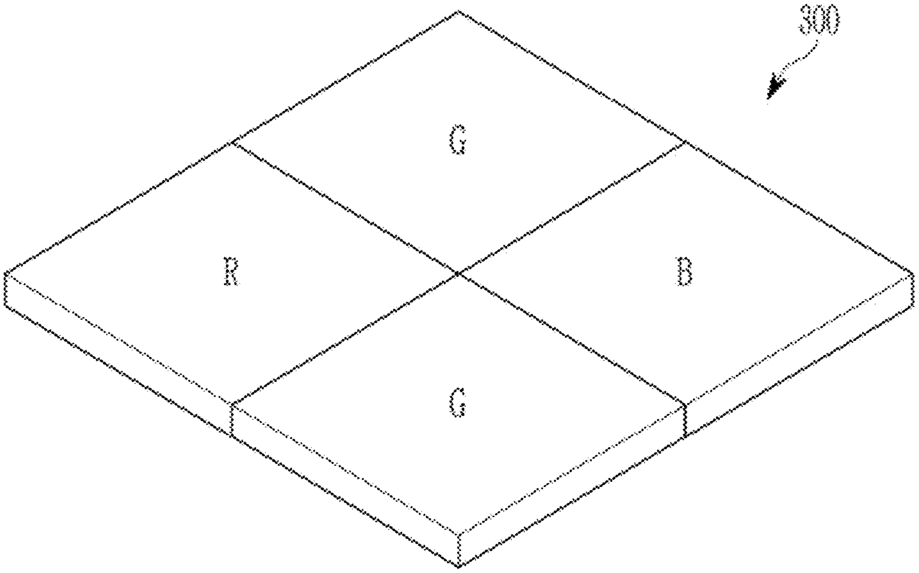
FIG. 7 is a plan view showing another example of an image sensor according to some example embodiments.
Figure 8:
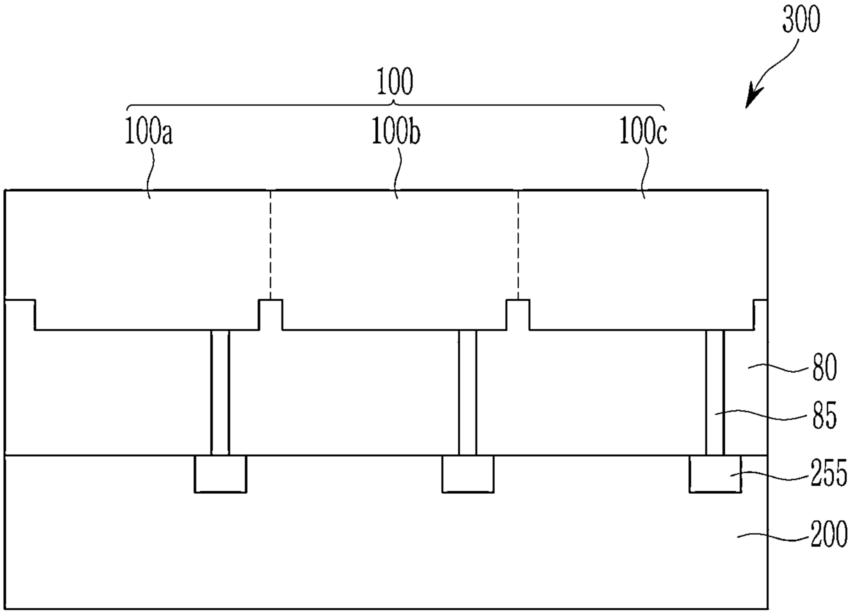
FIG. 8 is a cross-sectional view showing an example of the image sensor of FIG. 7.

FIG. 7 is a plan view showing an image sensor according to some example embodiments, and FIG. 8 is a cross-sectional view showing an example of the image sensor of FIG. 7.

Referring to FIGS. 7 and 8, the image sensor 300 includes the sensor 100 on the substrate 200, and the sensor 100 includes the first, second, and third sensors 100*a*, 100*b*, and 100*c*. The first, second, and third sensors 100*a*, 100*b*, and 100*c* may be configured to convert light of different wavelength spectra (e.g., blue light, green light, or red light) into electrical signals.

Referring to FIG. 8, the first, second, and third sensors 100*a*, 100*b*, and 100*c* are arranged in a parallel direction (e.g., surface direction of the substrate 200) to the surface of the substrate 200 unlike some example embodiments, including the example embodiments shown in FIGS. 5 and 6. Each first, second, and third sensor 100*a*, 100*b*, and 100*c* is electrically connected to the charge storage 255 integrated in the substrate 200 through the trench 85.

For example, the aforementioned sensor 100 may be included in a display panel, and may be, for example, applied to a sensor-embedded display panel in which the sensor 100 is embedded in the display panel.

Hereinafter, a sensor-embedded display panel including the aforementioned sensor is described.

The sensor-embedded display panel according to some example embodiments may be a display panel capable of performing a display function and a recognition function (e.g., biometric recognition function), and may be an in-cell type display panel in which a sensor performing a recognition function (e.g., biometric recognition function) is embedded in the display panel.

Figure 9:
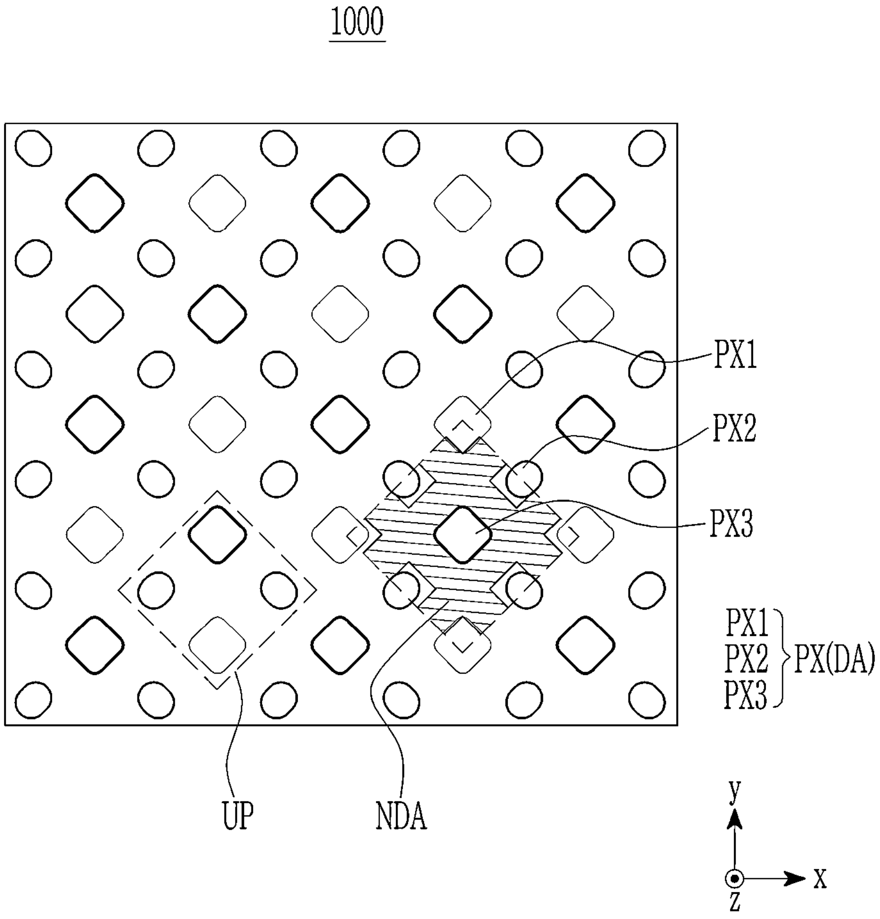
FIG. 9 is a plan view illustrating an example of a sensor-embedded display panel according to some example embodiments.
Figure 10:
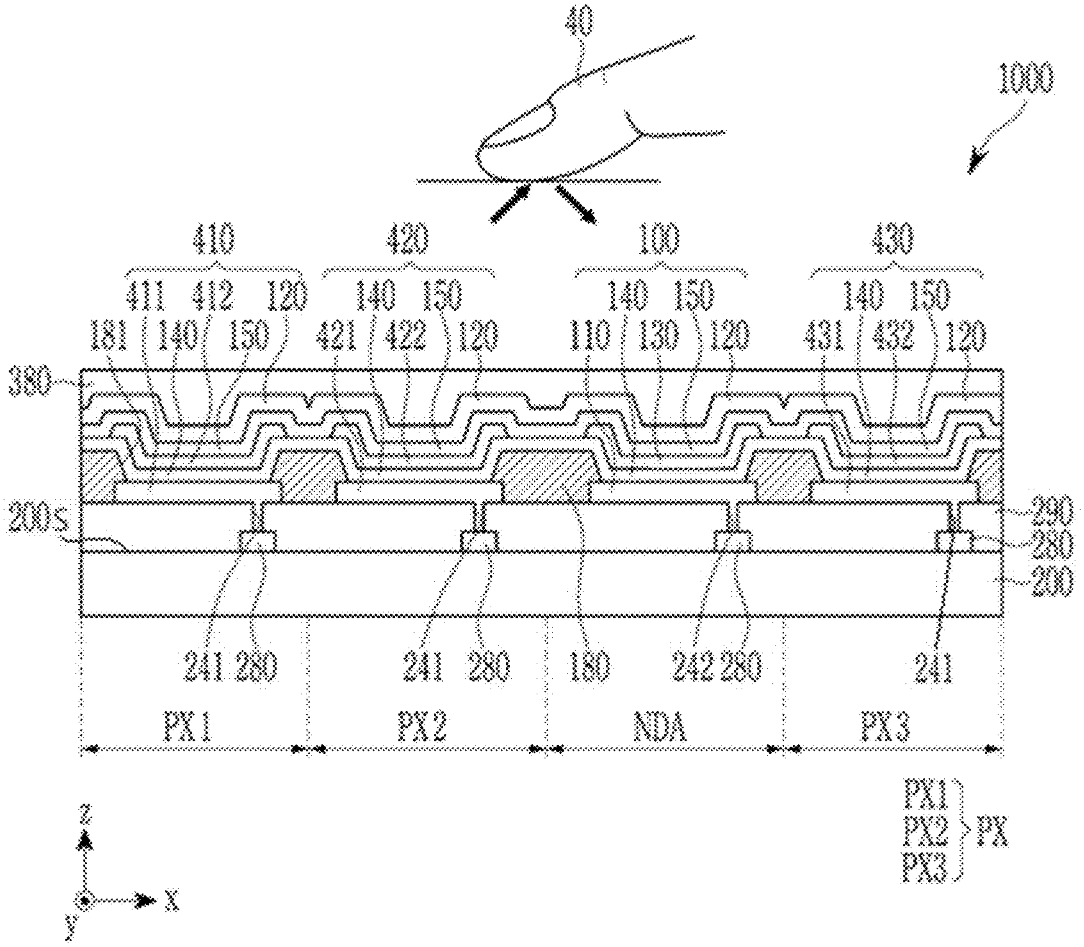
FIG. 10 is a cross-sectional view illustrating an example of a sensor-embedded display panel according to some example embodiments.

FIG. 9 is a plan view illustrating an example of a sensor-embedded display panel according to some example embodiments, and FIG. 10 is a cross-sectional view illustrating an example of a sensor-embedded display panel according to some example embodiments.

Referring to FIGS. 9 and 10, a sensor-embedded display panel 1000 according to some example embodiments includes a plurality of subpixels PX's displaying (e.g., configured to display) different colors from each other. The plurality of subpixels PX's may be configured to display at least three primary colors, for example, a first subpixel PX1, a second subpixel PX2, and a third subpixel PX3 configured to display different first color, second color, and third color selected from red, green, and blue. For example, the first color, the second color, and the third color may be red, green, and blue, respectively. The first subpixel PX1 may be a red subpixel configured to display red, the second subpixel PX2 may be a green subpixel configured to display green, and the third subpixel PX3 may be a blue subpixel configured to display blue. However, the present inventive concepts are not limited thereto, and an auxiliary subpixel (not shown) such as a white subpixel may be further included. Displaying a color may refer to emitting light corresponding to the color (e.g., light in a wavelength spectrum of the color). Referring to FIG. 9, the sensor embedded display panel 1000 may include a plurality of first subpixels (PX1) configured to display a red color (e.g., light of a red wavelength spectrum) and including a first light emitting element (e.g., the first light emitting element 410 shown in FIG. 10), a plurality of second subpixels (PX2) configured to display a green color (e.g., light of a green wavelength spectrum) and including a second light emitting element (e.g., the second light emitting element 420 shown in FIG. 10), and a plurality of third subpixels (PX3) configured to display a blue color (e.g., light of a blue wavelength spectrum) and including a third light emitting element (e.g., the third light emitting element 430 shown in FIG. 10), where the first subpixels (PX1), the second subpixels (PX2), and the third subpixels (PX3) are located in and/or at least partially define the display area (DA).

The plurality of subpixels PX's including the first subpixel PX1, the second subpixel PX2, and the third subpixel PX3 may constitute (e.g., may define) one unit pixel UP to be arranged repeatedly along the row and/or column. In FIG. 9, a structure including one first subpixel PX1, two second subpixels PX2, and one third subpixel PX3 in the unit pixel UP is illustrated, but the present inventive concepts are not limited thereto. At least one first subpixel PX1, at least one second subpixel PX2, and at least one third subpixel PX3 may be included. In the drawing of FIGS. 9 and 10, as an example, an arrangement of a Pentile type is illustrated, but the present inventive concepts are not limited thereto. The subpixels PX's may be arranged variously. An area occupied by the plurality of subpixels PX's and configured to display at least one color by the plurality of subpixels PX's may be a display area DA displaying an image. For example, the area (e.g., in the xy plane) of the subpixels (PX) may collectively define the display area (DA) that is configured to display an image thereon (e.g., configured to display one or more colors). A portion of the area (e.g., in the xy plane) of the sensor embedded display panel 1000 that excludes the display area (DA) (e.g., portions of the area of the sensor embedded display panel 1000 that are between adjacent subpixels (PX) in the xy direction, xy plane, etc.) may be a non-display area (NDA) that is configured to not display an image thereon (e.g., configured to not display any color).

Each of the first subpixel PX1, the second subpixel PX2, and the third subpixel PX3 may include a light emitting element. As an example, the first subpixel PX1 may include a first light emitting element 410 configured to emit light of a wavelength spectrum of a first color, the second subpixel PX2 may include a second light emitting element 420 configured to emit light of a wavelength spectrum of a second color, and the third subpixel PX3 may include a third light emitting element 430 configured to emit light having a wavelength spectrum of a third color. However, the present inventive concepts are not limited thereto, and at least one of the first subpixel PX1, the second subpixel PX2, or the third subpixel PX3 may include a light emitting element configured to emit light of a combination of a first color, a second color, and a third color, that is, light in a white wavelength spectrum, and may display a first color, a second color, or a third color through a color filter (not shown).

The sensor-embedded display panel 1000 according to some example embodiments includes the aforementioned sensor 100. The sensor 100 may be disposed in a non-display area NDA. The non-display area NDA may be an area other than the display area DA, in which the first subpixel PX1, the second subpixel PX2, the third subpixel PX3, and auxiliary subpixels are not arranged (e.g., a portion of the total area of the sensor embedded display panel 1000 that excludes the display area (DA), excludes the subpixels (PX), is between adjacent subpixels (PX), etc.). For example, the area (e.g., in the xy plane) of the subpixels (PX) may collectively define the display area (DA) that is configured to display an image thereon (e.g., configured to display one or more colors). A portion of the area (e.g., in the xy plane) of the sensor embedded display panel 1000 that excludes the display area (DA) (e.g., portions of the area of the sensor embedded display panel 1000 that are between adjacent subpixels (PX) in the xy direction, xy plane, etc.) may be a non-display area (NDA) that is configured to not display an image thereon (e.g., configured to not display any color). The sensor 100 may be between at least two subpixels selected from the first subpixel PX1, the second subpixel PX2, and the third subpixel PX3 (e.g., between at least two subpixels of a first subpixel PX1 of a plurality of first subpixels PX1, a second subpixel PX2 of the plurality of second subpixels PX2, or a third subpixel PX3 of the plurality of third subpixels PX3), and may be in parallel with the first, second, and third light emitting elements 410, 420, and 430 in the display area DA for example in parallel along the in-plane direction of the substrate 200 (e.g., the xy direction as shown), which may be a direction extending parallel to an upper surface 200S of the substrate 200.

The sensor 100 may be an optical type recognition sensor (e.g., biometric sensor). The sensor 100 may be configured to absorb light generated by reflection of light emitted from at least one of the first, second or third light emitting elements 410, 420, or 430 in the display area DA, by a recognition target 40 such as a living body, a tool, or a thing (e.g., may be configured to absorb light of a red wavelength spectrum, a green wavelength spectrum, a blue wavelength spectrum, or any combination thereof), and then may be configured to convert the absorbed light into an electrical signal. Herein, the living body may be a finger, a fingerprint, a palm, an iris, a face, and/or a wrist, but is not limited thereto. The sensor 100 may be, for example, a fingerprint sensor, an illumination sensor, an iris sensor, a distance sensor, a blood vessel distribution sensor, and/or a heart rate sensor, but is not limited thereto.

The sensor 100 may be on the same plane as the first, second, and third light emitting elements 410, 420, and 430 on the substrate 200, and may be embedded in the sensor-embedded display panel 1000. Restated, the sensor 100 may be in parallel with the first, second, and third light emitting elements 410, 420, and 430 on the substrate 200 along an in-plane direction of the substrate 200. As described herein, the in-plane direction of the substrate 200 may be a direction (e.g., the xy direction as shown) that extends in parallel with at least a portion of the substrate 200, including an upper surface 200S of the substrate 200.

Referring to FIG. 10, the sensor-embedded display panel 1000 includes a substrate 200; a thin film transistor 280 on the substrate 200; an insulation layer 290 on thin film transistor 280; a pixel definition layer 180 on the insulation layer 290; and first, second, or third light emitting elements 410, 420, and 430 and the sensor 100 in a space partitioned by the pixel definition layer 180.

The substrate 200 may be a light-transmitting substrate, for example, a glass substrate or a polymer substrate. The polymer substrate may include, for example, polycarbonate, polymethylmethacrylate, polyethyleneterephthalate, polyethylenenaphthalate, polyimide, polyamide, polyamideimide, polyethersulfone, polyorganosiloxane, styrene-ethylene-butylene-styrene, polyurethane, polyacryl, polyolefin, or any combination thereof, but is not limited thereto.

A plurality of thin film transistors 280 are formed on the substrate 200. One or more thin film transistor 280 may be included in each subpixel PX, and may include, for example, at least one switching thin film transistor and/or at least one driving thin film transistor. The substrate 200 on which the thin film transistor 280 is formed may be referred to as a thin film transistor substrate (TFT substrate) or a thin film transistor backplane (TFT backplane).

The insulation layer 290 may cover the substrate 200 and the thin film transistor 280 and may be formed on the whole surface of the substrate 200. The insulation layer 290 may be a planarization layer or a passivation layer, and may include an organic insulating material, an inorganic insulating material, an organic-inorganic insulating material, or any combination thereof. The insulation layer 290 may have a plurality of contact holes 241 for electrically connecting the first, second, and third light emitting elements 410, 420, and 430 and the thin film transistor 280 and a plurality of contact holes 242 for electrically connecting the sensor 100 and the thin film transistor 280. The insulation layer 290 may include an organic, inorganic, or organic-inorganic insulating material, in some example embodiments, an inorganic insulating material such as silicon oxide, silicon nitride, silicon oxynitride, aluminum oxide, aluminum nitride, or aluminum oxynitride; an organic insulating material such as polyimide, polyamide, polyamideimide, or polyacrylate; or an organic-inorganic insulating material such as polyorganosiloxane or polyorganosilazane.

The pixel definition layer 180 may also be formed on the whole surface of the substrate 200 and may be between adjacent subpixels PX's to partition each subpixel PX. The pixel definition layer 180 may have a plurality of openings 181 in each subpixel PX, and in each opening 181, any one of the first, second, or third light emitting elements 410, 420, or 430 or the sensor 100 may be disposed. The pixel definition layer 180 be an insulation layer that may include an organic, inorganic, or organic-inorganic insulating material, in some example embodiments, an inorganic insulating material such as silicon oxide, silicon nitride, or silicon oxynitride; an organic insulating material such as polyimide; or an organic-inorganic insulating material such as polyorganosiloxane or polyorganosilazane.

The first, second and third light emitting elements 410, 420, and 430 are formed on the substrate 200 (or thin film transistor substrate), and are repeatedly arranged along the surface direction (e.g., xy direction) of the substrate 200. As described above, the first, second, and third light emitting elements 410, 420, and 430 may be included in the first subpixel PX1, the second subpixel PX2, and the third subpixel PX3, respectively. The first, second, and third light emitting elements 410, 420, and 430 may be electrically connected to separate thin film transistors 280 and may be driven independently.

The first, second and third light emitting elements 410, 420, and 430 may be configured to each independently emit light of one selected from a red wavelength spectrum, a green wavelength spectrum, a blue wavelength spectrum, and any combination thereof. For example, the first light emitting element 410 may be configured to emit light of a red wavelength spectrum, the second light emitting element 420 may be configured to emit light of a green wavelength spectrum, and the third light emitting element 430 may be configured to emit light of a blue wavelength spectrum. Herein, the red wavelength spectrum, the green wavelength spectrum, and the blue wavelength spectrum may have a maximum emission wavelength (Amax) in a wavelength spectrum of greater than about 600 nm and less than about 750 nm, about 500 nm to about 600 nm, and greater than or equal to about 400 nm and less than about 500 nm, respectively.

The first, second, and third light emitting elements 410, 420, and 430 may be, for example, light emitting diodes, for example, an organic light emitting diode including an organic material, an inorganic light emitting diode including an inorganic material, a quantum dot light emitting diode including quantum dots, or a perovskite light emitting diode including perovskite.

The sensor 100 may be formed on the substrate 200 (or the thin film transistor substrate), and may be randomly or regularly arranged along the surface direction (e.g., xy direction) of the substrate 200. As described above, the sensor 100 may be in the non-display area NDA, and may be connected to a separate thin film transistor 280 to be independently driven. The sensor 100 may be configured to absorb light of the same wavelength spectrum as the light emitted from at least one of the first, second, or third light emitting elements 410, 420, or 430 to convert the absorbed light into an electrical signal. For example, it may be configured to absorb light of a red wavelength spectrum, a green wavelength spectrum, a blue wavelength spectrum, or any combination thereof to convert the absorbed light into an electrical signal. The sensor 100 may be, for example, a photoelectric conversion diode and may be, for example, an organic photoelectric conversion diode including an organic material.

Each of the first, second, and third light emitting elements 410, 420, and 430 and the sensor 100 may include separate, respective pixel electrodes 411, 421, 431, and 110; a separate portion of a common electrode 120 facing the pixel electrodes 411, 421, 431, and 110 and to which a common voltage is applied; and separate, respective light emitting layers 412, 422, and 432 or a photoelectric conversion layer 130, a separate portion of a first common auxiliary layer 140, and a separate portion of a second common auxiliary layer 150 between the pixel electrodes 411, 421, 431, and 110 and the common electrode 120. The pixel electrode 110 of the sensor 100 may correspond to the first electrode 110 of the aforementioned sensor 100, the common electrode 120 of the sensor 100 may correspond to the second electrode 120 of the aforementioned sensor 100, and the first and second common auxiliary layers 140 and 150 may correspond to the first and second common auxiliary layers 140 and 150 of the aforementioned sensor 100.

The first, second, and third light emitting elements 410, 420, and 430 and the sensor 100 may be arranged in parallel along the surface direction (e.g., xy direction) of the substrate 200, and the common electrode 120, the first common auxiliary layer 140, and the second common auxiliary layer 150 which are formed on the whole surface may be shared. For example, as shown in at least FIG. 10, the photoelectric conversion layer 130 of the sensor 100 and the light emitting layers 412, 422, and 432 of the first, second, and third light emitting elements 410, 420, and 430 may at least partially overlap with each other (e.g., partially or completely overlap each other) in the in-plane direction (e.g., xy direction) of the substrate 200, which may be understood to be a horizontal direction that extends in parallel to an in-plane direction of the substrate 200 as shown in FIG. 10 and/or a horizontal direction that extends in parallel to an upper surface 200S of the substrate 200 as shown in FIG. 10, and the photoelectric conversion layer 130 and the light emitting layers 412, 422, and 432 may be at least partially positioned on the same plane (e.g., an xy plane extending in the xy directions that intersects each of the photoelectric conversion layer 130 and the light emitting layers 412, 422, and 432).

The common electrode 120 is continuously formed as a single piece of material that extends on the upper portion of the light emitting layers 412, 422, and 432 and the photoelectric conversion layer 130, and is substantially formed on the whole surface of the substrate 200. The common electrode 120 may apply a common voltage to the first, second, and third light emitting elements 410, 420, and 430 and the sensor 100. As shown, the first, second, and third light emitting elements 410, 420, and 430 and the sensor 100 may include separate portions of a single common electrode 120 that is a single piece of material that extends on each of the respective light emitting layers 412, 422, and 432 and the photoelectric conversion layer 130 and between the first, second, and third light emitting elements 410, 420, and 430 and the sensor 100.

The first common auxiliary layer 140 is between the pixel electrodes 411, 421, 431, and 110 and the light emitting layers 412, 422, 432 and the photoelectric conversion layer 130, and may be continuously formed as a single piece of material that extends on the pixel electrodes 411, 421, 431, and 110, and under the light emitting layers 412, 422, and 432 and the photoelectric conversion layer 130. As shown, the first, second, and third light emitting elements 410, 420, and 430 and the sensor 100 may include separate portions of a single first common auxiliary layer 140 that is a single piece of material that extends on each of the respective light emitting layers 412, 422, and 432 and the photoelectric conversion layer 130 and between the first, second, and third light emitting elements 410, 420, and 430 and the sensor 100.

The first common auxiliary layer 140 is a charge auxiliary layer (e.g., hole auxiliary layer) that facilitates injection and/or transport of electric charges (e.g., holes) from the pixel electrodes 411, 421, and 431 to the light emitting layers 412, 422, and 432.

For example, the HOMO energy level of the first common auxiliary layer 140 may be between the HOMO energy level of the light emitting layers 412, 422, and 432 and the work function of the pixel electrodes 411, 421, and 431. The work function of the pixel electrodes 411, 421, and 431, the HOMO energy level of the first common auxiliary layer 140, and the HOMO energy level of the light emitting layers 412, 422, and 432 may be sequentially deepened (e.g., sequentially larger in relation to a vacuum level (e.g., 0 eV)). On the other hand, the LUMO energy level of the first common auxiliary layer 140 may be shallower (e.g., smaller in relation to a vacuum level (e.g., 0 eV), closer to the vacuum level of 0 eV, etc.) than the LUMO energy level of the photoelectric conversion layer 130 and the work function of the pixel electrode 110, respectively.

The first common auxiliary layer 140 may include an organic material, an inorganic material, an organic-inorganic material, or any combination thereof satisfying the HOMO energy level, for example a phthalocyanine compound such as copper phthalocyanine; DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino]triphenylamine), TDATA (4,4'4"-tris(N,N-diphenylamino)triphenylamine), 2-TNATA (4,4',4"-tris{N-(2-naphthyl)-N-phenylamino}-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/Camphor sulfonic acid), PANI/PSS (polyaniline/poly(4-styrenesulfonate)), NPB (N,N'-di(naphthalen-1-yl)-N,N'-diphenylbenzidine), polyetherketone including triphenylamine (TPAPEK), 4-isopropyl-4'-methyldiphenyliodonium[tetrakis(pentafluorophenyl)borate], HAT-CN (dipyrazino[2,3-f: 2',3'-h]quinoxaline-2,3,6,7,10,11-hexacarbonitrile), a carbazole-based derivative such as N-phenylcarbazole, polyvinylcarbazole, and the like, a fluorene-based derivative, TPD (N,N'-bis(3-methylphenyl)-N,N'-diphenyl-[1,1-biphenyl]-4,4'-diamine), a triphenylamine-based derivative such as TCTA (4,4',4"-tris(N-carbazolyl)triphenylamine), NPB (N,N'-di(naphthalen-1-yl)-N,N'-diphenylbenzidine), TAPC (4,4'-cyclohexylidene bis[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), or any combination thereof, but is not limited thereto. The first common auxiliary layer 140 may be one layer or two or more layers.

The second common auxiliary layer 150 may be between the light emitting layers 412, 422, and 432 and the photoelectric conversion layer 130, and the common electrode 120. The second common auxiliary layer 150 may be continuously formed as a single piece of material that extends on the light emitting layers 412, 422, and 432, and the photoelectric conversion layer 130, and under the common electrode 120. As shown, the first, second, and third light emitting elements 410, 420, and 430 and the sensor 100 may include separate portions of a single second common auxiliary layer 150 that is a single piece of material that extends under each of the respective light emitting layers 412, 422, and 432 and the photoelectric conversion layer 130 and between the first, second, and third light emitting elements 410, 420, and 430 and the sensor 100.

The second common auxiliary layer 150 is a charge auxiliary layer (e.g., an electron auxiliary layer) that facilitates injection and/or transport of electric charges (e.g., electrons) from the common electrode 120 to the light emitting layers 412, 422, and 432. For example, the LUMO energy level of the second common auxiliary layer 150 may be between the LUMO energy level of the light emitting layers 412, 422, and 432 and the work function of the common electrode 120. The work function of the common electrode 120, the LUMO energy level of the second common auxiliary layer 150, and the LUMO energy level of the light emitting layers 412, 422, and 432 may become shallow in sequence (e.g., sequentially smaller in relation to 0 eV of a vacuum level).

The second common auxiliary layer 150 may include an organic material, an inorganic material, an organic-inorganic material, or any combination thereof satisfying the LUMO energy level, for example a halogenated metal such as LiF, NaCl, CsF, RbCl, and RbI; a lanthanides metal such as Yb; a metal oxide such as $Li_2C$ or BaO; Liq (lithium quinolate), Alq3 (tris(8-hydroxyquinolinato)aluminum), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-ylphenyl)-9,10-dinaphthylanthracene, TPBi (1,3,5-tri(1-phenyl-1H-benzo[d]imidazol-2-yl)phenyl), BCP (2,9- dimethyl-4,7-diphenyl-1,10-phenanthroline), Bphen (4,7-diphenyl-1,10-phenanthroline), TAZ (3-(4-biphenylyl)-4-phenyl-5-tertbutylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,O8)-(1,1'-biphenyl-4-olato)aluminum), $Bebq_2$ (berylliumbis (benzoquinolin-10-olate), ADN (9,10-di(naphthalene-2-yl) anthracene), BmPyPhB (1,3-bis[3,5-di(pyridin-3-yl)phenyl] benzene), or any combination thereof, but is not limited thereto. The first common auxiliary layer 140 may be one layer or two or more layers.

Each of the first, second, and third light emitting elements 410, 420, and 430 and the sensor 100 may include a separate pixel electrode 411, 421, 431, or 110 facing the common electrode 120. One of the pixel electrodes 411, 421, 431, and 110 or the common electrode 120 is an anode and the other is a cathode. For example, the pixel electrodes 411, 421, 431, and 110 may be an anode and the common electrode 120 may be a cathode. The pixel electrodes 411, 421, 431, and 110 are separated for each subpixel PX, and may be electrically connected to a separate thin film transistor 280 to be independently driven.

The pixel electrodes 411, 421, 431, and 110 and the common electrode 120 may each be a light-transmitting electrode or a reflective electrode, and for example, at least one of the pixel electrodes 411, 421, 431, and 110 or the common electrode 120 may be a light-transmitting electrode.

For example, when the pixel electrodes 411, 421, 431, and 110 are light-transmitting electrodes and the common electrode 120 is a reflective electrode, the sensor-embedded display panel 1000 may be a bottom emission type display panel configured to emit light toward the substrate 200. For example, when the pixel electrodes 411, 421, 431, and 110 are reflective electrodes and the common electrode 120 are light-transmitting electrode, the sensor-embedded display panel 1000 may be a top emission type display panel configured to emit light to the opposite side of the substrate 200. For example, when the pixel electrodes 411, 421, 431, and 110 and the common electrode 120 are light-transmitting electrodes, respectively, the sensor-embedded display panel 1000 may be a both side emission type display panel.

For example, the pixel electrodes 411, 421, 431, and 110 may be reflective, electrodes and the common electrode 120 may be a semi-transmissive electrode. In this case, the sensor-embedded display panel 1000 may have a microcavity structure. In the microcavity structure, reflection may occur repeatedly between the reflective electrode and the semi-transmissive electrode separated by a particular (or, alternatively, predetermined) optical length (e.g., a distance between the semi-transmissive electrode and the reflective electrode) and light of a particular (or, alternatively, predetermined) wavelength spectrum may be enhanced to improve optical properties.

For example, among the light emitted from the light emitting layers 412, 422, and 432 of the first, second, and third light emitting elements 410, 420, and 430, light of a particular (or, alternatively, predetermined) wavelength spectrum may be repeatedly reflected between the semi-transmissive electrode and the reflective electrode and then may be modified. Among the modified light, light having a wavelength spectrum corresponding to a resonance wavelength of a microcavity may be enhanced to exhibit amplified light emission characteristics in a narrow wavelength spectrum. Accordingly, the sensor-embedded display panel 1000 may express colors with high color purity.

For example, among the light incident on the sensor 100, light of a particular (or, alternatively, predetermined) wavelength spectrum may be repeatedly reflected between the semi-transmissive electrode and the reflective electrode to be modified. Among the modified light, light having a wavelength spectrum corresponding to the resonance wavelength of a microcavity may be enhanced to exhibit photoelectric conversion characteristics amplified in a narrow wavelength spectrum. Accordingly, the sensor 100 may exhibit high photoelectric conversion characteristics in a narrow wavelength spectrum.

Each of the first, second, and third light emitting elements 410, 420, and 430 includes light emitting layers 412, 422, and 432 between the pixel electrodes 411, 421, and 431 and the common electrode 120. Each of the light emitting layer 412 included in the first light emitting element 410, the light emitting layer 422 included in the second light emitting element 420, and the light emitting layer 432 included in the third light emitting element 430 may be configured to emit light in the same or different wavelength spectra and may be configured to emit light in, for example a red wavelength spectrum, a green wavelength spectrum, a blue wavelength spectrum, or any combination thereof.

For example, when the first light emitting element 410, the second light emitting element 420, and the third light emitting element 430 are a red light emitting elements, a green light emitting element, and a blue light emitting element, respectively, the light emitting layer 412 may be a red light emitting layer configured to emit light in a red wavelength spectrum, the light emitting layer 422 included in the second light emitting element 420 may be a green light emitting layer configured to emit light in a green wavelength spectrum, and the light emitting layer 432 included in the third light emitting element 430 may be a blue light emitting layer configured to emit light in a blue wavelength spectrum. Herein, the red wavelength spectrum, the green wavelength spectrum, and the blue wavelength spectrum may have a maximum emission wavelength in a wavelength spectrum of greater than about 600 nm and less than about 750 nm, about 500 nm to about 600 nm, and greater than or equal to about 400 nm and less than about 500 nm, respectively.

For example, when at least one of the first light emitting element 410, the second light emitting element 420, or the third light emitting element 430 is a white light emitting element, the light emitting layer of the white light emitting element may be configured to emit light of a full visible light wavelength spectrum, for example, light in a wavelength spectrum of greater than or equal to about 380 nm and less than about 750 nm, about 400 nm to about 700 nm, or about 420 nm to about 700 nm.

The light emitting layers 412, 422, and 432 may include an organic light emitter, a quantum dot, a perovskite, or any combination thereof as a light emitter. For example, the light emitting layers 412, 422, and 432 may include an organic light emitter, and may include at least one host material and a fluorescent or phosphorescent dopant.

The organic light emitter may be, for example, perylene; rubrene; 4-(dicyanomethylene)-2-methyl-6-[p-(dimethylamino)styryl]-4H-pyran; coumarin or a derivative thereof; carbazole or a derivative thereof; TPBi (2,2',2"-(1,3,5-benzinetriyl)-tris(1-phenyl-1-H-benzimidazole); TBADN (2-t-butyl-9,10-di(naphth-2-yl)anthracene); AND (9,10-di(naphthalene-2-yl)anthracene); CBP (4,4'-bis(N-carbazolyl)-1,1'-biphenyl); TCTA (4,4',4"-tris(carbazol-9-yl)-triphenylamine); TPBi (1,3,5-tris(N-phenylbenzimidazole-2-yl)benzene); TBADN (3-tert-butyl-9,10-di(naphth-2-yl) anthracene); DSA (distyrylarylene); CDBP (4,4'-dimethylbiphenyl); MADN (2-methyl-9,10-bis(naphthalen-2-yl)anthracene); TCP (1,3,5-tris(carbazol-9-yl)benzene); Alq3 (tris (8-hydroxyquinolino)lithium); an organometallic compound including Pt, Os, Ti, Zr, Hf, Eu, Tb, Tm, Rh, Ru, Re, Be, Mg, Al, Ca, Mn, Co, Cu, Zn, Ga, Ge, Pd, Ag, and/or Au, a derivative thereof or any combination thereof, but is not limited thereto.

The sublimation temperature of the known material that may be included in the light emitting layers 412, 422, and 432 may be less than or equal to about 380° C., and within the above range, less than or equal to about 370° C., less than or equal to about 360° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., less than or equal to about 250° C., about 100° C. to about 380° C., about 100° C. to about 370° C., about 100° C. to about 360° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 360° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

The quantum dot may include, for example, a Group II-VI semiconductor compound, a Group III-V semiconductor compound, a Group IV-VI semiconductor compound, a Group IV semiconductor element or compound, a Group I-III-VI semiconductor compound, a Group I-II-IV-VI semiconductor compound, a Group II-III-V semiconductor compound, or any combination thereof. The Group II-IV semiconductor compound may be, for example, selected from a binary element semiconductor compound selected from CdSe, CdTe, ZnS, ZnSe, ZnTe, ZnO, HgS, HgSe, HgTe, MgSe, MgS, or a mixture thereof; a ternary element semiconductor compound selected from CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, or a mixture thereof; and a quaternary element semiconductor compound selected from HgZnTeS, CdZnSeS, CdZnSeTe, CdZnSTe, CdHgSeS, CdHgSeTe, CdHgSTe, HgZnSeS, HgZnSeTe, HgZnSTe, or a mixture thereof, but is not limited thereto. The Group III-V semiconductor compound may be, for example, selected from a binary element semiconductor compound selected from GaN, GaP, GaAs, GaSb, AlN, AlP, AlAs, AlSb, InN, InP, InAs, InSb, or a mixture thereof; a ternary element semiconductor compound selected from GaNP, GaNAs, GaNSb, GaPAs, GaPSb, AlNP, AlNAs, AlNSb, AlPAs, AlPSb, InNP, InNAs, InNSb, InPAs, InPSb, or a mixture thereof; and a quaternary element semiconductor compound selected from GaAlNP, GaAlNAs, GaAlNSb, GaAlPAs, GaAlPSb, GainNP, GaInNAs, GaInNSb, GaInPAs, GaInPSb, InAlNP, InAlNAs, InAlNSb, InAlPAs, InAlPSb, or a mixture thereof, but is not limited thereto. The Group IV-VI semiconductor compound may be, for example, selected from a binary element semiconductor compound selected from SnS, SnSe, SnTe, PbS, PbSe, PbTe, or a mixture thereof; a ternary element semiconductor compound selected from SnSeS, SnSeTe, SnSTe, PbSeS, PbSeTe, PbSTe, SnPbS, SnPbSe, SnPbTe, or a mixture thereof; and a quaternary element semiconductor compound selected from SnPbSSe, SnPbSeTe, SnPbSTe, or a mixture thereof, but is not limited thereto. The Group IV semiconductor element or compound may be, for example, selected from a single-element semiconductor such as Si, Ge, or a mixture thereof; and a binary element compound selected from SiC, SiGe, or a mixture thereof, but is not limited thereto. The Group I-III-VI semiconductor compound may be, for example, $CuInSe_2$, $CuInS_2$, CulnGaSe, CulnGaS, or a mixture thereof, but is not limited thereto. The Group I-II-IV-VI semiconductor compound may be, for example, CuZnSnSe, CuZnSnS, or a mixture thereof, but is not limited thereto. The Group II-III-V semiconductor compound may be, for example, InZnP, but is not limited thereto.

The perovskite may be $CH_3NH_3PbBr_3$, $CH_3NH_3PbI_3$, $CH_3NH_3SnBr_3$, $CH_3NH_3SnI_3$, $CH_3NH_3Sn_{1-x}Pb_xBr_3$ ($0<x<1$), $CH_3NH_3Sn_{1-x}Pb_xI_3$ ($0<x<1$), $HC(NH_2)_2PbI_3$, $HC(NH_2)_2SnI_3$, $(C_4H_9NH_3)_2PbBr_4$, $(C_6H_5CH_2NH_3)_2PbBr_4$, $(C_6H_5CH_2NH_3)_2PbI_4$, $(C_6H_5C_2H_4NH_3)_2PbBr_4$, $(C_6H_{13}NH_3)_2(CH_3NH_3)_{n-1}Pb_nI_{3n+1}$, (n being any positive integer) any combination thereof, but is not limited thereto.

The sensor 100 includes a photoelectric conversion layer 130 between the pixel electrode 110 and the common electrode 120. The photoelectric conversion layer 130 is in parallel with the light emitting layers 412, 422, and 432 of the first, second, and third light emitting elements 410, 420, and 430 along the in-plane direction (e.g., xy direction) of the substrate 200. The photoelectric conversion layer 130 and the light emitting layers 412, 422, and 432 may be on the same plane. For example, as shown in at least FIG. 10, the photoelectric conversion layer 130 of the sensor 100 and the light emitting layers 412, 422, and 432 of the first, second, and third light emitting elements 410, 420, and 430 may at least partially overlap with each other (e.g., partially or completely overlap each other) in the in-plane direction (e.g., xy direction) of the substrate 200, which may be understood to be a horizontal direction that extends in parallel to an in-plane direction of the substrate 200 as shown in FIG. 10 and/or a horizontal direction that extends in parallel to an upper surface 200S of the substrate 200 as shown in FIG. 10, and the photoelectric conversion layer 130 and the light emitting layers 412, 422, and 432 may be at least partially positioned on the same plane (e.g., an xy plane extending in the xy directions that intersects each of the photoelectric conversion layer 130 and the light emitting layers 412, 422, and 432).

The photoelectric conversion layer 130 may be configured to absorb light of a particular (or, alternatively, predetermined) wavelength spectrum and convert the absorbed light into an electrical signal. The photoelectric conversion layer 130 may be configured to absorb light generated by reflection of the aforementioned light emitted from at least one of the first, second, or third light emitting elements 410, 420, or 430, by the recognition target 40 and may be configured to convert the absorbed light into an electrical signal. The photoelectric conversion layer 130 may be configured to absorb light of a red wavelength spectrum, a green wavelength spectrum, a blue wavelength spectrum, an infrared wavelength spectrum, or any combination thereof.

For example, the photoelectric conversion layer 130 may be configured to selectively absorb light of a red wavelength spectrum having a maximum absorption wavelength in a wavelength spectrum belonging to greater than about 600 nm and less than about 750 nm, and may be configured to absorb light generated by reflection of the light emitted from the red light emitting element among the first, second, and third light emitting elements 410, 420, and 430, by the recognition target 40.

For example, the photoelectric conversion layer 130 may be configured to selectively absorb light of a green wavelength spectrum having a maximum absorption wavelength in a wavelength spectrum belonging to about 500 nm to about 600 nm, and may be configured to absorb light generated by reflection of the light emitted from the green light emitting element among the first, second and third light emitting elements 410, 420, and 430, by the recognition target 40.

For example, the photoelectric conversion layer 130 may be configured to selectively absorb light in a blue wavelength spectrum having a maximum absorption wavelength in a wavelength spectrum belonging to greater than or equal to about 380 nm and less than about 500 nm, and may be configured to absorb light generated by reflection of the light emitted from the blue light emitting element among the first, second, and third light emitting elements 410, 420, and 430, by the recognition target 40.

For example, the photoelectric conversion layer 130 may be configured to absorb light of a red wavelength spectrum, a green wavelength spectrum, and a blue wavelength spectrum, that is, light of a full visible wavelength spectrum of greater than or equal to about 380 nm and less than about 750 nm. The photoelectric conversion layer 130 may be configured to absorb light generated by reflection of a combination of light emitted from the light emitting elements 410, 420, and 430, by the recognition target 40.

The photoelectric conversion layer 130 may include a p-type semiconductor and an n-type semiconductor that form a pn junction, and the p-type semiconductor and the n-type semiconductor are the same as described above. As described above, the photoelectric conversion layer 130 may include an intrinsic layer (I-layer) in which a p-type semiconductor and an n-type semiconductor are blended in a bulk heterojunction form, and in various combinations such as an I-layer, a p-type layer/I-layer, an I-layer/n-type layer, p-type layer/I-layer/n-type layer, or may include a bi-layer including a p-type layer including a p-type semiconductor and an n-type layer including the aforementioned n-type semiconductor. When the photoelectric conversion layer 130 is a bi-layer, the p-type layer may be close to (e.g., adjacent to) the pixel electrode 110 and the n-type layer may be close to (e.g., adjacent to) the common electrode 120.

The p-type semiconductor of the photoelectric conversion layer 130 may have an energy level capable of forming effective electrical matching with the first common auxiliary layer 140, and for example, a difference between a HOMO energy level of the first common auxiliary layer 140 and a HOMO energy level of the p-type semiconductor may be less than or equal to about 1.2 eV, within the above range, less than or equal to about 1.1 eV, less than or equal to about 1.0 eV, less than or equal to about 0.8 eV, less than or equal to about 0.7 eV, less than or equal to about 0.5 eV, about 0 eV to about 1.2 eV, about 0 eV to about 1.1 eV, about 0 eV to about 1.0 eV, about 0 eV to about 0.8 eV, about 0 eV to about 0.7 eV, about 0 eV to about 0.5 eV, about 0.01 eV to about 1.2 eV, about 0.01 eV to about 1.1 eV, about 0.01 eV to about 1.0 eV, about 0.01 eV to about 0.8 eV, about 0.01 eV to about 0.7 eV, or about 0.01 eV to about 0.5 eV. Accordingly, electric charges (e.g., holes) generated in the photoelectric conversion layer 130 may pass through the first common auxiliary layer 140 and may be effectively transported and/or extracted to the pixel electrode 110.

The n-type semiconductor of the photoelectric conversion layer 130 may include the aforementioned organic compound, and the n-type semiconductor and the second common auxiliary layer 150 may have an energy level capable of forming effective electrical matching. For example, a difference between the LUMO energy level of the second common auxiliary layer 150 and the LUMO energy level of the n-type semiconductor (the organic compound described above) may be less than or equal to about 1.2 eV, and within the above range, less than or equal to about 1.1 eV, less than or equal to about 1.0 eV, less than or equal to about 0.8 eV, less than or equal to about 0.7 eV, less than or equal to about 0.5 eV, about 0 eV to about 1.2 eV, about 0 eV to about 1.1 eV, about 0 eV to about 1.0 eV, about 0 eV to about 0.8 eV, about 0 eV to about 0.7 eV, about 0 eV to about 0.5 eV, about 0.01 eV to about 1.2 eV, about 0.01 eV to about 1.1 eV, about 0.01 eV to about 1.0 eV, about 0.01 eV to about 0.8 eV, about 0.01 eV to about 0.7 eV, or about 0.01 eV to about 0.5 eV. Accordingly, electric charges (e.g., electrons) generated in the photoelectric conversion layer 130 may pass through the second common auxiliary layer 150 and may be effectively transported and/or extracted to the common electrode 120.

A detailed description of the photoelectric conversion layer 130 is the same as described above.

For example, the light emitting layers 412, 422, and 432 may include an organic light emitting material as a light emitter, and the organic light emitting material of the light emitting layers 412, 422, and 432 and the p-type semiconductor and the n-type semiconductor of the photoelectric conversion layer 130 may be vacuum-deposited in the same chamber. Accordingly, a difference in sublimation temperatures between the organic light emitting material of the light emitting layers 412, 422, and 432 and the p-type semiconductor and the n-type semiconductor of the photoelectric conversion layer 130 may be less than or equal to about 150° C., and within the above range for example less than or equal to about 130° C., less than or equal to about 120° C., less than or equal to about 110° C., less than or equal to about 100° C., less than or equal to about 90° C., less than or equal to about 80° C., less than or equal to about 70° C., less than or equal to about 60° C., less than or equal to about 50° C., less than or equal to about 40° C., less than or equal to about 30° C., less than or equal to about 20° C., less than or equal to about 15° C., or less than or equal to about 10° C., within the above range, about 0° C. to about 150° C., about 0° C. to about 130° C., about 0° C. to about 120° C., about 0° C. to about 110° C., about 0° C. to about 100° C., about 0° C. to about 90° C., about 0° C. to about 80° C., about 0° C. to about 70° C., about 0° C. to about 60° C., about 0° C. to about 50° C., about 0° C. to about 40° C., about 0° C. to about 30° C., about 0° C. to about 20° C., about 0° C. to about 15° C., about 0° C. to about 10° C., about 2° C. to about 150° C., about 2° C. to about 130° C., about 2° C. to about 120° C., about 2° C. to about 110° C., about 2° C. to about 100° C., about 2° C. to about 90° C., about 2° C. to about 80° C., about 2° C. to about 70° C., about 2° C. to about 60° C., about 2° C. to about 50° C., about 2° C. to about 40° C., about 2° C. to about 30° C., about 2° C. to about 20° C., about 2° C. to about 15° C., or about 2° C. to about 10° C.

For example, the sublimation temperature of the organic light emitting materials of the light emitting layers 412, 422, and 432 and the p-type semiconductor and the n-type semiconductor of the photoelectric conversion layer 130 may be less than or equal to about 380° C., respectively, and within the above range, less than or equal to about 370° C., less than or equal to about 360° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., less than or equal to about 250° C., about 100° C. to about 380° C., about 100° C. to about 370° C., about 100° C. to about 360° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 360° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

In this way, since the p-type semiconductor and the n-type semiconductor of the photoelectric conversion layer 130 may form the aforementioned electrical matching with the first and second common auxiliary layers 140 and 150, and the light emitter (e.g., the organic light emitting materials) of the light emitting layers 412, 422, and 432 and the p-type semiconductor, and the n-type semiconductor of the photoelectric conversion layer 130 have similar thermal properties, the sensor may be effectively formed in the display panel without deterioration of electrical characteristics and complexity of the process.

The thickness of the light emitting layers 412, 422, and 432 and the thickness of the photoelectric conversion layer 130 may each independently be about 5 nm to about 300 nm, and within the above range, about 10 nm to about 250 nm, about 20 nm to about 200 nm, or about 30 nm to about 180 nm. A difference in thickness between the light emitting layers 412, 422, and 432 and the photoelectric conversion layer 130 may be less than or equal to about 20 nm, and within the above range, less than or equal to about 15 nm, less than or equal to about 10 nm, or less than or equal to about 5 nm, and the light emitting layers 412, 422, and 432 and the photoelectric conversion layer 130 may have substantially the same thickness. As described herein, a thickness of a layer, element or the like may be a thickness of the layer, element, or the like in a vertical direction that is perpendicular to the in-plane direction of the substrate 200, perpendicular to the upper surface 200S of the substrate 200, perpendicular to the xy direction (e.g., the z direction), or the like.

An encapsulation layer 380 is formed on the first, second, and third light emitting elements 410, 420, 430, and the sensor 100. The encapsulation layer 380 may include, for example, a glass plate, a metal thin film, an organic layer, an inorganic layer, an organic-inorganic layer, or any combination thereof. The organic film may include, for example, an acrylic resin, a (meth)acrylic resin, polyisoprene, a vinyl resin, an epoxy resin, a urethane resin, a cellulose resin, a perylene resin, or any combination thereof, but is not limited thereto. The inorganic film may include, for example, an oxides, a nitride, and/or an oxynitride, for example silicon oxide, silicon nitride, silicon oxynitride, aluminum oxide, aluminum nitride, aluminum oxynitride, zirconium oxide, zirconium nitride, zirconium oxynitride, titanium oxide, titanium nitride, titanium oxynitride, hafnium oxide, hafnium nitride, hafnium oxynitride, tantalum oxide, tantalum nitride, tantalum oxynitride, lithium fluoride, or any combination thereof, but is not limited thereto. The organic-inorganic film may include, for example, polyorganosiloxane, but is not limited thereto. The encapsulation layer 380 may be one layer or two or more layers.

As described above, the sensor-embedded display panel 1000 according to some example embodiments includes the first, second, and third light emitting elements 410, 420, and 430 configured to emit light of a particular (or, alternatively, predetermined) wavelength spectrum to display colors, and the sensor 100 configured to absorb light generated by reflection of the light, by the recognition target 40 and convert the absorbed light into an electrical signal, in the same in-plane on the substrate 200, thereby performing a display function and a recognition function (e.g., biometric recognition function) together. Accordingly, unlike conventional display panels formed on the outside of the display panel or formed under the display panel by manufacturing the sensor as a separate module, it may improve performance without increasing the thickness, implementing a slim-type high performance sensor-embedded display panel 1000.

In addition, since the sensor 100 uses light emitted from the first, second, and third light emitting elements 410, 420, and 430, the recognition function (e.g., biometric recognition function) may be performed without a separate light source. Therefore, it is not necessary to provide a separate light source outside the display panel, thereby preventing a decrease in the aperture ratio of the display panel due to the area occupied by the light source, and at the same time saving power consumed by the separate light source to improve power consumption.

In addition, as described above, the first, second, and third light emitting elements 410, 420, and 430 and the sensor 100 share the common electrode 120 (e.g., include separate portions of a common electrode 120 that is a single piece of material), the first common auxiliary layer 140 (e.g., include separate portions of a first common auxiliary layer 140 that is a single piece of material), and the second common auxiliary layer 150 (e.g., include separate portions of a second common auxiliary layer 150 that is a single piece of material) and thus the structure and process may be simplified compared with the case where the first, second, and third light emitting elements 410, 420, and 430 and the sensor 100 are formed in separate processes.

In addition, the sensor 100 may be an organic sensor including an organic photoelectric conversion layer, and accordingly, it may have a light absorbance that is two or more times higher than that of an inorganic diode such as a silicon photodiode, performing a high-sensitivity sensing function with further thinner thickness.

In addition, the sensor 100 may be anywhere in the non-display area NDA (e.g., anywhere in a portion of the sensor-embedded display panel 1000 that does not vertically overlap (e.g., in the z direction) within any light emitting elements and thus is not configured to emit light and/or display color), the sensor 100 may be at a desired location of the sensor-embedded display panel 1000 as many (e.g., as large of a quantity of sensors 100 in the non-display area NDA) as desired. Therefore, for example, by randomly or regularly arranging/distributing a plurality of sensors 100 over the entire area of the sensor-embedded display panel 1000, the biometric recognition function may be performed on any portion of the screen of an electronic device such as a mobile device and the biometric recognition function may be selectively performed only in a specific location where the biometric recognition function is required.

Hereinafter, another example of the sensor-embedded display panel 1000 according to some example embodiments is described.

Figure 11:
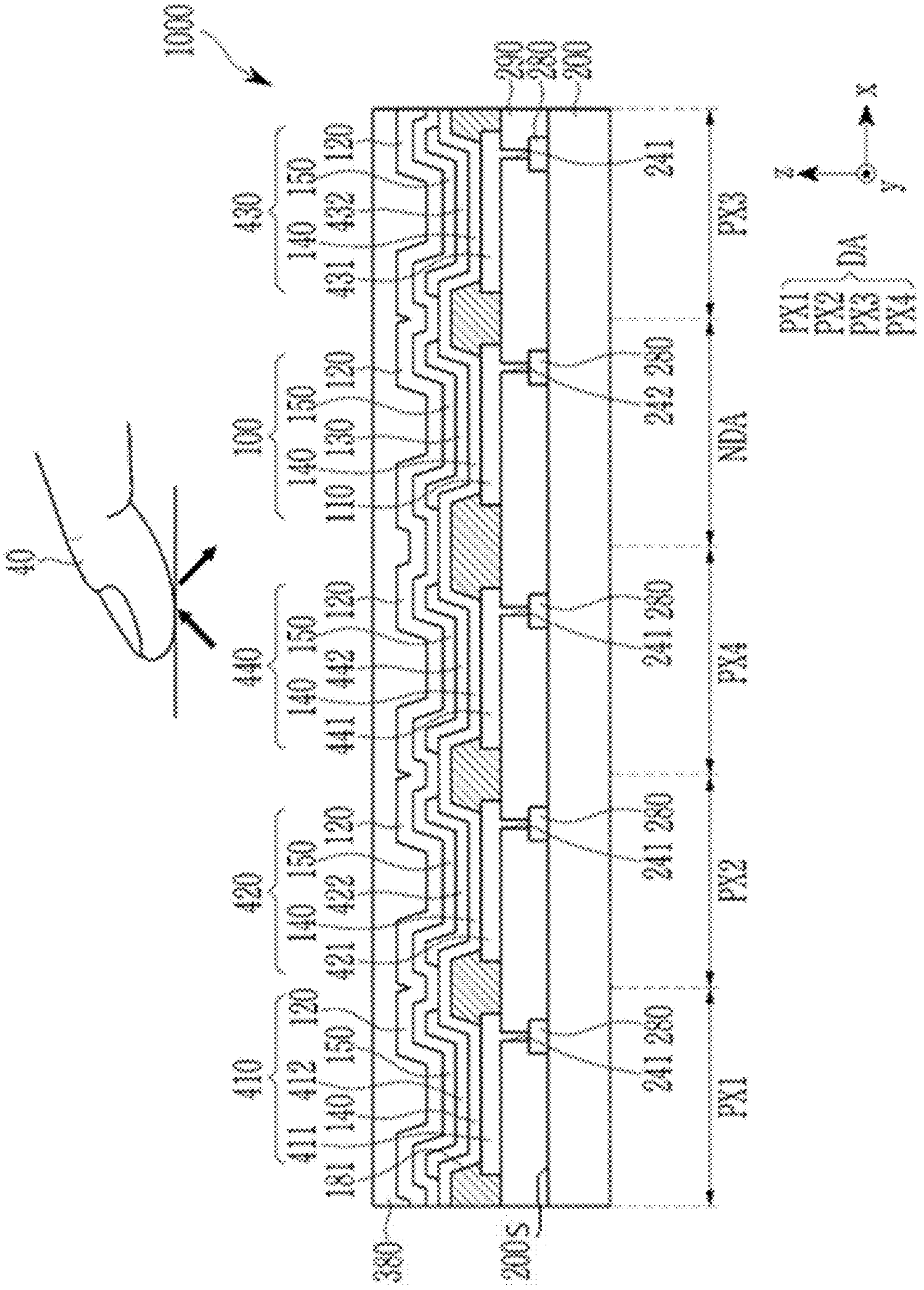
FIG. 11 is a cross-sectional view illustrating another example of a sensor-embedded display panel according to some example embodiments.

FIG. 11 is a cross-sectional view illustrating another example of a sensor-embedded display panel according to some example embodiments.

Referring to FIG. 11, a sensor-embedded display panel 1000 according to some example embodiments includes a plurality of subpixels PX configured to display different colors, that is, a first subpixel PX1, a second subpixel PX2, and a third subpixel PX3 configured to display a first color, a second color, and a third color selected from red, green, and blue, and the first subpixel PX1, the second subpixel PX2, and the third subpixel PX3 include a first light emitting element 410, a second light emitting element 420, and a third light emitting element 430, respectively, like some example embodiments, including the example embodiments shown in FIGS. 9 and 10.

However, unlike some example embodiments, including the example embodiments shown in FIGS. 9 and 10, the sensor-embedded display panel 1000 according to some example embodiments may further include the fourth light emitting element 440 configured to emit light in an infrared wavelength spectrum. For example, the fourth light emitting element 440 may be included in the fourth subpixel PX4 adjacent to the first subpixel PX1, the second subpixel PX2, and/or the third subpixel PX3, or may be included in a non-display area, NDA. The fourth subpixel PX4 may form one unit pixel UP together with the first subpixel PX1, the second subpixel PX2, and the third subpixel PX3, and the unit pixel UP may be arranged repeatedly along rows and/or columns.

Descriptions of the first subpixel PX1, the second subpixel PX2, the third subpixel PX3, the first light emitting element 410, the second light emitting element 420, the third light emitting element 430, and the sensor 100 are the same as described above.

The fourth light emitting element 440 is on the substrate 200 and may be on the same plane as the first, second, and third light emitting elements 410, 420, and 430 and the sensor 100. The fourth light emitting element 440 may be electrically connected to a separate thin film transistor 280 and driven independently. The fourth light emitting element 440 may have a structure in which the pixel electrode 441, the first common auxiliary layer 140, the light emitting layer 442, the second common auxiliary layer 150, and the common electrode 120 are sequentially stacked. Among them, the common electrode 120, the first common auxiliary layer 140, and the second common auxiliary layer 150 may be shared with the first, second, and third light emitting elements 410, 420, and 430 and the sensor 100. The light emitting layer 442 may be configured to emit light of an infrared wavelength spectrum, which may have for example a maximum emission wavelength in greater than or equal to about 750 nm, about 750 nm to about 20 μm, about 780 nm to about 20 μm, about 800 nm to about 20 μm, about 750 nm to about 15 μm, about 780 nm to about 15 μm, about 800 nm to about 15 μm, about 750 nm to about 10 μm, about 780 nm to about 10 μm, about 800 nm to about 10 μm, about 750 nm to about 5 μm, about 780 nm to about 5 μm, about 800 nm to about 5 μm, about 750 nm to about 3 μm, about 780 nm to about 3 μm, about 800 nm to about 3 μm, about 750 nm to about 2 μm, about 780 nm to about 2 μm, about 800 nm to about 2 μm, about 750 nm to about 1.5 μm, about 780 nm to about 1.5 μm, or about 800 nm to about 1.5 μm.

The sensor 100 may be configured to absorb light generated by reflection of light emitted from at least one of the first, second, third, or fourth light emitting elements 410, 420, 430, or 440, by a recognition target 40 such as a living body or a tool, and then convert the absorbed light into an electrical signal. For example, the sensor 100 may be configured to absorb light generated by reflection of light emitted from the fourth light emitting element 440 in an infrared wavelength spectrum, by the recognition target 40, and then convert the absorbed light into an electrical signal. In this case, the photoelectric conversion layer 130 of the sensor 100 may include an organic material, an inorganic material, an organic-inorganic material, or any combination thereof configured to selectively absorb light in the infrared wavelength spectrum. For example, the photoelectric conversion layer 130 may include a quantum dot, a quinoid metal complex compound, a polymethine compound, a cyanine compound, a phthalocyanine compound, a merocyanine compound, a naphthalocyanine compound, an immonium compound, a diimmonium compound, a triarylmethane compound, a dipyrromethene compound, an anthraquinone compound, a diquinone compound, a naphthoquinone compound, a squarylium compound, a rylene compound, a perylene compound, a squaraine compound, a pyrylium compound, a squaraine compound, a thiopyrylium compound, a diketopyrrolopyrrole compound, a boron dipyrromethene compound, a nickel-dithiol complex compound, a croconium compound, a derivative thereof, or any combination thereof, but is not limited thereto.

In some example embodiments, the sensor 100 may be provided separately from (e.g., independently of) a display panel of a sensor-embedded display panel 1000 and/or from any light emitting elements, for example as a separate component of an electronic device. For example, an electronic device, such as the electronic device 2000 shown in FIG. 13, may include a plurality of sensors 100, as a separate at least one additional device 1340, to serve as a camera for the electronic device separately from any light emitting elements and/or display panels of the electronic device 2000.

In some example embodiments, one or both of the first common auxiliary layer 140 and/or the second common auxiliary layer 150 may be absent from the sensor-embedded display panel 1000, and the photoelectric conversion layer 130 may be understood to be between (e.g., directly between) a pair of electrodes (e.g., pixel electrode 110 and a portion of the common electrode 120). In some example embodiments, the common electrode 120 may be replaced by a plurality of separate pixel electrodes that are each included in a separate one of the light emitting elements 410, 420, 430, and/or 440 and/or the sensor 100 and may face a separate pixel electrode 411, 421, 431, 441, and/or 110, such that the photoelectric conversion layer 130 may be understood to be between (e.g., directly between) a pair of electrodes that include the pixel electrode 110 and a separate electrode included in the sensor 100.

The sensor-embedded display panel 1000 according to some example embodiments includes the fourth light emitting element 440 configured to emit light in the infrared wavelength spectrum and the sensor 100 configured to absorb light in the infrared wavelength spectrum. Therefore, in addition to the biometric detection function, the sensitivity of the sensor 100 may be improved even in a low-illumination environment, and the detection capability of a 3D image may be further increased by widening a dynamic range for detailed division of black and white contrast. Accordingly, the sensing capability of the sensor-embedded display panel 1000 may be further improved. In particular, since light in the infrared wavelength spectrum may have a deeper penetration depth due to its long wavelength characteristics and information located at different distances may be effectively obtained, images or changes in blood vessels such as veins, iris and/or face, etc., in addition to fingerprints may be effectively detected, and the scope of application nay be further expanded.

The aforementioned sensor-embedded display panel 1000 may be applied to (e.g., included in) electronic devices such as various display devices. Electronic devices such as display devices may be applied to, for example, mobile phones, video phones, smart phones, smart pads, smart watches, digital-cameras, tablet PCs, laptop PCs, notebook computers, computer monitors, wearable computers, televisions, digital broadcasting terminals, e-books, personal digital assistants (PDAs), portable multimedia player (PMP), enterprise digital assistant (EDA), head mounted display (HMD), vehicle navigation, Internet of Things (IoT), Internet of all things (IoE), drones, door locks, safes, automatic teller machines (ATM), security devices, medical devices, or automotive electronic components, but are not limited thereto.

Figure 12:
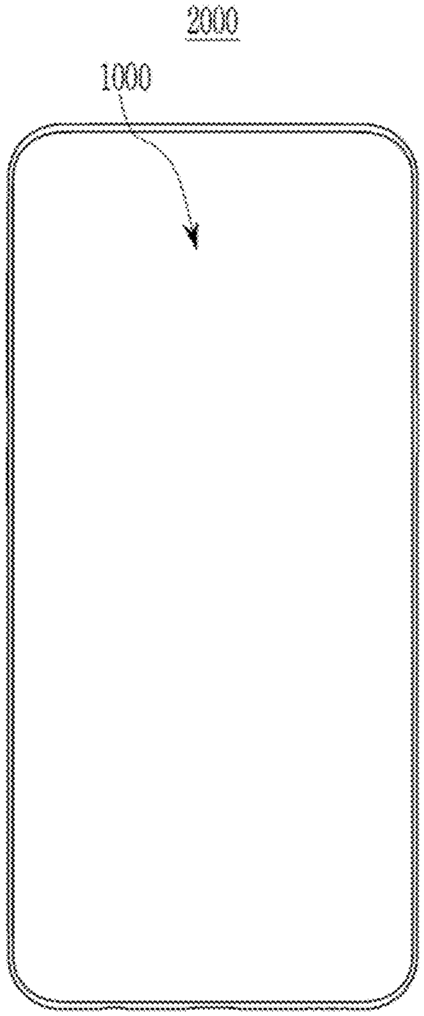
FIG. 12 is a schematic diagram illustrating an example of a smart phone as an electronic device according to some example embodiments.

FIG. 12 is a schematic view illustrating an example of a smart phone as an electronic device according to some example embodiments.

Referring to FIG. 12, the electronic device 2000 may include the aforementioned sensor-embedded display panel 1000, and the sensor 100 disposed in the whole or a part of the sensor-embedded display panel 1000, and thus a biometric recognition function may be performed on any part of the screen, and according to the user's selection, the biometric recognition function may be selectively performed only at a specific location where the biometric recognition function is required.

An example of a method of recognizing the recognition target 40 in an electronic device 2000 such as a display device may include, for example, driving the first, second, and third light emitting elements 410, 420, and 430 of the sensor-embedded display panel 1000 (or the first, second, third, and fourth light emitting elements 410, 420, 430, and 440) and the sensor 100 to detect the light reflected by the recognition target 40 among the light emitted from the first, second, and third light emitting elements 410, 420, and 430 (or the first, second, third and fourth light emitting element 410, 420, 430, and 440), in the sensor 100; comparing the image of the recognition target 40 stored in advance with the image of the recognition target 40 detected by the sensor 100; and judging the consistency of the compared images and if they match according to the determination that recognition of the recognition target 40 is complete, turning off the sensor 100, permitting user's access to the display device, and driving the sensor-embedded display panel 1000 to display an image.

Figure 13:
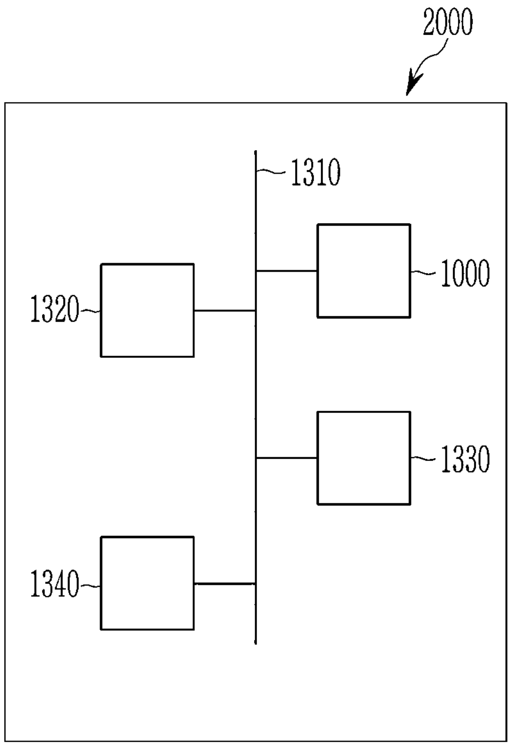
FIG. 13 is a schematic diagram illustrating an example of a configuration diagram of an electronic device according to some example embodiments.

FIG. 13 is a schematic view illustrating an example of a configuration diagram of an electronic device according to some example embodiments.

Referring to FIG. 13, in addition to the aforementioned constituent elements (e.g., the sensor-embedded display panel 1000), the electronic device 2000 may further include a bus 1310, a processor 1320, a memory 1330, and at least one additional device 1340. Information of the aforementioned sensor-embedded display panel 1000, processor 1320, memory 1330, and at least one additional device 1340 may be transmitted to each other through the bus 1310. In some example embodiments, the at least one additional device 1340 may be omitted. In some example embodiments, the sensor-embedded display panel 1000 may be replaced by a display device including, for example, exclusively light emitting elements and no light absorption sensors, while the at least one additional device 1340 may include one or a plurality (e.g., an array) of sensors according to any of the example embodiments which may serve as a biometric sensor, a camera, or the like.

The processor 1320 may include one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. As an example, the processing circuitry may include a non-transitory computer readable storage device. The processor 1320 may control, for example, a display operation of the sensor-embedded display panel 1000 or a sensor operation of the sensor 100.

The memory 1330 may be a non-transitory computer readable storage medium, such as, for example, as a solid state drive (SSD) and may store an instruction program (e.g., program of instructions), and the processor 1320 may perform a function related to the sensor-embedded display panel 1000 by executing the stored instruction program.

The at least one additional device 1340 may include one or more communication interfaces (e.g., wireless communication interfaces, wired interfaces), user interfaces (e.g., keyboard, mouse, buttons, etc.), power supply and/or power supply interfaces, or any combination thereof.

The units and/or modules described herein may be implemented using hardware constituent elements and software constituent elements. The units and/or modules described herein may include, may be included in, and/or may be implemented by one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. For example, the hardware constituent elements may include microphones, amplifiers, band pass filters, audio-to-digital converters, and processing devices. The processing device may be implemented using one or more hardware devices configured to perform and/or execute program code by performing arithmetic, logic, and input/output operations. The processing device may include a processor, a controller and an arithmetic logic unit, a digital signal processor, a microcomputer, a field programmable array, a programmable logic unit, a microprocessor, or any other device capable of responding to and executing instructions. The processing device may access, store, operate, process, and generate data in response to execution of an operating system (OS) and one or more software running on the operating system.

The software may include a computer program, a code, an instruction, or any combination thereof, and may transform a processing device for a special purpose by instructing and/or configuring the processing device independently or collectively to operate as desired. The software and data may be implemented permanently or temporarily as signal waves capable of providing or interpreting instructions or data to machines, parts, physical or virtual equipment, computer storage media or devices, or processing devices. The software may also be distributed over networked computer systems so that the software may be stored and executed in a distributed manner. The software and data may be stored by one or more non-transitory computer readable storage devices.

The method according to the foregoing embodiments may be recorded in a non-transitory computer readable storage device including program instructions for implementing various operations of some example embodiments. The storage device may also include program instructions, data files, data structures, and the like alone or in combination. The program instructions recorded in the storage device may be specially designed for some example embodiments or may be known to those skilled in computer software and available for use. Examples of non-transitory computer-readable storage devices may include magnetic media such as hard disks, floppy disks, and magnetic tapes; optical media such as CD-ROM discs, DVDs and/or blue-ray discs; magneto-optical media such as optical disks; and a hardware device configured to store and execute program instructions such as ROM, RAM, flash memory, and the like. The aforementioned device may be configured to operate as one or more software modules to perform the operations of some example embodiments.

Hereinafter, some example embodiments are illustrated in more detail with reference to examples. However, the scope of the inventive concepts are not limited to these examples.

SYNTHESIS EXAMPLES

Synthesis Example 1

[Compound 1AA]

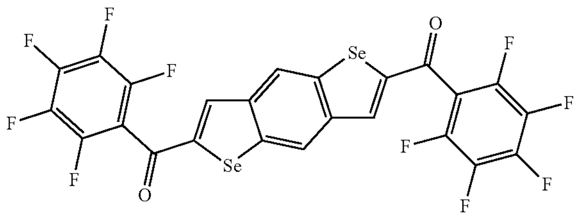

[Reaction Scheme 1]

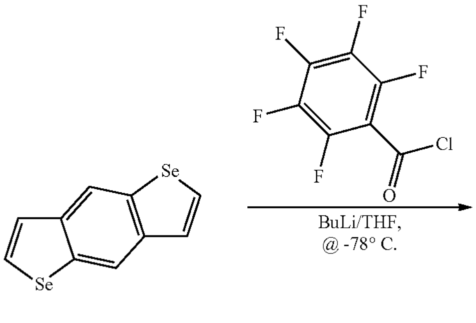

-continued

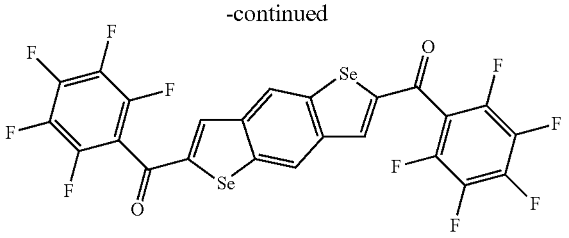

Benzo[1,2-b:4,5-b']diselenophene (2 g, 7.04 mmol) is dissolved in 40 mL of anhydrous tetrahydrofuran and then, cooled to 0° C. under a nitrogen atmosphere. Subsequently, an n-butyl lithium solution (2.5 M in hexane, 7 mL) is added thereto in a dropwise fashion and then, stirred for 1 hour. The resultant is cooled to −78° C., and pentafluorobenzoyl chloride (2.4 mL, 17.6 mmol) is slowly added thereto in a dropwise fashion. The obtained mixture is slowly heated up to room temperature, and water is added thereto, completing a reaction. Orange solids obtained therefrom are filtered and washed with water and acetone and dried, obtaining Compound 1AA. A yield thereof is 45%.

GC-MS (M+): 674

Synthesis Example 2

[Compound 1AB]

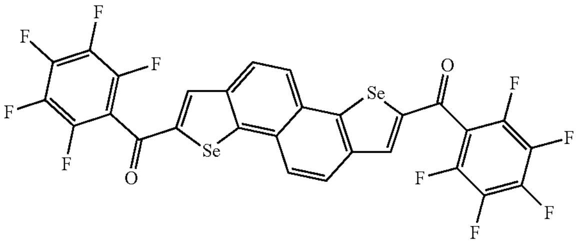

[Reaction Scheme 2]

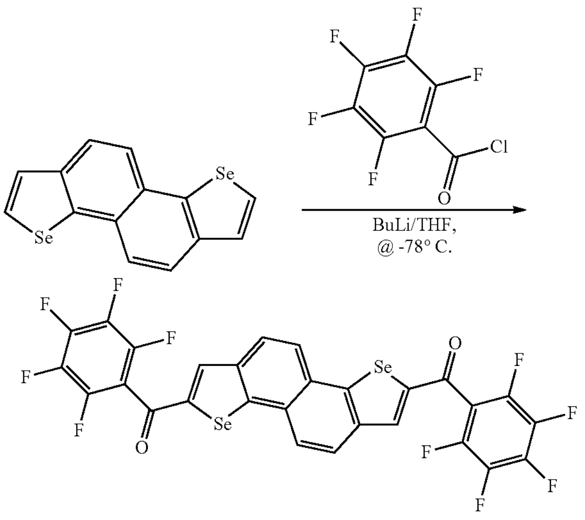

Naphtho[1,2-b:5,6-b']diselenophene (2 g, 6 mmol) is dissolved in 300 mL of anhydrous tetrahydrofuran and then, cooled to 0° C. under a nitrogen atmosphere. Subsequently, an n-butyl lithium solution (2.5 M in hexane, 6.3 mL) is added thereto in a dropwise fashion and then, stirred for 1 hour. The resultant is cooled to −78° C., and pentafluorobenzoyl chloride (2 mL, 15 mmol) is slowly added thereto in a dropwise fashion. The obtained mixture is slowly heated up to room temperature, and water is added thereto, completing a reaction. Subsequently, orange solids are filtered, washed with water and acetone, and dried, obtaining Compound 1AB. A yield thereof is 40%.

GC-MS (M+): 724

Synthesis Example 3

[Compound 1BA]

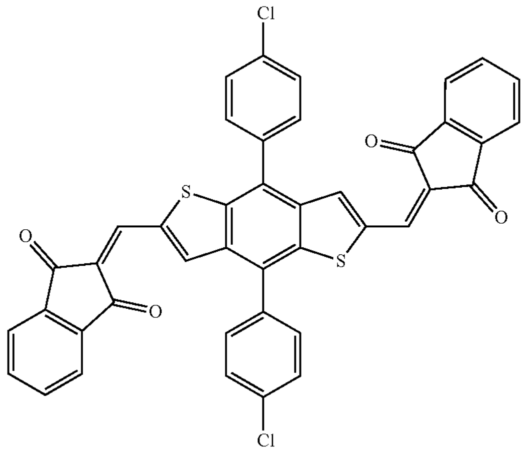

[Reaction Scheme 3]

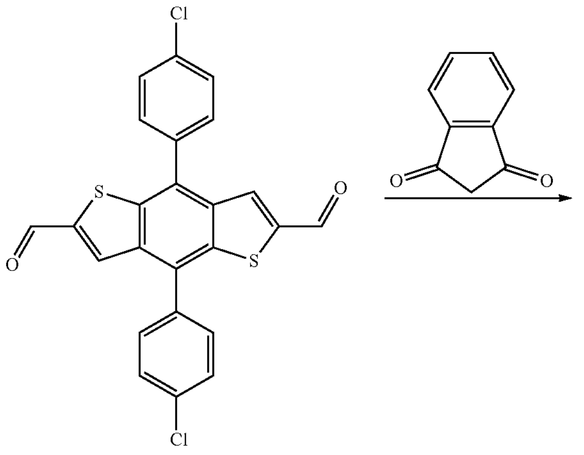

-continued

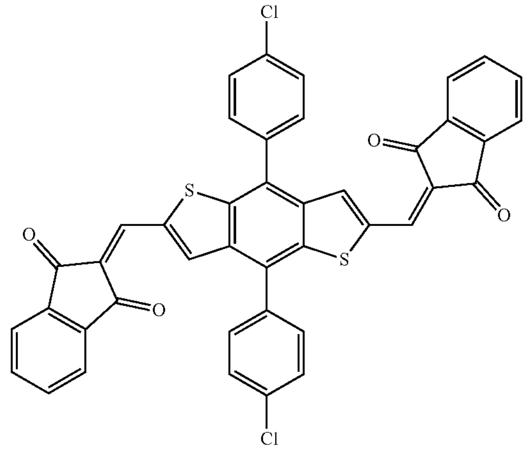

4,8-bis(4-chlorophenyl)benzo[1,2-b:4,5-b']dithiophene-2,6-dicarbaldehyde (1 g, 2.1 mmol) is dissolved in 52 mL of acetic acid, and 1H-indene-1,3(2H)-dione (0.6 g, 4.1 mmol) and ammonium acetate (0.81 g, 10.5 mmol) are added thereto and then, stirred at 110° C. for 20 hours. Subsequently, dark purple solids are filtered and washed with water and ethanol. The obtained solids are dispersed in tetrahydrofuran and then, stirred at 50° C. for 1 hour and filtered, obtaining the dark purple solids of Compound 1BA. A yield thereof is 70%.

GC-MS (M+): 722

Synthesis Example 4

[Compound 1CA]

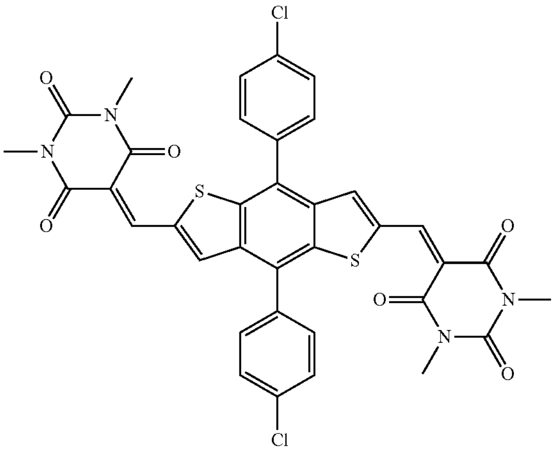

[Reaction Scheme 4]

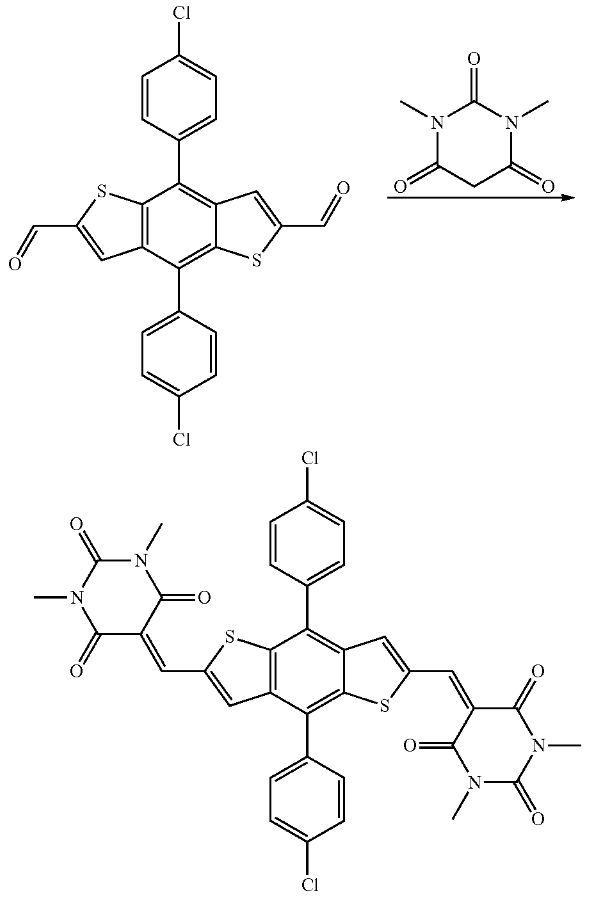

4,8-bis(4-chlorophenyl)benzo[1,2-b:4,5-b']dithiophene-2,6-dicarbaldehyde (1 g, 2.1 mmol) is dissolved in 52 mL of acetic acid, and 1,3-dimethylpyrimidine-2,4,6(1H,3H,5H)-trione (0.64 g, 4.1 mmol) and ammonium acetate (0.81 g, 10.5 mmol) are added thereto and then, stirred at 110° C. for 20 hours. Subsequently, dark purple solids are filtered and washed with water and ethanol. The solids are dispersed in acetone and tetrahydrofuran and then, stirred at 50° C. for 1 hour, the dark purple solids of Compound 1CA. A yield thereof is 70%.

GC-MS (M+): 742

Synthesis Example 5

[Compound 2A]

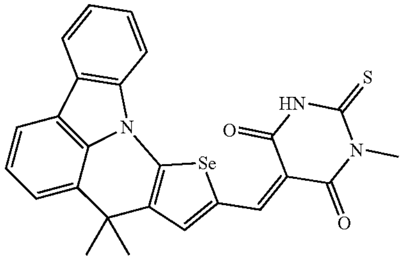

[Reaction Scheme 5]

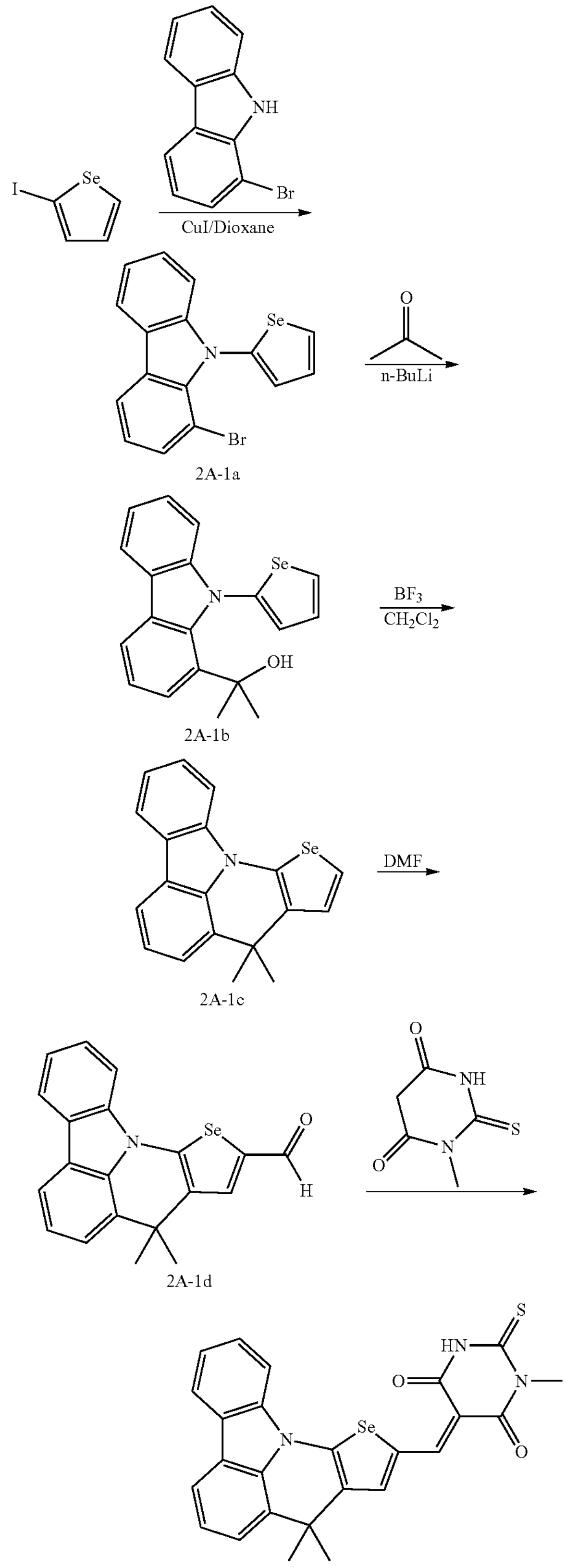

2A (i) Synthesis of Compound 2A-1a 9.4 g (36.5 mmol) of 2-Iodoselenophene and 7.5 g (30.5 mmol) of 1-bromo-9H-carbazole are dissolved in 30 ml of dioxane. 0.29 g (1.52 mmol) of copper(I) Iodide, 0.70 g (6.09 mmol) of trans-1,2-cyclohexanediamine, and 12.9 g (61.0 mmol) of tripotassium phosphate are added thereto and then, heated and refluxed for 30 hours. A product obtained therefrom is separated and purified through silica gel column chromatography (in a volume ratio of hexane: ethyl acetate=5:1) to obtain 8.18 g (Yield:72%) of Compound 2A-1a.

(ii) Synthesis of Compound 2A-1b 12.0 g (32.0 mmol) of Compound 2A-1a is dissolved in 300 ml of dehydrated diethyl ether. 12 ml (32.0 mmol) of a 2.76 M n-butyl lithium (n-BuLi) hexane solution is added thereto in a dropwise fashion at −50° C. and then, stirred for 1 hour at room temperature. 2.0 g (35.2 mmol) of dehydrated acetone (dimethylketone, $CH_3COCH_3$) is added thereto at −50° C. and then, stirred at room temperature for 2 hours. An organic layer extracted in diethyl ether is washed with a sodium chloride aqueous solution and then, dried by adding anhydrous magnesium sulfate thereto. Herein, a product obtained therefrom is separated and purified through silica gel column chromatography (in a volume ratio between hexane:dichloromethane=100:0 to 50:50 to obtain 6.3 g (Yield: 56%) of Compound 2A-1b.

(iii) Synthesis of Compound 2A-1c 6.23 g (17.6 mmol) of Compound 2A-1b is dissolved in 180 ml of dichloromethane. 4.98 g (35.5 mmol) of a boron trifluoride-ethyl ether complex is added thereto in a dropwise fashion at 0° C. and then, stirred for 2 hours. An organic layer extracted in dichloromethane is washed with a sodium chloride aqueous solution and then, dried by adding anhydrous magnesium sulfate thereto. Herein, a product obtained therefrom is separated and purified through silica gel column chromatography (in a volume ratio between hexane:dichloromethane=50:50) to obtain 5.12 g (Yield: 87%) of Compound 2A-1c.

(iv) Synthesis of Compound 2A-1d 1.9 ml (20.2 mmol) of phosphoryl chloride is added in a dropwise fashion to 6.0 ml (77.5 mmol) of N,N-dimethyl formamide (DMF) at −15° C. and then, stirred at room temperature for 2 hours. This solution is slowly dripped to 150 ml of a dichloromethane solution of 5.23 g (15.5 mmol) of Compound 2A-1c at −15° C., stirred at room temperature for 30 hours, and then, concentrated under a low pressure. Subsequently, water is added thereto, and a sodium hydroxide aqueous solution is added thereto until pH becomes 1 quadrivalent, and the obtained mixture is stirred at room temperature for 2 hours. An organic layer extracted with dichloromethane is washed with a sodium chloride aqueous solution and then, dried with anhydrous magnesium sulfate. A product obtained therefrom is separated and purified through silica gel column chromatography (in a volume ratio of hexane:dichloromethane=50:50) to obtain 3.34 g (Yield: 65%) of Compound 2A-1d (4,4-dimethyl-4H-selenopheno [3',2':5,6]pyrido[3,2,1-jk]carbazole-2-carbaldehyde).

(iv) Synthesis of Compound 2A 2.00 g (5.55 mmol) of Compound 2A-1d (4,4-dimethyl-4H-selenopheno[3',2':5,6]pyrido[3,2,1-jk]carbazole-2-carbaldehyde) is suspended in ethanol, and 1.05 g (6.66 mmol) of 1-methyl-2-thioxodihydropyrimidine-4,6(1H,5H)-dione is added thereto and then, reacted at 50° C. for 24 hours, obtaining 2.4 g of Compound 2A. A yield thereof is 86%. The obtained compound is purified through sublimation up to purity of 99.9%.

1H-NMR (500 MHz, Methylene Chloride-d2): δ 8.95 (s, 1H), 8.77 (s, 1H), 8.65 (s, 2H), 8.18 (s, 2H), 8.06 (d, 2H), 7.92 (d, 2H), 7.83 (d, 2H), 7.62 (d, 2H), 7.44 (t, 2H), 7.36 (m, 6H), 3.76 (s, 3H), 3.71 (s, 3H), 1.68 (s, 12H).

Evaluation I

The organic materials obtained in Synthesis Examples are deposited on a glass substrate, respectively, and energy levels of the deposited thin films are evaluated.

A HOMO energy level may be evaluated with an amount of photoelectrons emitted by energy when irradiating UV light to a thin film using AC-2 (Hitachi) or AC-3 (Riken Keiki Co., Ltd.). A LUMO energy level may be calculated by first obtaining bandgap energy with a UV-Vis spectrometer (Shimadzu Corporation) and then, using the bandgap energy and the HOMO energy level.

The results are shown in Tables 1 and 2.

TABLE 1

| | HOMO (eV) | LUMO (eV) | Energy bandgap (eV) |
|---|---|---|---|
| Synthesis Example 1 | 6.63 | 4.27 | 2.36 |
| Synthesis Example 2 | 5.70 | 2.83 | 2.87 |
| Synthesis Example 3 | 6.16 | 3.75 | 2.41 |
| Synthesis Example 4 | 5.97 | 3.59 | 2.38 |

* HOMO, LUMO: absolute value

TABLE 2

| | HOMO (eV) | LUMO (eV) | Energy bandgap (eV) |
|---|---|---|---|
| Synthesis Example 5 | 5.66 | 3.70 | 1.96 |

* HOMO, LUMO: absolute value

Evaluation II

The sublimation temperatures of the organic compounds according to Synthesis Examples are evaluated.

The sublimation temperatures are evaluated through a thermogravimetric analysis (TGA) by increasing a temperature under high vacuum of less than or equal to 10 Pa and then, taking a temperature at which a weight reduction of each sample by 10% occurs relative to the initial weight.

The results are shown in Tables 3 and 4.

TABLE 3

| | $T_{s(10)}$ (° C.) |
|---|---|
| Synthesis Example 1 | 182 |
| Synthesis Example 2 | 239 |
| Synthesis Example 3 | 345 |
| Synthesis Example 4 | 355 |

* $T_{s(10)}$ (° C.): a temperature at which a weight reduction of each sample by 10% occurs relative to the initial weight

TABLE 4

| | $T_{s(10)}$ (° C.) |
|---|---|
| Synthesis Example 5 | 270 |

* $T_{s(10)}$ (° C.): a temperature at which a weight reduction of each sample by 10% occurs relative to the initial weight

EXAMPLE: MANUFACTURE OF SENSOR I

Example 1

Al (10 nm), ITO (100 nm), and Al (8 nm) are sequentially deposited on a glass substrate to form a lower electrode (work function: 4.9 eV) having an Al/ITO/Al structure. Subsequently, N,N'-bis(3-methylphenyl)-N,N'-diphenyl-[1,1-biphenyl]-4,4'-diamine is deposited on the lower electrode to form a 170 nm-thick hole auxiliary layer (HOMO: 5.3 eV to 5.6 eV, LUMO: 2.0 eV to 2.3 eV). Subsequently, Compound 2A according to Synthesis Example 5 is deposited on the hole auxiliary layer to form a 10 nm-thick p-type semiconductor layer, and Compound 1AA of Synthesis Example 1 is deposited thereon to form a 5 nm-thick n-type semiconductor layer, obtaining a bi-layered photoelectric conversion layer ($\lambda_{max}$=530 nm). On the photoelectric conversion layer, 4,7-diphenyl-1,10-phenanthroline is deposited to form a 40 nm-thick electron auxiliary layer (HOMO: 6.1-6.4 eV, LUMO: 2.9-3.2 eV). Subsequently, on the electron auxiliary layer, magnesium and silver are deposited in a volume ratio of 1:10 to form a 20 nm-thick Mg:Ag upper electrode, and thus manufacturing a sensor.

Example 2

A sensor is manufactured in the same manner as in Example 1 except that Compound 1AB of Synthesis Example 2 is deposited instead of Compound 1AA of Synthesis Example 1 to form a 5 nm-thick n-type semiconductor layer.

Comparative Example 1

A sensor is manufactured in the same manner as in Example 1 except that a SubPc derivative (Compound C) is deposited instead of Compound 1AA of Synthesis Example 1 to form a 5 nm-thick n-type semiconductor layer.

[compound C]

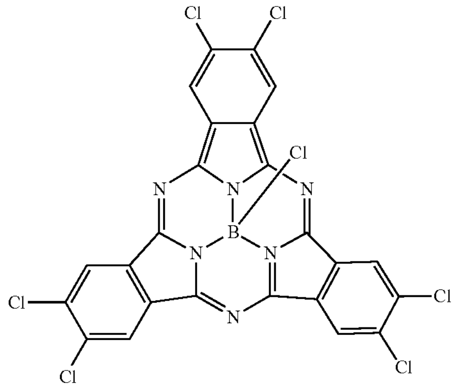

Evaluation III

The photoelectric conversion efficiency of the sensors according to Examples and Comparative Examples are evaluated.

The photoelectric conversion efficiency is evaluated by allowing the sensors according to the examples and the comparative examples to stand at 85° C. for 1 hour and then, measuring external quantum efficiency (EQE) thereof. The external quantum efficiency (EQE) is evaluated by IPCE (Incident Photon to Current Efficiency) at a wavelength of 450 nm (blue), 530 nm (green), and 630 nm (red).

The results are shown in Table 5.

TABLE 5

| | EQE (@3 V, %), 85° C. 1 h | | |
|---|---|---|---|
| | EQE (450 nm) | EQE (530 nm) | EQE (630 nm) |
| Example 1 | 1.4 | 36.2 | 0.0 |
| Example 2 | 0.8 | 13.0 | 0.0 |
| Comparative Example 1 | 0.5 | 2.5 | 1.3 |

Referring to Table 5, the sensors according to Examples, compared with the sensors according to Comparative Examples, exhibit improved photoelectric conversion efficiency in a green wavelength spectrum and in addition, higher photoelectric conversion efficiency at a green wavelength than at a blue wavelength or a red wavelength and thus high wavelength selectivity.

Evaluation IV

The dark currents under a reverse bias voltage of the sensors according to Examples and Comparative Examples are evaluated.

The dark current is evaluated by dark current density obtained by dividing a dark current measured with a current-voltage evaluation equipment (Keithley K4200 parameter analyzer) by a unit pixel area (0.04 $cm^2$), and the dark current density is evaluated from a current, when a reverse bias of −3 V is applied thereto.

The results are shown in Table 6.

TABLE 6

| | Dark current (mA/$cm^2$) |
|---|---|
| Example 1 | $2.3 \times 10^{-6}$ |
| Example 2 | $5.0 \times 10^{-6}$ |
| Comparative Example 1 | $6.4 \times 10^{-6}$ |

Referring to Table 6, the sensors according to Examples exhibit a low dark current when a reverse bias is applied thereto, compared with the sensors according to Comparative Examples.

While the inventive concepts have been described in connection with what is presently considered to be practical example embodiments, it is to be understood that the inventive concepts are not limited to such example embodiments. On the contrary, the inventive concepts are intended to cover various modifications and equivalent arrangements included within the spirit and scope of the appended claims.

What is claimed is:

1. An organic compound represented by Chemical Formula 1:

[Chemical Formula 1]

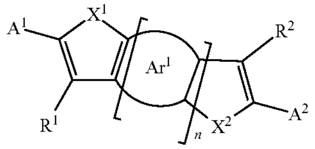

wherein, in Chemical Formula 1, $X^1$ and $X^2$ are each independently a chalcogen element, wherein at least one of $X^1$ or $X^2$ is Se or Te, $Ar^1$ is a substituted or unsubstituted C6 to C30 aromatic ring, n is 0 or 1, $R^1$ and $R^2$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, and $A^1$ and $A^2$ are each independently an electron accepting group represented by one of Chemical Formula 1A, Chemical Formula 1B, or Chemical Formula 1C:

[Chemical Formula 1A]

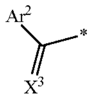

[Chemical Formula 1B]

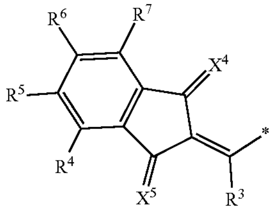

[Chemical Formula 1C]

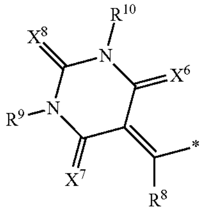

wherein, in Chemical Formulas 1A, 1B, and 1C, $X^3$ to $X^8$ are each independently a chalcogen element, and when $X^6$ and $X^7$ are each O, $X^8$ is not S, $Ar^2$ is a C6 to C30 aryl group substituted with at least one halogen, at least one C1 to C30 haloalkyl group, at least one cyano group, at least one dicyanovinyl group, or any combination thereof;

a C3 to C30 heterocyclic group substituted with at least one halogen, at least one C1 to C30 haloalkyl group, at least one cyano group, at least one dicyanovinyl group, or any combination thereof; or any combination thereof, $R^3$ to $R^{10}$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, $R^4$ to $R^7$ are each independently present or two adjacent ones of $R^4$ to $R^7$ are linked to each other to form a ring, and

* is a linking point with Chemical Formula 1.

2. The organic compound of claim 1, wherein $Ar^1$ is a substituted or unsubstituted benzene, a substituted or unsubstituted naphthalene, a substituted or unsubstituted anthracene, a substituted or unsubstituted phenanthrene, a substituted or unsubstituted tetracene, a substituted or unsubstituted furan, a substituted or unsubstituted thiophene, a substituted or unsubstituted selenophene, a substituted or unsubstituted tellurophene or a fused ring of two or more therefrom.

3. The organic compound of claim 2, wherein $Ar^1$ is one ring of a plurality of substituted or unsubstituted rings listed in Group 1:

[Group 1]

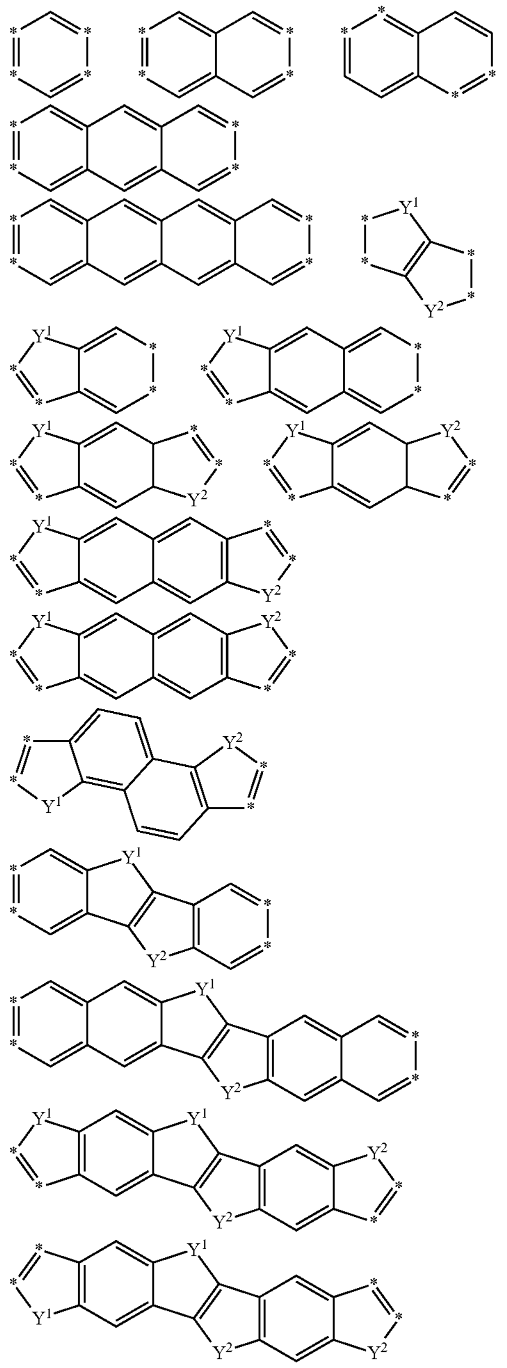

wherein, in Group 1, $Y^1$ and $Y^2$ are each independently a chalcogen element, and

* is a linking point with Chemical Formula 1.

4. The organic compound of claim 1, wherein $A^1$ and $A^2$ are each the electron accepting group represented by Chemical Formula 1A, respectively, and $Ar^2$ of Chemical Formula 1A is a halogen-substituted phenyl group; a halogen-substituted naphthyl group; a halogen-substituted anthracenyl group; a halogen-substituted phenanthrenyl group; a phenyl group substituted with a C1 to C30 haloalkyl group; a naphthyl group substituted with a C1 to C30 haloalkyl group; an anthracenyl group substituted with a C1 to C30 haloalkyl group; a phenanthrenyl group substituted with a C1 to C30 haloalkyl group; a phenyl group substituted with a cyano group; a naphthyl group substituted with a cyano group; an anthracenyl group substituted with a cyano group; a phenanthrenyl group substituted with a cyano group; a phenyl group substituted with a dicyanovinyl group; a naphthyl group substituted with a dicyanovinyl group; an anthracenyl group substituted with a dicyanovinyl group; a phenanthrenyl group substituted with a dicyanovinyl group; or any combination thereof.

5. The organic compound of claim 4, wherein $X^3$ is different from $X^1$ and $X^2$, respectively.

6. The organic compound of claim 1, wherein $A^1$ and $A^2$ are each an electron accepting group represented by Chemical Formula 1B, respectively, and $X^4$ and $X^5$ are different from $X^1$ and $X^2$, respectively.

7. The organic compound of claim 1, wherein $A^1$ and $A^2$ are each an electron accepting group represented by Chemical Formula 1C, respectively, and $X^6$, $X^7$, and $X^8$ are different from $X^1$ and $X^2$, respectively.

8. The organic compound of claim 1, wherein a LUMO energy level of the organic compound is about 2.5 eV to about 4.5 eV.

9. The organic compound of claim 1, wherein the organic compound is represented by one Chemical Formula of Chemical Formulas 1A-1 to 1A-4, 1B-1 to 1B-4, and 1C-1 to 1C-4:

[Chemical Formula 1A-1]

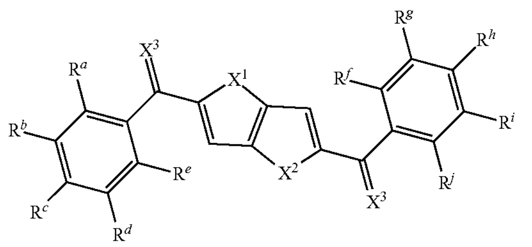

[Chemical Formula 1A-2]

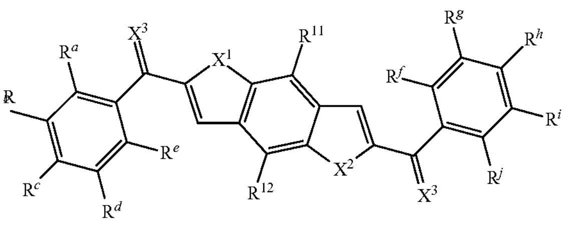

[Chemical Formula 1A-3]

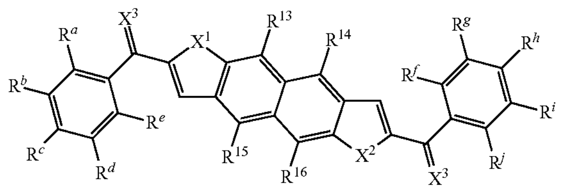

[Chemical Formula 1A-4]

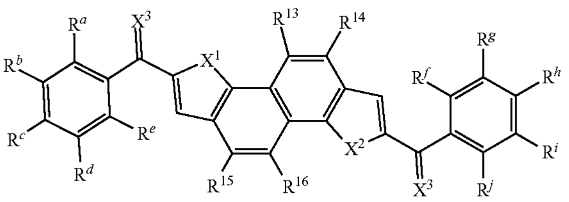

[Chemical Formula 1B-1]

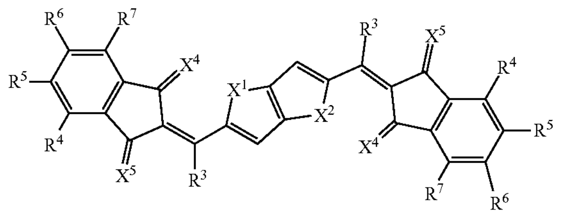

[Chemical Formula 1B-2]

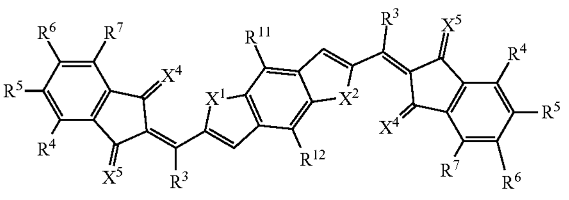

[Chemical Formula 1B-3]

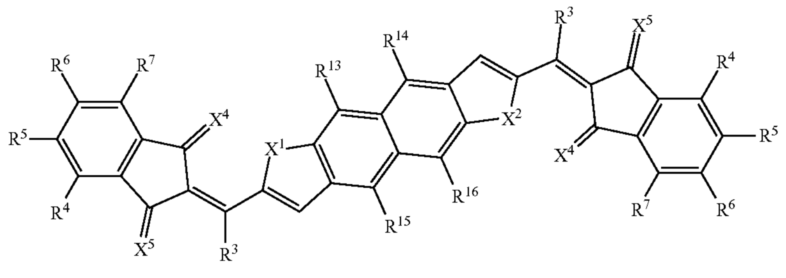

-continued

[Chemical Formula 1B-4]

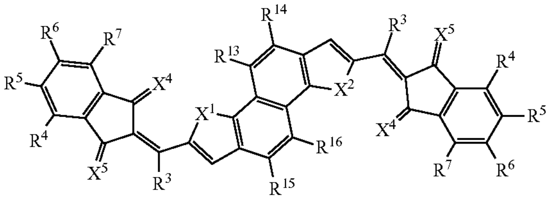

[Chemical Formula 1C-1]

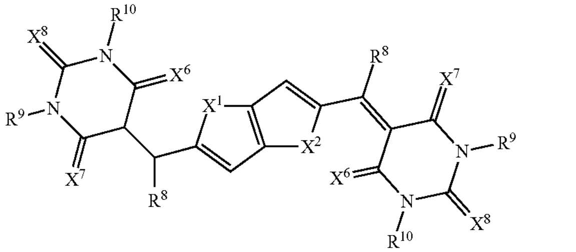

[Chemical Formula 1C-2]

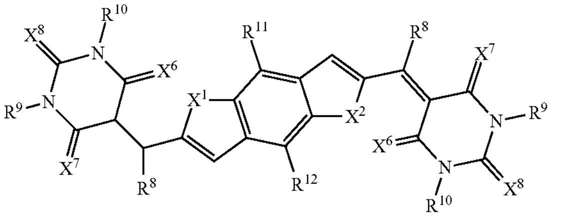

[Chemical Formula 1C-3]

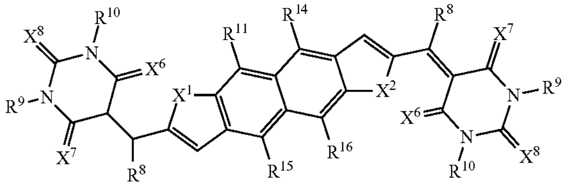

[Chemical Formula 1C-4]

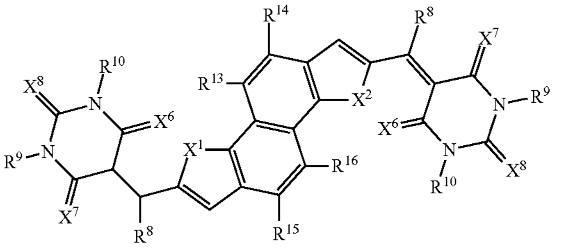

wherein, in Chemical Formulas 1A-1 to 1A-4, 1B-1 to 1B-4, and 1C-1 to 1C-4, $X^1$ to $X^8$ are each independently a chalcogen element, wherein at least one of $X^1$ or $X^2$ is Se or Te, and when $X^6$ and $X^7$ are each O, $X^8$ is not S, $R^3$ to $R^{16}$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, or any combination thereof, $R^a$ to $R^j$ are each independently hydrogen, a substituted or unsubstituted C1 to C30 alkyl group, a substituted or unsubstituted C2 to C30 alkenyl group, a substituted or unsubstituted C1 to C30 alkoxy group, a substituted or unsubstituted C6 to C30 aryl group, a substituted or unsubstituted C3 to C30 heterocyclic group, a halogen, a cyano group, a dicyanovinyl group, or any combination thereof, at least one of $R^a$ to $R^e$ is a halogen, a C1 to C30 haloalkyl group, a cyano group, a dicyanovinyl group, or any combination thereof, and at least one of $R^f$ to $R^j$ is a halogen, a C1 to C30 haloalkyl group, a cyano group, a dicyanovinyl group, or any combination thereof.

10. A sensor, comprising:

a first electrode, a second electrode, and a photoelectric conversion layer between the first electrode and the second electrode, the photoelectric conversion layer comprising the organic compound of claim 1.

11. The sensor of claim 10, wherein the organic compound is an n-type semiconductor, the photoelectric conversion layer further comprises a p-type semiconductor forming a pn junction with the organic compound, and the p-type semiconductor is represented by Chemical Formula 2:

[Chemical Formula 2]

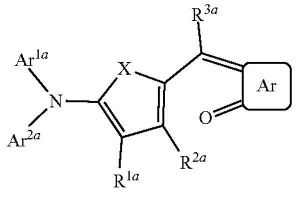

wherein, in Chemical Formula 2,

X is O, S, Se, Te, SO, $SO_2$, $CR^bR^c$, or $SiR^dR^e$,

Ar is a substituted or unsubstituted C6 to C30 arylene group, a substituted or unsubstituted C3 to C30 heterocyclic group, or a fused ring of two or more therefrom, $Ar^{1a}$ and $Ar^{2a}$ are each independently a substituted or unsubstituted C6 to C30 aryl (ene) group or a substituted or unsubstituted C3 to C30 heteroaryl (ene) group, $R^{1a}$ to $R^{3a}$ and $R^b$ to $R^e$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, and $Ar^{1a}$, $Ar^{2a}$, $R^{1a}$, and $R^{2a}$ are each independently present or two adjacent ones thereof are linked to each other to form a ring.

12. The sensor of claim 11, wherein the p-type semiconductor is represented by Chemical Formula 2A or Chemical Formula 2B:

[Chemical Formula 2A]

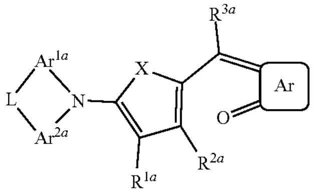

[Chemical Formula 2B]

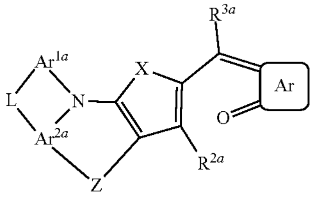

wherein, in Chemical Formulas 2A and 2B,

X is O, S, Se, Te, SO, $SO_2$, $CR^bR^c$, or $SiR^dR^e$,

Ar is a substituted or unsubstituted C6 to C30 arylene group, a substituted or unsubstituted C3 to C30 heterocyclic group, or a fused ring of two or more therefrom, $Ar^{1a}$ and $Ar^{2a}$ are each independently a substituted or unsubstituted C6 to C30 arylene group or a substituted or unsubstituted C3 to C30 heteroarylene group, L and Z are each independently a single bond, O, S, Se, Te, SO, $SO_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and $R^{1a}$, $R^{2a}$, $R^{3a}$, and $R^b$ to $R^l$ are each independently hydrogen, a substituted or unsubstituted C1 to C30 alkyl group, a substituted or unsubstituted C1 to C30 alkoxy group, a substituted or unsubstituted C6 to C30 aryl group, a A substituted or unsubstituted C3 to C30 heteroaryl group, a halogen, a cyano group, or any combination thereof.

13. A sensor-embedded display panel, comprising:

a substrate, a light emitting element on the substrate, the light emitting element including a light emitting layer, and a light absorption sensor on the substrate, the light absorption sensor including a photoelectric conversion layer, wherein the light emitting element and the light absorption sensor are arranged in parallel along an in-plane direction of the substrate such that the photoelectric conversion layer and the light emitting layer at least partially overlap in the in-plane direction, and wherein the photoelectric conversion layer comprises the organic compound of claim 1.

14. The sensor-embedded display panel of claim 13, wherein the organic compound is an n-type semiconductor, the photoelectric conversion layer further comprises a p-type semiconductor forming a pn junction with the organic compound, and the p-type semiconductor is represented by Chemical Formula 2:

[Chemical Formula 2]

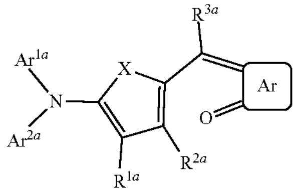

wherein, in Chemical Formula 2,

X is O, S, Se, Te, SO, $SO_2$, $CR^bR^c$, or $SiR^dR^e$,

Ar is a substituted or unsubstituted C6 to C30 arylene group, a substituted or unsubstituted C3 to C30 heterocyclic group, or a fused ring of two or more therefrom, $Ar^{1a}$ and $Ar^{2a}$ are each independently a substituted or unsubstituted C6 to C30 aryl (ene) group or a substituted or unsubstituted C3 to C30 heteroaryl (ene) group, $R^{1a}$ to $R^{3a}$ and $R^b$ to $R^e$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, and $Ar^{1a}$, $Ar^{2a}$, $R^{1a}$, and $R^{2a}$ are each independently present or two adjacent ones thereof are linked to each other to form a ring.

15. The sensor-embedded display panel of claim 14, wherein the p-type semiconductor is represented by Chemical Formula 2A or Chemical Formula 2B:

[Chemical Formula 2A]

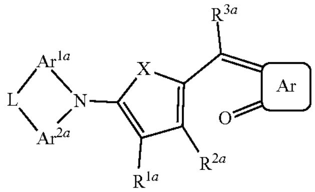

[Chemical Formula 2B]

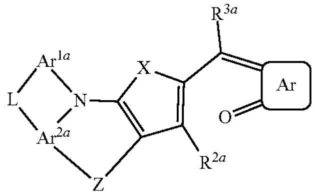

wherein, in Chemical Formulas 2A and 2B,

X is O, S, Se, Te, SO, $SO_2$, $CR^bR^c$, or $SiR^dR^e$,

Ar is a substituted or unsubstituted C6 to C30 arylene group, a substituted or unsubstituted C3 to C30 heterocyclic group, or a fused ring of two or more therefrom, $Ar^{1a}$ and $Ar^{2a}$ are each independently a substituted or unsubstituted C6 to C30 arylene group or a substituted or unsubstituted C3 to C30 heteroarylene group, L and Z are each independently a single bond, O, S, Se, Te, SO, $SO_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and $R^{1a}$, $R^{2a}$, $R^{3a}$ and $R^b$ to $R^l$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof.

16. The sensor-embedded display panel of claim 13, wherein the light emitting element comprises a plurality of light emitting elements, the plurality of light emitting elements including a first light emitting element, a second light emitting element, and a third light emitting element, the plurality of light emitting elements configured to emit light of different wavelength spectra in relation to each other, and the light absorption sensor is configured to absorb light emitted from at least one light emitting element of the first light emitting element, the second light emitting element, or the third light emitting element and then reflected by a recognition target to the light absorption sensor and convert the absorbed light into an electrical signal.

17. The sensor-embedded display panel of claim 13, wherein the light emitting element and the light absorption sensor each comprise a separate portion of a common electrode configured to apply a common voltage to the light emitting element and the light absorption sensor, respectively, and the sensor-embedded display panel further comprises a first common auxiliary layer that is a single piece of material that extends continuously between the light emitting layer and the common electrode, and between the photoelectric conversion layer and the common electrode.

18. The sensor-embedded display panel of claim 17, wherein a difference between a LUMO energy level of the first common auxiliary layer and a LUMO energy level of the organic compound is about 0 eV to about 1.2 eV.

19. The sensor-embedded display panel of claim 13, further comprising a second common auxiliary layer that is a single piece of material that extends continuously between the light emitting layer and the substrate and between the photoelectric conversion layer and the substrate.

20. The sensor-embedded display panel of claim 13, wherein the sensor-embedded display panel comprises a display area configured to display a color, and a non-display area excluding the display area, and the light absorption sensor is in the non-display area.

21. The sensor-embedded display panel of claim 20, wherein the light emitting element comprises a first light emitting element configured to emit light of a red wavelength spectrum, a second light emitting element configured to emit light of a green wavelength spectrum, and a third light emitting element configured to emit light of a blue wavelength spectrum, the display area comprises a plurality of first subpixels comprising the first light emitting element and configured to display the light of the red wavelength spectrum, a plurality of second subpixels comprising the second light emitting element and configured to display the light of the green wavelength spectrum, and a plurality of third subpixels comprising the third light emitting element and configured to display the light of the blue wavelength spectrum, and the light absorption sensor is between at least two subpixels of a first subpixel of the plurality of first subpixels, a second subpixel of the plurality of second subpixels, or a third subpixel of the plurality of third subpixels.

22. An electronic device comprising the sensor of claim 10.

23. An electronic device comprising the sensor-embedded display panel of claim 13.

* * * * *